United States Patent
Cheney

(10) Patent No.: US 11,130,205 B2
(45) Date of Patent: Sep. 28, 2021

(54) CRACK RESISTANT HARDFACING ALLOYS

(71) Applicant: Oerlikon Metco (US) Inc., Westbury, NY (US)

(72) Inventor: Justin Lee Cheney, Encinitas, CA (US)

(73) Assignee: Oerlikon Metco (US) Inc., Westbury, NY (US)

( * ) Notice: Subject to any disclaimer, the term of this patent is extended or adjusted under 35 U.S.C. 154(b) by 565 days.

(21) Appl. No.: 14/733,519

(22) Filed: Jun. 8, 2015

(65) Prior Publication Data

US 2015/0354036 A1 Dec. 10, 2015

Related U.S. Application Data

(60) Provisional application No. 62/009,758, filed on Jun. 9, 2014.

(51) Int. Cl.
*C22C 38/18* (2006.01)
*C22C 37/06* (2006.01)
(Continued)

(52) U.S. Cl.
CPC .............. *B23P 6/04* (2013.01); *B23K 9/042* (2013.01); *B23K 9/173* (2013.01); *B23K 35/004* (2013.01); *B23K 35/0261* (2013.01); *B23K 35/308* (2013.01); *B23K 35/3086* (2013.01); *B23K 35/3601* (2013.01); *C22C 37/06* (2013.01); *C22C 37/10* (2013.01); *C22C 38/02* (2013.01); *C22C 38/04* (2013.01); *C22C 38/22* (2013.01); *C22C 38/24* (2013.01); *C22C 38/26* (2013.01); *C22C 38/28* (2013.01); *C22C 38/32* (2013.01); *C22C 38/36* (2013.01); *C22C 38/38* (2013.01); *B23K 2101/34* (2018.08)

(58) Field of Classification Search
CPC ......... C22C 38/38; C22C 38/36; C22C 38/32; C22C 38/28; C22C 38/26; C22C 38/24; C22C 38/22; C22C 37/06
See application file for complete search history.

(56) References Cited

U.S. PATENT DOCUMENTS 2,043,952 A 6/1936 Ffield
2,156,306 A 5/1939 Rapatz
(Continued)

FOREIGN PATENT DOCUMENTS

CA 2774546 1/2015
CN 102233490 A 11/2011
(Continued)

OTHER PUBLICATIONS

Ohmura. Evaluation of temper softening behavior of Fe—C binary martensitic steels by nanoindentation. Scripta Materialia. vol. 49, Issue 12, Dec. 2003, pp. 1157-1162.*
(Continued)

*Primary Examiner* — Matthew E. Hoban
(74) *Attorney, Agent, or Firm* — Knobbe, Martens, Olson & Bear, LLP

(57) ABSTRACT

Embodiments of an alloy that can be resistant to cracking. In some embodiments, the alloy can be advantageous for use as a hardfacing alloys, in both a diluted and undiluted state. Certain microstructural, thermodynamic, and performance criteria can be met by embodiments of the alloys that may make them advantageous for hardfacing.

12 Claims, 4 Drawing Sheets

(51) Int. Cl.
*B23P 6/04* (2006.01)
*B23K 35/30* (2006.01)
*B23K 35/36* (2006.01)
*B23K 35/00* (2006.01)
*C22C 37/10* (2006.01)
*C22C 38/02* (2006.01)
*C22C 38/04* (2006.01)
*C22C 38/22* (2006.01)
*C22C 38/24* (2006.01)
*C22C 38/26* (2006.01)
*C22C 38/28* (2006.01)
*C22C 38/32* (2006.01)
*C22C 38/36* (2006.01)
*C22C 38/38* (2006.01)
*B23K 9/04* (2006.01)
*B23K 9/173* (2006.01)
*B23K 35/02* (2006.01)
*B23K 101/34* (2006.01)

(56) References Cited

U.S. PATENT DOCUMENTS

| | | |
|---|---|---|
| 2,608,495 A | 8/1952 | Barry |
| 2,873,187 A | 2/1959 | Dyrkaez et al. |
| 2,936,229 A | 5/1960 | Shepard |
| 3,024,137 A | 3/1962 | Witherell |
| 3,113,021 A | 12/1963 | Witherell |
| 3,181,970 A | 5/1965 | Witherell et al. |
| 3,303,063 A | 2/1967 | Pietryka et al. |
| 3,448,241 A | 6/1969 | Penson et al. |
| 3,554,792 A | 1/1971 | Johnson |
| 3,650,734 A | 3/1972 | Kantor et al. |
| 3,843,359 A | 10/1974 | Fiene et al. |
| 3,859,060 A | 1/1975 | Eiselstein et al. |
| 3,942,954 A | 3/1976 | Frehn |
| 3,975,612 A | 8/1976 | Nakazaki et al. |
| 4,010,309 A | 3/1977 | Peterson |
| 4,017,339 A | 4/1977 | Okuda et al. |
| 4,042,383 A | 8/1977 | Petersen et al. |
| 4,066,451 A | 1/1978 | Rudy |
| 4,214,145 A | 7/1980 | Zvanut et al. |
| 4,235,630 A | 11/1980 | Babu |
| 4,255,709 A | 3/1981 | Zatsepium et al. |
| 4,277,108 A | 7/1981 | Wallace |
| 4,297,135 A | 10/1981 | Giessen et al. |
| 4,318,733 A | 3/1982 | Ray et al. |
| 4,365,994 A | 12/1982 | Ray |
| 4,415,530 A | 11/1983 | Hunt |
| 4,419,130 A | 12/1983 | Slaughter |
| 4,576,653 A | 3/1986 | Ray |
| 4,596,282 A | 6/1986 | Maddy et al. |
| 4,606,977 A | 8/1986 | Dickson et al. |
| 4,635,701 A | 1/1987 | Sare et al. |
| 4,638,847 A | 1/1987 | Day |
| 4,639,576 A | 1/1987 | Shoemaker et al. |
| 4,666,797 A | 5/1987 | Newman et al. |
| 4,673,550 A | 6/1987 | Dallaire et al. |
| 4,762,681 A | 8/1988 | Tassen et al. |
| 4,803,045 A | 2/1989 | Ohriner et al. |
| 4,822,415 A | 4/1989 | Dorfman et al. |
| 4,919,728 A | 4/1990 | Kohl et al. |
| 4,981,644 A | 1/1991 | Chang |
| 5,094,812 A | 3/1992 | Dulmaine et al. |
| 5,252,149 A | 10/1993 | Dolman |
| 5,306,358 A | 4/1994 | Lai et al. |
| 5,375,759 A | 12/1994 | Hiraishi et al. |
| 5,567,251 A | 10/1996 | Peker et al. |
| 5,570,636 A | 11/1996 | Lewis |
| 5,618,451 A | 4/1997 | Ni |
| 5,820,939 A | 10/1998 | Popoola et al. |
| 5,858,558 A | 1/1999 | Zhao et al. |
| 5,861,605 A | 1/1999 | Ogawa et al. |
| 5,907,017 A | 5/1999 | Ober et al. |
| 5,935,350 A | 8/1999 | Raghu et al. |
| 5,942,289 A | 8/1999 | Jackson |
| 5,988,302 A | 11/1999 | Sreshta et al. |
| 6,117,493 A | 9/2000 | North |
| 6,171,222 B1 * | 1/2001 | Lakeland et al. .......... 492/54 |
| 6,210,635 B1 | 4/2001 | Jackson et al. |
| 6,232,000 B1 | 5/2001 | Singh et al. |
| 6,326,582 B1 | 12/2001 | North |
| 6,331,688 B1 | 12/2001 | Halleén et al. |
| 6,332,936 B1 | 12/2001 | Hajaligo et al. |
| 6,375,895 B1 | 4/2002 | Daemen |
| 6,398,103 B2 | 6/2002 | Hasz et al. |
| 6,441,334 B1 | 8/2002 | Aida et al. |
| 6,582,126 B2 | 6/2003 | North |
| 6,608,286 B2 | 8/2003 | Jiang |
| 6,669,790 B1 | 12/2003 | Gundlach et al. |
| 6,689,234 B2 | 2/2004 | Branagan |
| 6,702,905 B1 | 3/2004 | Qiao et al. |
| 6,702,906 B2 | 3/2004 | Ogawa et al. |
| 6,750,430 B2 | 6/2004 | Kelly |
| 7,052,561 B2 | 5/2006 | Lu et al. |
| 7,219,727 B2 | 5/2007 | Slack et al. |
| 7,285,151 B2 | 10/2007 | Sjodin et al. |
| 7,361,411 B2 | 4/2008 | Daemen et al. |
| 7,491,910 B2 | 2/2009 | Kapoor et al. |
| 7,553,382 B2 | 6/2009 | Branagan et al. |
| 7,569,286 B2 | 8/2009 | Daemen et al. |
| 7,776,451 B2 | 8/2010 | Jiang et al. |
| 7,935,198 B2 | 5/2011 | Branagan et al. |
| 8,070,894 B2 | 12/2011 | Branagan |
| 8,097,095 B2 | 1/2012 | Branagan |
| 8,153,935 B2 | 4/2012 | Jang et al. |
| 8,187,529 B2 | 5/2012 | Powell |
| 8,187,725 B2 | 5/2012 | Kiser et al. |
| 8,268,453 B2 | 9/2012 | Dallaire |
| 8,474,541 B2 | 7/2013 | Branagan et al. |
| 8,562,759 B2 | 10/2013 | Cheney et al. |
| 8,562,760 B2 | 10/2013 | Cheney et al. |
| 8,640,941 B2 | 2/2014 | Cheney |
| 8,647,449 B2 | 2/2014 | Cheney et al. |
| 8,658,934 B2 | 2/2014 | Branagan et al. |
| 8,662,143 B1 | 3/2014 | Foster |
| 8,702,835 B2 | 4/2014 | Yu et al. |
| 8,703,046 B2 | 4/2014 | Hanejko et al. |
| 8,704,134 B2 | 4/2014 | Branagan et al. |
| 8,777,090 B2 | 7/2014 | Miller et al. |
| 8,801,872 B2 | 8/2014 | Wright et al. |
| 8,808,471 B2 | 8/2014 | Wright et al. |
| 8,858,675 B2 | 10/2014 | Larsson |
| 8,870,997 B2 | 10/2014 | Klekovkin et al. |
| 8,911,662 B2 | 12/2014 | Larsson |
| 8,920,938 B2 | 12/2014 | Hesse et al. |
| 8,973,806 B2 | 3/2015 | Cheney |
| 8,992,659 B2 | 3/2015 | Larsson et al. |
| 9,051,635 B2 | 6/2015 | Jou |
| 9,095,932 B2 | 8/2015 | Miller et al. |
| 9,145,598 B2 | 9/2015 | Oshchepkov |
| 9,174,293 B2 | 11/2015 | Lee |
| 9,193,011 B2 | 11/2015 | Mars et al. |
| 9,233,419 B2 | 1/2016 | Gries |
| 9,255,309 B2 | 2/2016 | Aimone |
| 9,309,585 B2 | 4/2016 | Cheney et al. |
| 9,314,848 B2 | 4/2016 | Larsson |
| 9,340,855 B2 | 5/2016 | Schade et al. |
| 9,394,591 B2 | 7/2016 | Deodeshmukh et al. |
| 9,399,907 B2 | 7/2016 | Mo et al. |
| 9,469,890 B2 | 10/2016 | Bengtsson |
| 9,540,711 B2 | 1/2017 | Fifield |
| 9,580,773 B2 | 2/2017 | Aimone et al. |
| 9,631,262 B2 | 4/2017 | Wright et al. |
| 2001/0019781 A1 | 9/2001 | Hasz |
| 2002/0054972 A1 | 5/2002 | Charpentier et al. |
| 2002/0098298 A1 | 7/2002 | Bolton et al. |
| 2002/0148533 A1 | 10/2002 | Kim et al. |
| 2004/0062677 A1 | 4/2004 | Chabenat et al. |
| 2004/0079742 A1 | 4/2004 | Kelly |
| 2004/0115086 A1 | 6/2004 | Chabenat et al. |
| 2004/0206726 A1 | 10/2004 | Daemen et al. |
| 2005/0047952 A1 | 3/2005 | Coleman |

(56) References Cited

U.S. PATENT DOCUMENTS

| | | |
|---|---|---|
| 2005/0109431 A1 | 5/2005 | Kernan et al. |
| 2006/0063020 A1 | 3/2006 | Barbezat |
| 2006/0093752 A1 | 5/2006 | Darolia et al. |
| 2006/0191606 A1 | 8/2006 | Ogawa et al. |
| 2006/0260583 A1 | 11/2006 | Abi-Akar et al. |
| 2007/0029295 A1 | 2/2007 | Branagan |
| 2007/0090167 A1 | 4/2007 | Arjakine et al. |
| 2007/0187369 A1 | 8/2007 | Menon et al. |
| 2007/0253856 A1 | 11/2007 | Vecchio et al. |
| 2007/0284018 A1 | 12/2007 | Hamano et al. |
| 2008/0001115 A1 | 1/2008 | Qiao et al. |
| 2008/0031769 A1 | 2/2008 | Yeh |
| 2008/0149397 A1 | 6/2008 | Branagan |
| 2008/0241580 A1 | 10/2008 | Kiser et al. |
| 2008/0241584 A1 | 10/2008 | Daemen et al. |
| 2009/0017328 A1 | 1/2009 | Katoh et al. |
| 2009/0123765 A1 | 5/2009 | Branagan |
| 2009/0252636 A1 | 10/2009 | Christopherson, Jr. et al. |
| 2009/0258250 A1 | 10/2009 | Daemen et al. |
| 2009/0285715 A1 | 11/2009 | Arjakine et al. |
| 2010/0009089 A1 | 1/2010 | Junod et al. |
| 2010/0028706 A1 | 2/2010 | Hornschu et al. |
| 2010/0044348 A1 | 2/2010 | Buchmann |
| 2010/0101780 A1 | 4/2010 | Ballew et al. |
| 2010/0155236 A1 | 6/2010 | Lee et al. |
| 2010/0166594 A1 | 7/2010 | Hirata et al. |
| 2010/0189588 A1 | 7/2010 | Kawatsu et al. |
| 2010/0258217 A1 | 10/2010 | Kuehmann |
| 2011/0004069 A1 | 1/2011 | Ochs et al. |
| 2011/0031222 A1 | 2/2011 | Branagan et al. |
| 2011/0064963 A1 | 3/2011 | Cheney et al. |
| 2011/0100720 A1 | 5/2011 | Branagan et al. |
| 2011/0139761 A1 | 6/2011 | Sugahara et al. |
| 2011/0142713 A1 | 6/2011 | Kawasaki et al. |
| 2011/0162612 A1 | 7/2011 | Qiao et al. |
| 2011/0171485 A1 | 7/2011 | Kawamoto et al. |
| 2011/0220415 A1 | 9/2011 | Jin et al. |
| 2012/0055903 A1 | 3/2012 | Izutani et al. |
| 2012/0103456 A1 | 5/2012 | Smith et al. |
| 2012/0156020 A1 | 6/2012 | Kottilingam et al. |
| 2012/0160363 A1 | 6/2012 | Jin et al. |
| 2012/0288400 A1 | 11/2012 | Hirata et al. |
| 2013/0094900 A1 | 4/2013 | Folkmann et al. |
| 2013/0167965 A1 | 4/2013 | Cheney et al. |
| 2013/0224516 A1 | 8/2013 | Kusinski et al. |
| 2013/0260177 A1 | 10/2013 | Wallin et al. |
| 2013/0266798 A1 | 10/2013 | Cheney |
| 2013/0294962 A1 | 11/2013 | Wallin et al. |
| 2014/0044587 A1 | 2/2014 | Crook et al. |
| 2014/0044617 A1 | 2/2014 | Dreisinger |
| 2014/0006531 A1 | 3/2014 | Cheney |
| 2014/0060707 A1 | 3/2014 | Wright et al. |
| 2014/0065316 A1 | 3/2014 | Cheney |
| 2014/0105780 A1 | 4/2014 | Cheney |
| 2014/0131338 A1 | 5/2014 | Postle |
| 2014/0171367 A1 | 6/2014 | Murthy et al. |
| 2014/0219859 A1 | 8/2014 | Cheney |
| 2014/0234154 A1 | 8/2014 | Cheney et al. |
| 2014/0248509 A1 | 9/2014 | Cheney |
| 2014/0263248 A1 | 9/2014 | Postle |
| 2014/0295194 A1 | 10/2014 | Yoshitaka et al. |
| 2014/0322064 A1 | 10/2014 | Gerk et al. |
| 2014/0356223 A1 | 12/2014 | Nilsson et al. |
| 2015/0004337 A1 | 1/2015 | Zimmermann et al. |
| 2015/0075681 A1 | 3/2015 | Wright et al. |
| 2015/0086413 A1 | 3/2015 | Wolverton et al. |
| 2015/0106035 A1 | 4/2015 | Vecchio et al. |
| 2015/0147591 A1 | 5/2015 | Cheney |
| 2015/0152994 A1 | 6/2015 | Bondil et al. |
| 2015/0252631 A1 | 9/2015 | Miller |
| 2015/0275341 A1 | 10/2015 | Cheney |
| 2015/0284817 A1 | 10/2015 | Snyder et al. |
| 2015/0284829 A1 | 10/2015 | Cheney |
| 2015/0298986 A1 | 10/2015 | Billieres et al. |
| 2015/0307968 A1 | 10/2015 | Mars et al. |
| 2015/0367454 A1 | 12/2015 | Cheney |
| 2016/0001368 A1 | 1/2016 | Gries et al. |
| 2016/0002752 A1 | 1/2016 | Srivastava et al. |
| 2016/0002764 A1 | 1/2016 | Gries et al. |
| 2016/0017463 A1 | 1/2016 | Cheney |
| 2016/0024621 A1 | 1/2016 | Cheney |
| 2016/0024624 A1 | 1/2016 | Cheney |
| 2016/0024628 A1 | 1/2016 | Cheney |
| 2016/0040262 A1 | 2/2016 | Snyder et al. |
| 2016/0083830 A1 | 3/2016 | Cheney |
| 2016/0114392 A1 | 4/2016 | Berg et al. |
| 2016/0138144 A1 | 5/2016 | Olsérius |
| 2016/0168670 A1 | 6/2016 | Cheney |
| 2016/0195216 A1 | 7/2016 | Bondil et al. |
| 2016/0201169 A1 | 7/2016 | Vecchio |
| 2016/0201170 A1 | 7/2016 | Vecchio |
| 2016/0215374 A1 | 7/2016 | Schade et al. |
| 2016/0222490 A1 | 8/2016 | Wright et al. |
| 2016/0243616 A1 | 8/2016 | Gries |
| 2016/0258044 A1 | 9/2016 | Litström et al. |
| 2016/0289001 A1 | 10/2016 | Shibata et al. |
| 2016/0289798 A1 | 10/2016 | Deodeshmukh et al. |
| 2016/0289799 A1 | 10/2016 | Crook et al. |
| 2016/0289803 A1 | 10/2016 | Cheney |
| 2016/0376686 A1 | 12/2016 | Jou |
| 2017/0014865 A1 | 1/2017 | Kusinski et al. |
| 2017/0044646 A1 | 2/2017 | Gong et al. |
| 2017/0066090 A1 | 3/2017 | Eibl |
| 2017/0067138 A1 | 3/2017 | Vecchio et al. |
| 2017/0080531 A1 | 3/2017 | Cheney |
| 2017/0130311 A1 | 5/2017 | Cheney |

FOREIGN PATENT DOCUMENTS

| | | |
|---|---|---|
| CN | 102686762 | 3/2014 |
| CN | 103635284 | 3/2014 |
| CN | 104039483 | 9/2014 |
| CN | 104838032 | 8/2015 |
| DE | 2754437 | 7/1979 |
| DE | 33 20 513 | 12/1983 |
| EP | 0 365 884 | 5/1990 |
| EP | 1 338 663 | 8/2003 |
| EP | 2 305 415 | 8/2003 |
| EP | 1 857 204 | 11/2007 |
| EP | 2 778 247 | 9/2014 |
| EP | 2 563 942 | 10/2015 |
| EP | 2890823 | 3/2017 |
| EP | 2659014 | 4/2017 |
| GB | 2 153 846 A | 8/1985 |
| IN | MUMNP-2003-00842 | 4/2005 |
| JP | 58-132393 | 8/1983 |
| JP | 60-133996 A | 7/1985 |
| JP | 6031897 B2 | 7/1985 |
| JP | 63-026205 A | 2/1988 |
| JP | 63-65056 A | 3/1988 |
| JP | 03-133593 A | 6/1991 |
| JP | 04-358046 A | 12/1992 |
| JP | 2012-000616 | 1/2012 |
| KR | 10-0935816 B1 | 1/2010 |
| TW | 200806801 A | 2/2008 |
| WO | WO 1984/000385 | 2/1984 |
| WO | WO 1984/004760 | 12/1984 |
| WO | WO 2006/086350 | 8/2006 |
| WO | WO 2008/153499 | 12/2008 |
| WO | WO 2011/035193 | 9/2010 |
| WO | WO 2011/021751 | 2/2011 |
| WO | WO 2011/071054 | 6/2011 |
| WO | WO 2011/158706 | 12/2011 |
| WO | WO 2012/037339 | 3/2012 |
| WO | WO 2012/129505 | 9/2012 |
| WO | WO 2013/101561 | 7/2013 |
| WO | WO 2013/133944 | 9/2013 |
| WO | WO 2014/059177 | 4/2014 |
| WO | WO 2014/081491 | 5/2014 |
| WO | WO 2014/114714 | 7/2014 |
| WO | WO 2014/114715 | 7/2014 |
| WO | WO 2015/081209 | 6/2015 |

(56) References Cited

FOREIGN PATENT DOCUMENTS

| WO | WO 2015/183955 | 12/2015 |
|---|---|---|
| WO | WO 2016/010599 | 1/2016 |
| ZA | 2013/02311 | 12/2013 |

OTHER PUBLICATIONS

MO-C Phase Diagram [online], [retrieved on Jan. 27, 2015]. Retrieved rom the internet: <URL:http://Factsage.cn/fact/documentation/SGTE/C-MO.jpg> (Year: 2015).*

Nb—C Phase Diagram [online], [retrieved on Jan. 27, 2015]. Retrieved rom the internet: <URL:http://www.crct.polymtl.ca/fact/documentation/BINARY/C-Nb.jpg (Year: 2015).*

International Search Report and Written Opinion re PCT Application No. PCT/US2015/034702, dated Sep. 2, 2015.

Audouard, et al.: "Corrosion Performance and Field Experience With Super Duplex and Super Austenitic Stainless Steels in FGD Systems", Corrosion 2000; p. 4, table 2.

Branagan, et al.: Developing extreme hardness (>15GPa) in iron based nanocomosites, Composites Part A: Applied Science and Manufacturing, Elsevier Science Publishers B.V., Amsterdam, NL, vol. 33, No. 6, Jun. 1, 2002, pp. 855-859.

Cheney, et al.: "Development of quaternary Fe-based bulk metallic glasses," Materials Science and Engineering, vol. 492, No. 1-2, Sep. 25, 2008, pp. 230-235.

Cheney: Modeling the Glass Forming Ability of Metals. A Dissertation submitted in partial satisfaction of the Requirements for the degree of Doctor of Philosophy. University of California, San Diego. Dec. 2007.

Cr—C Phase Diagram [online], [retrieved on Jan. 27, 2015]. Retrieved from the Internet: http://www.azom.com/work/3ud2quvLOU9g4VBMjVEh_files/image002.gif.

Davis, Jr, ed. Stainless steels. ASM International, 1994; p. 447.

Iron-Carbon (Fe—C) Phase diagram [online], [retrieved on Jan. 27, 2014]. Retrieved from the Internet: <URL:http://www.calphad.com/iron-carbon.html>.

Khalifa, et al.: "Effect of Mo—Fe substitution on glass forming ability, thermal stability, and hardness of Fe—C—B—Mo—Cr—W bulk amorphous allows," Materials Science and Engineering, vol. 490, No. 1-2, Aug. 25, 2008, pp. 221-228.

Miracle, D.B.: The efficient cluster packing model—An atomic structural model for metallic glasses, Acta Materialia vol. 54, Issue 16, Sep. 2006, pp. 4317-4336.

Tillack, et al.: "Selection of Nickel, Nickel-Copper, Nickel-Cromium, and Nickel-Chromium-Iron Allows", AMS Handbook, Welding, Brazing and Soldering, vol. 6, Dec. 1, 1993 (Dec. 1, 1993) pp. 586-592, XP008097120, p. 589.

Titanium-Boron (TiB) Phase Diagram [online], [retrieved on Jan. 27, 2015]. Retrieved from the internet:<URL:http://www.calphad.com/titaniumboron.html>.

Chen et al.: "Characterization of Microstructure and Mechanical Properties of High Chromium Cast Irons Using SEM and Nanoindentation," JMEPEG 2015 (published online Oct. 30, 2014), vol. 24(1), pp. 98-105.

Yoo et al.: "The effect of boron on the wear behavior of iron-based hardfacing alloys for nuclear power plants valves," Journal of Nuclear Materials 352 (2006) 90-96.

International Preliminary Report on Patentability re PCT Application No. PCT/US2015/034702, dated Dec. 15, 2016.

* cited by examiner

US 11,130,205 B2

CRACK RESISTANT HARDFACING ALLOYS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND

Field

The disclosure generally relates to hardfacing weld overlays used to protect components subject to abrasion

Description of the Related Art

Hardfacing and/or weld overlays are commonly used in a variety of applications to protect components from excessive material loss in abrasive environments. In certain applications it can be desirable for the hardfacing overlay to remain crack free after the welding process is complete. This is not typical of hardfacing alloys as many stress relieve crack during or immediately after welding due to the inherent low toughness of the alloy. Hardfacing alloys are typically very hard, in excess of 50 HRC, and it is well known by those skilled in the art of metallurgy that hardness is generally inversely related to toughness. In certain applications, it is further desirable to weld over the original worn down layer of the hardfacing, and to do so without generating cracks in the original or secondary weld overlay. In such applications it is often desirable to continuously weld over worn layers again and again as wear occurs on the existing hardfacing to continuously repair and re-build the hardfacing layer. In the process of re-building hardfacing layers in this manner, it is commonplace to weld a hardfacing alloy of one type over a hardfacing layer of a second different type. It is generally desirable to do be able to do so without introducing any loss in performance.

Two types of cracks are known to commonly occur in hardfacing. The first, stress cracks, are very common and easy to detect. These cracks occur due to the weld bead contracting as it cools, resulting in thermal stresses being built up in the weld to a level which creates cracks in the weld. The second, hot tears, are less common, and less detectable as they do not create loud crack 'ping's during the welding process. Hot tears occur when the alloy solidifies over a larger temperature, and the edges of the bead begin to solidify and contract while the center of the bead has not yet fully solidified. The contraction of the outer bead pulls the liquid phase at the center of the bead apart. This mechanism is also known to those skilled in the art of metallurgy.

An example of a specific application where the problems of stress cracking and hot tearing commonly occur is hardbanding. Hardbanding is the process of protecting the drill pipe, generally in the form of two or more weld beads deposited onto the tool joint. It is common and also desirable to deposit additional overlays onto worn hardbands to rebuild the wear resistant surface. As drill pipe is commonly rented out to various drilling sites, and it is also common to apply one type of hardbanding alloy over a second hardbanding alloy of a different type. The current available selection of hardbanding alloys is relatively diverse; many form wear resistance through the carbide formation, and many others through boride formation. Welding a carbide forming alloy over a boride forming alloy creates conditions where the re-building layer is very likely to either stress crack or hot tear.

One example of an alloy which is highly resistant to hot tearing, but is subject to stress cracking is presented in U.S. Pat. No. 8,647,449: Fe: bal, Cr: 5, Nb: 4, V: 0.5, C: 0.8, B: 0.9, Mo: 3.5, Ti: 0.2, Si: 0.5, Mn: 1, hereby incorporated by reference in its entirety. This alloy can be welded as a single layer, but is increasingly likely to stress crack with subsequent re-building layers. The general class of materials which exhibit this type of behavior can form either primary carbides or borides, and also form eutectic carbides or borides in excess of 15 volume %. This classification is based upon extensive research conducted within this study. An example of such an alloy is shown in FIG. 1 (left), where the both carbides [101] and borides [102] exist in a ferritic matrix [103], but the eutectic borides are present at about 20 volume %.

One example of an alloy which is highly resistant to stress cracking, but subject to hot tearing is that presented in WO 2014/127062 (which claims priority to U.S. 61/889,548, filed Nov. 4, 2013): Fe: bal, C: 1, Cr: 5, Mn: 1.1, Mo: 0.75, Ni: 0.1, Si: 0.77, Ti: 3; WO 2014/127062 and U.S. 61/889, 548 are hereby incorporated by reference in its entirety. This alloy can be re-built over worn layers of a similar type indefinitely without stress cracking or hot tearing. However, when this alloy is welded over a worn hardbanding layer containing B, it will hot tear. The general class of materials which exhibit this type of behavior form either primary carbides or borides (carbides or borides which precipitate from the liquid prior to the austenite matrix phase), but do not form both carbide and boride. An example of an alloy susceptible to hot tearing is shown in FIG. 1 (right), where primary carbides [104] are embedded in a martensitic matrix [105]; the lack of any eutectic carbides or borides, and the lack of borides in the microstructure create increased likelihood for hot tearing.

The current state of the art for hardfacing materials possess alloys which fall into either of these two general categories. Thus, there is a need for a class of hardfacing materials which are resistant to both of these forms of failure: stress cracking and hot tearing.

SUMMARY

In some embodiments, computational metallurgy can be used to explore alloy compositional ranges where several thermodynamic criteria are met: 1) the total grain boundary carbide/boride fraction can be less than 15 volume % (or less than about 15 volume %) in the undiluted state, 2) the grain boundary carbide/boride formation temperature can be no less than 80K (or no less than about 80K) below the liquidus temperature of the matrix phase in the undiluted and diluted state, 3) the minimum C level in the matrix can be greater than 0.6 weight % (or greater than about 0.6 weight %), 4) the alloy can contain both C and B. When this set of thermodynamic criteria are met, the resultant alloy can be highly resistant to stress cracking and hot tearing. The microstructure can possess a primarily martensitic matrix with both carbide and boride precipitates with the eutectic carbides and/or borides not being present in excess of 15 volume %. The utility of such a material can be a hardfacing alloy which is highly wear resistant, and can be deposited crack free as a single layer and as a rebuilding layer over itself, over carbon containing hardfacing materials, and over boron containing hardfacing materials without stress cracking or hot tearing.

Disclosed herein are embodiments of an article of manufacture which can be used as a feedstock for hardfacing weld overlay whereby the article comprises a macro-hardness of 50 HRC or greater and a high resistance to stress cracking and hot tearing when welded as a single layer or over a worn existing hardfacing layer, wherein a worn hardfacing layer is characterized by any alloy which contains a total sum of carbon and/or boron up to 3 weight %.

In some embodiments, the alloy can have high abrasion resistance as characterized by an ASTM G65A mass loss of less than 0.5 grams. In some embodiments, the resultant hardfacing deposit can contain both carbide and boride precipitates.

In some embodiments, the resultant hardfacing deposit can contain greater than 0 volume % grain boundary carbides and/or borides but less than 15 volume % grain boundary precipitates. In some embodiments, the resultant hardfacing deposit can contain greater than 0 volume % grain boundary carbides and/or borides but less than 15 volume % grain boundary precipitates when present a fully undiluted and a fully diluted state.

In some embodiments, the feedstock alloy or layer can comprise, in wt. %, Fe: bal, B: 0-6-0.9, C: 0.75-1.25, Cr: 14.25-26, and Nb+Ti+V: 3.5-4.5. In some embodiments, the feedstock alloy or layer can further comprise, in wt. %, Mn: about 1.1, Mo: about 1, Si: about 0.5.

Also disclosed herein are embodiments of a work piece having at least a portion of its surface covered by a layer, wherein the layer comprises a macro-hardness of 50HRC or greater, the layer containing both carbides and borides, and a volume fraction of less than 10% eutectic carbides and/or borides.

In some embodiments, the volume fraction of eutectic carbide and/or borides can be greater than 0%. In some embodiments, the microstructure can contain primary Nb and/or Ti rich carbides. In some embodiments, the microstructure can contain eutectic Cr rich borides. In some embodiments, the alloy can have high abrasion resistance as characterized by an ASTM G65A mass loss of less than 0.5 grams.

In some embodiments, the feedstock alloy or layer can comprise, in wt. %, Fe: bal, B: 0-6-0.9, C: 0.75-1.25, Cr: 14.25-26, and Nb+Ti: 3.5-4.5. In some embodiments, the feedstock alloy or layer can further comprise, in wt. %, Mn: about 1.1, Mo: about 1, Si: about 0.5.

Also disclosed herein are embodiments of a method of forming a coated workpiece comprising depositing an alloy layer on at least a portion of the workpiece wherein the alloy comprises the following thermodynamic features: less than 10 mole fraction carbides and/or borides at 1300K, at least one carbide and one boride phase at 1300K, and eutectic carbides and/or borides at no less than 80K below the liquidus temperature of the ferritic or austenitic iron matrix phase.

In some embodiments, the minimum carbon content in the liquid phase can be 0.5 wt. %. In some embodiments, the alloy can contain eutectic carbides and/or borides at no less than 80K below the liquidus temperature of the ferritic or austenitic iron matrix phase in the fully diluted state. In some embodiments, the alloy can have high abrasion resistance as characterized by an ASTM G65A mass loss of less than 0.5 grams.

In some embodiments, the feedstock alloy or layer can comprise, in wt. %, Fe: bal, B: 0-6-0.9, C: 0.75-1.25, Cr: 14.25-26, and Nb+Ti: 3.5-4.5. In some embodiments, the feedstock alloy or layer can further comprise, in wt. %, Mn: about 1.1, Mo: about 1, Si: about 0.

Disclosed herein are embodiments of a metal alloy composition, comprising an Fe-based alloy comprising alloying elements of boron, carbon, chromium, and niobium, titanium and/or vanadium, wherein the maximum eutectic carbide/boride phase fraction of the alloy is about 15 mole %, wherein the maximum grain boundary formation temperature gap of the alloy is about 80K, wherein the minimum carbon level in the liquid is about 0.5 wt. %, and wherein the alloy comprises both carbides and borides, and the carbides are thermodynamically stable at a temperature equal to or greater than about 80K below the liquid temperature of the austenite or ferrite matrix phase.

In some embodiments, the alloy can be primarily martensitic. In some embodiments, carbide and boride precipitates may not exceed about 15 volume %. In some embodiments, the alloy can be provided as a hardfacing weld overlay. In some embodiments, the alloy can be provided as a single layer onto a component. In some embodiments, the alloy can be provided as multiple layers over a worn hardfacing layer.

Also disclosed herein are embodiments of an article of manufacture for use as a feedstock for hardfacing weld overlay, wherein the article comprises an alloy having a macro-hardness of 50 HRC or greater and a high resistance to stress cracking and hot tearing when welded as a single layer or over a worn existing hardfacing layer, wherein the worn existing hardfacing layer is characterized by any alloy which contains a total sum of carbon and or boron up to 3 weight %.

In some embodiments, the alloy can have high abrasion resistance as characterized by an ASTM G65A mass loss of less than 0.5 grams. In some embodiments, a resultant hardfacing deposit of the alloy over the worn existing hardfacing layer can contain both carbide and boride precipitates. In some embodiments, a resultant hardfacing deposit of the alloy over the worn existing hardfacing layer can contain greater than 0 volume % grain boundary carbides and/or borides but less than 15 volume % grain boundary precipitates. In some embodiments, a resultant hardfacing deposit of the alloy over the worn existing hardfacing layer can contain greater than 0 volume % grain boundary carbides and/or borides but less than 15 volume % grain boundary precipitates when present a fully undiluted and a fully diluted state.

In some embodiments, the alloy can comprise Fe and, in wt. %:
  B: 0.6-0.9;
  C: 0.75-1.25;
  Cr: 14.25-26; and
  Nb+Ti+V: 3.5-4.5.

In some embodiments, the alloy can further comprise, in wt. %:
  Mn: about 1.1;
  Mo: about 1; and
  Si: about 0.5.

Also disclosed herein are embodiments of a work piece having at least a portion of its surface covered by a layer, wherein the layer comprises an alloy having a macro-hardness of 50HRC or greater, the alloy containing both carbides and borides, and wherein the alloy comprises a volume fraction of less than 10% eutectic carbides and/or borides.

In some embodiments, the volume fraction of eutectic carbide and/or borides can be greater than 0%. In some embodiments, a microstructure of the alloy can comprise primary Nb and/or Ti rich carbides. In some embodiments, a microstructure of the alloy can comprise eutectic Cr rich borides. In some embodiments, the alloy can have high abrasion resistance as characterized by an ASTM G65A mass loss of less than 0.5 grams.

In some embodiments, the alloy can comprise Fe and, in wt. %:
B: 0.6-0.9;
C: 0.75-1.25;
Cr: 14.25-26; and
Nb+Ti+V: 3.5-4.5.

In some embodiments, the alloy can further comprise, in wt. %:
Mn: about 1.1;
Mo: about 1; and
Si: about 0.5.

Also disclosed herein are embodiments of a method of forming a coated workpiece comprising depositing an alloy layer on at least a portion of the workpiece wherein the alloy layer comprises the following thermodynamic features less than 10 mole fraction carbides and/or borides at 1300K, at least one carbide and one boride phase at 1300K, and eutectic carbides and/or borides at no less than 80K below the liquidus temperature of the ferritic or austenitic iron matrix phase.

In some embodiments, a minimum carbon content in a liquid phase of the alloy layer can be 0.5 wt. %. In some embodiments, the alloy layer can comprise eutectic carbides and/or borides at no less than 80K below the liquidus temperature of a ferritic or austenitic iron matrix phase of the alloy layer in a fully diluted state. In some embodiments, the alloy layer can have high abrasion resistance as characterized by a ASTM G65A mass loss of less than 0.5 grams.

In some embodiments, the alloy layer can comprise Fe and, in wt. %:
B: about 0.1 to about 1.1;
C: about 0.6 to about 2;
Cr: about 0.5 to about 22;
Mn: about 0 to about 1.15;
Mo: about 0 to about 1;
Nb: about 0 to about 8;
Si: about 0 to about 0.65;
Ti: about 0 to about 8;
V: about 0 to about 10;
W: about 0 to about 4; and
Zr: about 0 to about 8.

In some embodiments, the alloy layer can comprise Fe and, in wt. %:
B: 0.6-0.9;
C: 0.75-1.25;
Cr: 14.25-26; and
Nb+Ti+V: 3.5-4.5.

In some embodiments, the alloy layer can further comprise, in wt. %:
Mn: about 1.1;
Mo: about 1; and
Si: about 0.5.

Other methods are also contemplated in this disclosure as well, such as hardfacing or hardbanding procedures. For example, a single, or multiple, layers of an alloy can be applied over a substrate.

Also disclosed herein are embodiments of an alloy for hardfacing over a substrate, the alloy comprising a matrix comprising at least about 10% by volume martensite, and a grain boundary carbide and/or boride volume fraction of below about 15%, where both carbides and borides are present.

In some embodiments, the alloy can have a composition of Fe and, in weight percent:
about 0.52 to about 0.9 B;
about 0.68 to about 1.25 C;
about 8.36 to about 16.1 Cr; and
about 3 to about 4.5 Nb.

Also disclosed herein are embodiments of an alloy for hardfacing over a substrate, the alloy comprising a minimum hardness of about 50 HRC, a minimum wear resistance of 0.5 g lost according to ASTM G65 Procedure A, a lack of hot tearing when welded as a hardfacing alloy on a substrate containing carbon and/or boron, and a lack of stress cracking when welded on the substrate containing carbon and/or boron.

In some embodiments, the alloy can further comprise a matrix comprising at least about 10% by volume martensite, and a grain boundary carbide and/or boride volume fraction of below about 15%, where both carbides and borides are present.

In some embodiments, the alloy can have a composition of Fe and, in weight percent:
about 0.52 to about 0.9 B;
about 0.68 to about 1.25 C;
about 8.36 to about 16.1 Cr; and
about 3 to about 4.5 Nb.

In some embodiments, the maximum eutectic carbide/boride phase fraction of the alloy can be about 15 mole %, wherein the maximum grain boundary formation temperature gap of the alloy can be about 80K, wherein the minimum carbon level in the liquid can be about 0.5 wt. %, and wherein the alloy can comprise both carbides and borides, and the carbides can be thermodynamically stable at a temperature equal to or greater than about 80K below the liquid temperature of the austenite or ferrite matrix phase.

DETAILED DESCRIPTION

Figure 1:
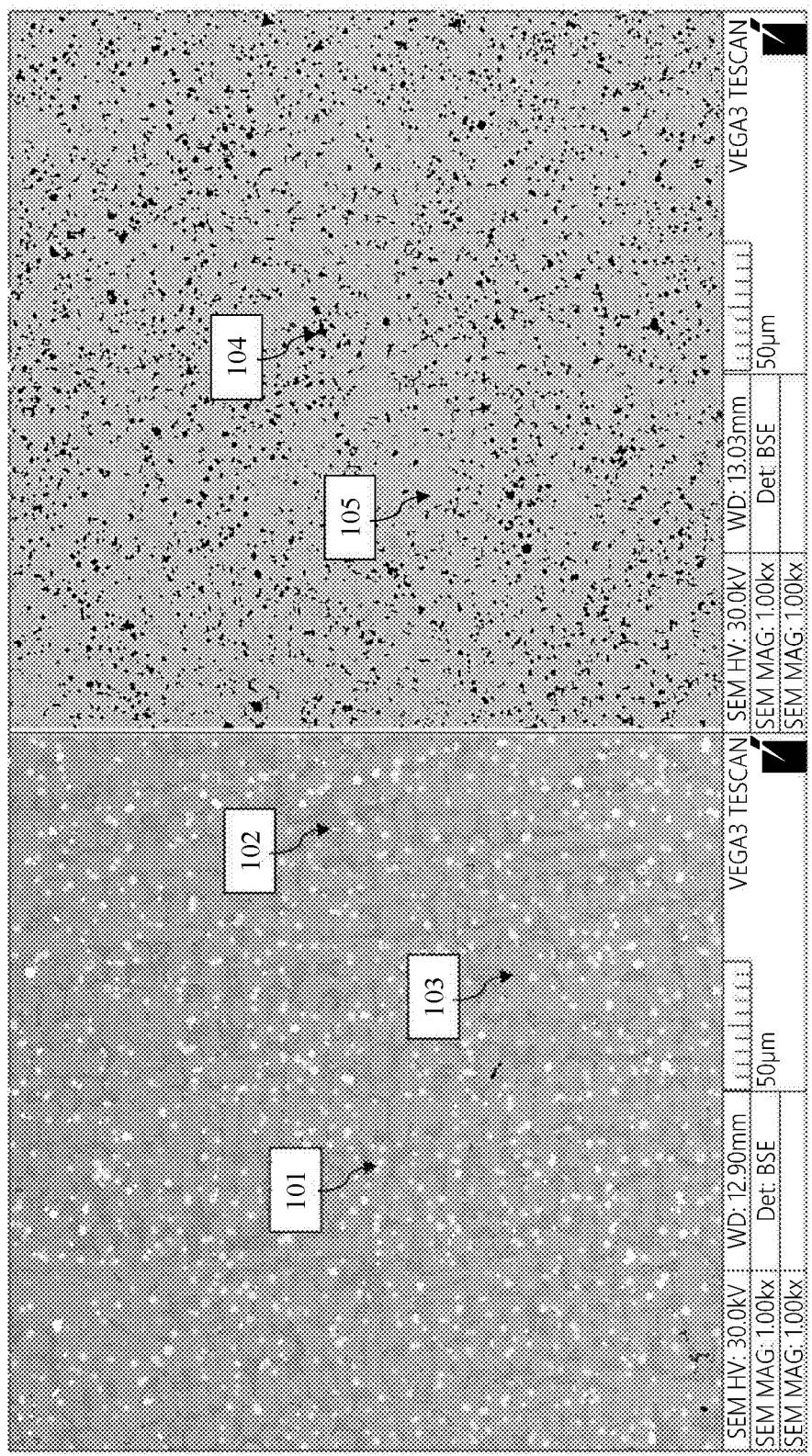
FIG. 1 illustrates an example of microstructures of hardfacing alloys susceptible to stress cracking (left) and hot tearing (right).

Disclosed herein are embodiments of crack resistant alloys, and methods of manufacturing the alloys, which can be used in particular for hardfacing applications. In some embodiments, computational metallurgy can be used to explore alloy compositional ranges which can achieve certain parameters, discussed in detail below.

Metal Alloy Composition

It has been determined through thermodynamic analysis and experimentation that alloying elements (to be added to an Fe-based composition) which can be used for ensuring the microstructural and performance criteria specified in certain embodiments of this disclosure are B, C, Cr, Nb, and Ti. In addition to these alloying elements, secondary alloying elements can be added to further enhance the performance, such as Al, Si, V, Mn, Ni, Cu, Zr, and W among others. In addition, typical impurities such as S, P, and others, can be present in the manufactured form of these alloys.

Embodiments of this alloy can describe a unique class of alloys which possess the disclosed microstructural features and exhibit the disclosed performance criteria when welded as a single layer onto a component (diluted), when welded multiple times over worn hardfacing layers (undiluted, typically requiring 4 or more re-building layers), as well as any intermediate layer chemistries produced during reapplications. Dilution can occur in a weld as some of the base material (e.g., the substrate that the weld is being applied to), can infiltrate the weld itself during the welding operation, thus diluting the weld composition with the composition of the substrate. Thus, for every layer that is added on, dilution can be reduced as the weld is no longer in direct contact with the base material, but instead is in contact with other diluted or undiluted welds. Thus, in some examples the first layer could be a diluted layer, while layers 2-3 could be intermediate layers, and a fourth layer could be an undiluted layer, though which layer is which can depend on the chemistry of the welds and the substrate.

In some embodiments, the diluted chemistry can contain about 5-30% (or about 5 to about 30%) by weight the chemistry of the base material mixed with the remainder chemistry of the feedstock. During subsequent re-applications of the hardfacing alloy over worn layers, the chemistry of the re-applied layer can be increasingly enriched until it approaches the chemistry of the weld feedstock. The compositions described herein can refer to the feedstock composition, the diluted composition of a single layer weld, the undiluted composition of a weld layer produced from multiple reapplications as well as any intermediate weld layer compositions ranging from the fully diluted state to the fully undiluted state.

In some embodiments, the alloy can be described by a composition in weight percent comprising the following elemental ranges which have been produced and evaluated experimentally and which met the disclosed microstructural criteria:
  Fe: Balance
  B: 0.6 to 0.9 (or about 0.6 to about 0.9)
  C: 0.75 to 1.25 (or about 0.75 to about 1.25)
  Cr: 14.25 (or about 14.25)
  Nb: 3.5 to 4.5 (or about 3.5 to about 4.5)
Further elements which can be added, primarily for manufacturability and processing control, are:
  Mn: 1.1 (or about 1.1)
  Mo: 1 (or about 1)
  Si: 0.5 (or about 0.5)
  Ti: 0.5 (or about 0.5)
  V 0.5 (or about 0.5)

In some embodiments, the alloy can be described by a compositions in weight percent comprising the following elemental ranges including those evaluated experimentally and using thermodynamic modeling tools:
  Fe: Balance
  B: 0.6 to 0.9 (or about 0.6 to about 0.9)
  C: 0.75 to 1.25 (or about 0.75 to about 1.25)
  Cr: 14.25 to 26 (or about 14.25 to about 26)
  Nb: 3.5 to 4.5 (or about 3.5 to about 4.5)
Further elements which can be added, primarily for manufacturability and processing control, are:
  Mn: 1.1 (or about 1.1)
  Mo: 1 (or about 1)
  Si: 0.5 (or about 0.5)
  Ti: 0.5 (or about 0.5)
  V 0.5 (or about 0.5)

In some embodiments, the Nb content in the alloy can be exchanged fully or partially with Ti and/or V as both form primary carbides in alloys of this type. In some embodiments, the Nb+Ti+V concentration in weight % of the disclosed alloys can be between 3.5 and 4.5 (or between about 3.5 and about 4.5). In some embodiments, the Nb+Ti concentration in weight % can be between 3.5 and 4.5 (or between about 3.5 and about 4.5).

In some embodiments, the alloy can be described by specific compositions in weight percent comprising the following elements, which have been produced and evaluated experimentally and which met the disclosed microstructural and performance criteria:
  Fe: Balance
  B: 0.75 (or about 0.75)
  C: 0.75 to 0.95 (or about 0.75 to about 0.95)
  Cr: 14.25 (or about 14.25)
  Nb: 3.5 (or about 3.5)
Further elements which can be added, primarily for manufacturability and processing control, are:
  Mn: 1.1 (or about 1.1)
  Mo: 1 (or about 1)
  Si: 0.5 (or about 0.5)
  Ti: 0.5 (or about 0.5)
  V 0.5 (or about 0.5)

In some embodiments, the alloy can be described by specific compositions in weight percent comprising the following elemental ranges as defined through glow discharge spectrometer readings, which have been produced and evaluated experimentally and which met the disclosed microstructural and performance criteria:
  Fe: Balance
  B: 0.52 to 0.75 (or about 0.52 to about 0.75)
  C: 0.68 to 1.1 (or about 0.68 to about 1.1)
  Cr: 8.36 to 16.1 (or about 8.36 to about 16.1)
  Nb: 3 to 4 (or about 3 to about 4)
Further elements which can be added primarily for manufacturability and processing control are:
  Mn: 1.05 to 1.1, Mo: 0.85 to 1.02, Si: 0.52 to 0.59, Ti: 0.39 to 0.85, and V: 0.39 to 0.46; or
  Mn: about 1.05 to about 1.1, Mo: about 0.85 to about 1.02, Si: about 0.52 to about 0.59, Ti: about 0.39 to about 0.85, and V: about 0.38 to about 0.46

In some embodiments, the alloy can be described by specific compositions in weight percent comprising the following elemental ranges as defined through glow discharge spectrometer readings, which have been produced and evaluated experimentally and which met the disclosed microstructural and performance criteria:
  Fe: Balance
  B: 0.52 to 0.9 (or about 0.52 to about 0.9)
  C: 0.68 to 1.25 (or about 0.68 to about 1.25)
  Cr: 8.36 to 26 (or about 8.36 to about 16.1)
  Nb: 3 to 4.5 (or about 3 to about 4.5)
Further elements which can be added primarily for manufacturability and processing control are:
  Mn: 1.05 to 1.1, Mo: 0.85 to 1.02, Si: 0.52 to 0.59, Ti: 0.39 to 0.85, and V: 0.39 to 0.46; or
  Mn: about 1.05 to about 1.1, Mo: about 0.85 to about 1.02, Si: about 0.52 to about 0.59, Ti: about 0.39 to about 0.85, and V: about 0.38 to about 0.46

In some embodiments, the alloy can be described by compositional ranges which meet the thermodynamic criteria described in this disclosure. These alloys can comprise the following:
  Fe: Balance
  B: 0.1 to 1.1 (or about 0.1 to about 1.1)

C: 0.6 to 2 (or about 0.6 to about 2)
Cr: 0.5 to 22 (or about 0.5 to about 22)
Mn: 0 to 1.15 (or about 0 to about 1.15)
Mo: 0 to 1 (or about 0 to about 1)
Nb: 0 to 8 (or about 0 to about 8)
Si: 0 to 0.65 (or about 0 to about 0.65)
Ti: 0 to 8 (or about 0 to about 8)
V: 0 to 10 (or about 0 to about 10)
W: 0 to 4 (or about 0 to about 4)
Zr: 0 to 8 (or about 0 to about 8)

Further elements which can be added primarily for manufacturability and processing control are:
- Mn: 1.05 to 1.1, Mo: 0.85 to 1.02, Si: 0.52 to 0.59, Ti: 0.39 to 0.85, and V: 0.39 to 0.46; or
- Mn: about 1.05 to about 1.1, Mo: about 0.85 to about 1.02, Si: about 0.52 to about 0.59, Ti: about 0.39 to about 0.85, and V: about 0.38 to about 0.46

In some embodiments, the alloy can be described by the specific exemplary compositions which met either the performance and/or microstructural criteria, comprising a mixture of one or more of the following (in all cases Fe forming the balance):

B: 0.6, C: 1, Cr: 14.25, Mn: 1.1, Mo: 1, Nb: 4.5, Si: 0.5, Ti: 0.5, and V: 0.5 (or B: about 0.6, C: about 1, Cr: about 14.25, Mn: about 1.1, Mo: about 1, Nb: about 4.5, Si: about 0.5, Ti: about 0.5, and V: about 0.5)

B: 0.9, C: 1.1, Cr: 14.25, Mn: 1.1, Mo: 1, Nb: 3.5, Si: 0.5, Ti: 0.5, and V: 0.5 (or B: about 0.9, C: about 1.1, Cr: about 14.25, Mn: about 1.1, Mo: about 1, Nb: about 3.5, Si: about 0.5, Ti: about 0.5, and V: about 0.5)

B: 0.75, C: 1.05, Cr: 14.25, Mn: 1.1, Mo: 1, Nb: 3.5, Si: 0.5, Ti: 0.5, and V: 0.5 (or B: about 0.75, C: about 1.05, Cr: about 14.25, Mn: about 1.1, Mo: about 1, Nb: about 3.5, Si: about 0.5, Ti: about 0.5, and V: about 0.5)

B: 0.6, C: 1, Cr: 14.25, Mn: 1.1, Mo: 1, Nb: 4.5, Si: 0.5, Ti: 0.5, and V: 0.5 (or B: about 0.6, C: about 1, Cr: about 14.25, Mn: about 1.1, Mo: about 1, Nb: about 4.5, Si: about 0.5, Ti: about 0.5, and V: about 0.5)

B: 0.75, C: 1.05, Cr: 14.25, Mn: 1.1, Mo: 1, Nb: 3.5, Si: 0.5, Ti: 0.5, and V: 0.5 (or B: about 0.75, C: about 1.05, Cr: about 14.25, Mn: about 1.1, Mo: about 1, Nb: about 3.5, Si: about 0.5, Ti: about 0.5, and V: about 0.5)

B: 0.75, C: 1.25, Cr: 14.25, Mn: 1.1, Mo: 1, Nb: 3.5, Si: 0.5, Ti: 0.5, and V: 0.5 (or B: about 0.75, C: about 1.25, Cr: about 14.25, Mn: about 1.1, Mo: about 1, Nb: about 3.5, Si: about 0.5, Ti: about 0.5, and V: about 0.5)

B: 0.75, C: 0.95, Cr: 14.25, Mn: 1.1, Mo: 1, Nb: 3.5, Si: 0.5, Ti: 0.5, and V: 0.5 (or B: about 0.75, C: about 0.95, Cr: about 14.25, Mn: about 1.1, Mo: about 1, Nb: about 3.5, Si: about 0.5, Ti: about 0.5, and V: about 0.)

B: 0.75, C: 0.85, Cr: 14.25, Mn: 1.1, Mo: 1, Nb: 3.5, Si: 0.5, Ti: 0.5, and V: 0.5 (B: about 0.75, C: about 0.85, Cr: about 14.25, Mn: about 1.1, Mo: about 1, Nb: about 3.5, Si: about 0.5, Ti: about 0.5, and V: about 0.5)

B: 0.75, C: 0.75, Cr: 14.25, Mn: 1.1, Mo: 1, Nb: 3.5, Si: 0.5, Ti: 0.5, and V: 0.5 (or B: about 0.75, C: about 0.75, Cr: about 14.25, Mn: about 1.1, Mo: about 1, Nb: about 3.5, Si: about 0.5, Ti: about 0.5, and V: about 0.5)

The Fe content identified in all of the compositions described in the above paragraphs may be the balance of the composition as indicated above, or alternatively, the balance of the composition may comprise Fe and other elements. In some embodiments, the balance may consist essentially of Fe and may include incidental impurities.

Table 1 below illustrates a listing of some alloys compositions produced using embodiments of the above-described compositions.

TABLE 1

Alloys Compositions Produced into Experimental Ingots and Welding Wires

| ALLOY | B | C | Cr | Mn | Mo | Nb | Si | Ti | V |
|---|---|---|---|---|---|---|---|---|---|
| 1 | 1.45 | 0.91 | 4.82 | 1.01 | 3.22 | 4.54 | 0.59 | 0.39 | 0.54 |
| 2 | 1.6 | 0.85 | 3 | 1.2 | 2 | 3 | 0.4 | 0.5 | 0.5 |
| 3 | 1.45 | 0.91 | 2 | 1.01 | 3.22 | 4.54 | 0.59 | 0.39 | 0.54 |
| 4 | 1.45 | 0.91 | 2 | 1.01 | 5 | 4.54 | 0.59 | 0.39 | 0.54 |
| 5 | 1.45 | 0.91 | 2 | 2 | 5 | 4.54 | 0.59 | 0.39 | 0.54 |
| 6 | 1.45 | 0.91 | 4.82 | 1.01 | 3.22 | 3 | 0.59 | 0.39 | 0.54 |
| 7 | 1.45 | 0.91 | 4.82 | 1.01 | 3.22 | 4 | 0.59 | 0.39 | 0.54 |
| 8 | 1.45 | 0.91 | 4.82 | 1.01 | 3.22 | 6 | 0.59 | 0.39 | 0.54 |
| 9 | 1.45 | 0.91 | 4.82 | 1.01 | 3.22 | 6 | 0.59 | 1 | 0.54 |
| 10 | 1.45 | 0.91 | 4.82 | 1.01 | 3.22 | 6 | 0.59 | 1 | 2 |
| 11 | 1.45 | 0.91 | 4.82 | 1.01 | 3.22 | 4.5 | 0.59 | 1 | 0.54 |
| 12 | 1.45 | 0.91 | 4.82 | 1.01 | 3.22 | 4.5 | 0.59 | 0.75 | 0.54 |
| 13 | 1.45 | 0.91 | 4.82 | 1.01 | 3.22 | 4.5 | 0.59 | 1.25 | 0.54 |
| 14 | 1.45 | 0.91 | 4.82 | 1.01 | 3.22 | 4.5 | 0.59 | 0.6 | 0.54 |
| 15 | 1.6 | 0.85 | 3 | 1.2 | 2 | 3 | 0.4 | 1 | 0.5 |
| 16 | 1.45 | 0.85 | 3 | 1.2 | 2 | 3 | 0.4 | 1 | 0.5 |
| 17 | 1.45 | 0.91 | 4.82 | 1.01 | 3.22 | 6 | 0.59 | 1 | 0.54 |
| 18 | 1.45 | 0.91 | 4.82 | 1.01 | 3.22 | 4.54 | 0.59 | 1 | 0.54 |
| 19 | 2.5 | 0.91 | 4.82 | 1.01 | 3.22 | 4.54 | 0.59 | 1 | 0.54 |
| 20 | 1.45 | 0.94 | 5.5 | 1.31 | 3.08 | 4 | 0.53 | 0.6 | 0.53 |
| 21 | 1.45 | 0.94 | 5.5 | 1.31 | 3.08 | 3.5 | 0.53 | 0.6 | 0.53 |
| 22 | 1.45 | 0.94 | 5.5 | 1.31 | 3.08 | 3 | 0.53 | 0.6 | 0.53 |
| 23 | 1.45 | 0.94 | 5.5 | 1.31 | 3.08 | 2 | 0.53 | 0.6 | 0.53 |
| 24 | 1.75 | 0.85 | 5 | 1 | 3 | 4 | 0.4 | 0.25 | 0.5 |
| 25 | 2.5 | 0.85 | 5 | 1 | 3 | 4 | 0.4 | 0.25 | 0.5 |
| 26 | 2.5 | 0.85 | 5 | 1 | 1 | 4 | 0.4 | 0.25 | 0.5 |
| 27 | 2.5 | 0.85 | 5 | 0 | 0 | 4 | 0.4 | 0.25 | 0.5 |
| 28 | 2.5 | 0.85 | 5 | 0 | 0 | 4 | 0.4 | 0.25 | 0.5 |
| 29 | 2.8 | 0.8 | 6.5 | 0 | 0 | 3.7 | 0 | 0.25 | 0 |
| 30 | 2.5 | 0.9 | 5 | 1 | 1 | 4 | 0.4 | 0.4 | 0.5 |
| 31 | 2 | 0.9 | 5 | 1 | 1 | 4 | 0.4 | 0.4 | 0.5 |
| 32 | 1.75 | 0.9 | 5 | 1 | 1 | 4 | 0.4 | 0.4 | 0.5 |
| 33 | 1.5 | 0.9 | 5 | 1 | 1 | 4 | 0.4 | 0.4 | 0.5 |
| 34 | 1 | 0.9 | 5 | 1 | 1 | 4 | 0.4 | 0.4 | 0.5 |
| 35 | 1.5 | 1.13 | 5 | 1 | 1 | 5.81 | 0.4 | 0.4 | 0.5 |
| 36 | 1.07 | 1.13 | 5 | 1 | 1 | 5.71 | 0.4 | 0.4 | 0.5 |
| 37 | 0.65 | 1.33 | 5 | 1 | 1 | 5.66 | 0.4 | 1.3 | 0.5 |
| 38 | 0.64 | 1.32 | 5 | 1 | 1 | 7.36 | 0.4 | 0.4 | 0.5 |
| 39 | 0.65 | 1.5 | 5 | 1 | 1 | 5 | 0.4 | 1 | 0.5 |
| 40 | 0.5 | 2 | 5 | 1 | 1 | 5 | 0.4 | 1 | 0.5 |
| 41 | 0.5 | 1.5 | 5 | 1 | 1 | 5 | 0.4 | 1 | 0.5 |
| 42 | 0.25 | 1.5 | 5 | 1 | 1 | 5 | 0.4 | 1 | 0.5 |
| 43 | 0 | 1.5 | 5 | 1 | 1 | 5 | 0.4 | 1 | 0.5 |
| 44 | 1.1 | 0.65 | 0.5 | 0.7 | 1 | 3.5 | 0.5 | 2.5 | 0.5 |
| 45 | 1.1 | 0.65 | 1.5 | 0.7 | 1 | 2.5 | 0.5 | 2.5 | 0.5 |
| 46 | 1.1 | 0.65 | 3 | 0.7 | 1 | 2.5 | 0.5 | 2 | 0.5 |
| 47 | 1.1 | 0.65 | 3 | 0.7 | 0.35 | 2.5 | 0.5 | 2 | 0.07 |
| 48 | 0.8 | 0.95 | 1 | 0.7 | 1 | 3.5 | 0.5 | 2.5 | 0.5 |
| 49 | 0.8 | 0.95 | 0.5 | 0.7 | 1 | 3 | 0.5 | 2.5 | 0.5 |
| 50 | 0.8 | 0.95 | 0.5 | 0.7 | 1 | 4 | 0.5 | 2 | 0.5 |
| 51 | 0.8 | 0.95 | 2 | 0.7 | 1 | 3 | 0.5 | 2.5 | 0.5 |
| 52 | 0.8 | 0.95 | 0.5 | 1 | 1 | 1 | 0.5 | 2 | 0.5 |
| 53 | 0.8 | 0.95 | 0.5 | 1 | 1 | 1.5 | 0.5 | 1 | 0.5 |
| 54 | 0.2 | 1.5 | 0.5 | 0.78 | 0.68 | 2.67 | 0.44 | 0.45 | 0.36 |
| 55 | 0.2 | 2.3 | 0.5 | 0.75 | 0.7 | 5 | 0.44 | 3 | 0.36 |
| 56 | 0.2 | 2.1 | 0.5 | 0.75 | 0.7 | 5 | 0.44 | 3 | 0.36 |
| 57 | 0.2 | 1.8 | 0.5 | 0.75 | 0.7 | 5 | 0.44 | 3 | 0.36 |
| 58 | 0.2 | 1.6 | 0.5 | 0.75 | 0.7 | 5 | 0.44 | 3 | 0.36 |
| 59 | 0.3 | 1.25 | 0.75 | 1.1 | 1 | 3.8 | 0.65 | 0.65 | 0.5 |
| 60 | 0.3 | 1.15 | 0.75 | 1.1 | 1 | 3.8 | 0.65 | 0.65 | 0.5 |
| 61 | 0.3 | 0.95 | 0.75 | 1.1 | 1 | 3.8 | 0.65 | 0.65 | 0.5 |
| 62 | 0.3 | 1.75 | 1.75 | 1 | 1 | 3 | 0.6 | 0.6 | 0.5 |
| 63 | 0.3 | 1.1 | 1.75 | 1 | 1 | 3 | 0.6 | 0.6 | 0.5 |
| 64 | 0 | 1.2 | 5 | 1 | 1 | 3 | 0.65 | 0.65 | 0.5 |
| 65 | 0.1 | 1.2 | 5 | 1 | 1 | 3 | 0.65 | 1.3 | 0.5 |
| 66 | 0.1 | 1.4 | 5 | 1 | 1 | 3 | 0.65 | 0.65 | 0.5 |
| 67 | 0.1 | 1.4 | 5 | 1 | 1 | 3 | 0.65 | 1.3 | 0.5 |
| 68 | 0.1 | 1.1 | 3.5 | 0.75 | 0.75 | 2.75 | 0.5 | 0.5 | 0.5 |
| 69 | 0.4 | 1.3 | 3.5 | 0.75 | 0.75 | 2.75 | 0.5 | 0.5 | 0.5 |
| 70 | 1.25 | 0.95 | 5.88 | 1.16 | 1 | 4 | 0.55 | 0.44 | 0.56 |

TABLE 1-continued

Alloys Compositions Produced into Experimental Ingots and Welding Wires

| ALLOY | B    | C    | Cr    | Mn  | Mo | Nb  | Si   | Ti   | V   |
|-------|------|------|-------|-----|----|-----|------|------|-----|
| 71    | 0.4  | 1.35 | 7     | 1.1 | 1  | 3.5 | 0.5  | 0.5  | 0.5 |
| 72    | 0.1  | 1.35 | 7     | 1.1 | 1  | 3.5 | 0.5  | 0.65 | 0.5 |
| 73    | 0    | 1.6  | 5     | 1   | 1  | 5.7 | 0.65 | 0    | 0   |
| 74    | 0    | 1.85 | 5     | 1   | 1  | 5.7 | 0.65 | 0    | 0   |
| 75    | 0.6  | 1    | 14.25 | 1.1 | 1  | 4.5 | 0.5  | 0.5  | 0.5 |
| 76    | 0.9  | 1.1  | 14.25 | 1.1 | 1  | 3.5 | 0.5  | 0.5  | 0.5 |
| 77    | 0.75 | 1.05 | 14.25 | 1.1 | 1  | 3.5 | 0.5  | 0.5  | 0.5 |
| 79    | 0.6  | 1    | 14.25 | 1.1 | 1  | 4.5 | 0.5  | 0.5  | 0.5 |
| 80    | 0.9  | 1.1  | 14.25 | 1.1 | 1  | 3.5 | 0.5  | 0.5  | 0.5 |
| 81    | 0.75 | 1.05 | 14.25 | 1.1 | 1  | 3.5 | 0.5  | 0.5  | 0.5 |
| 82    | 0.75 | 1.25 | 14.25 | 1.1 | 1  | 3.5 | 0.5  | 0.5  | 0.5 |
| 84    | 0.75 | 0.95 | 14.25 | 1.1 | 1  | 3.5 | 0.5  | 0.5  | 0.5 |
| 85    | 0.75 | 0.85 | 14.25 | 1.1 | 1  | 3.5 | 0.5  | 0.5  | 0.5 |
| 86    | 0.75 | 0.75 | 14.25 | 1.1 | 1  | 3.5 | 0.5  | 0.5  | 0.5 |

Thermodynamic Criteria

In some embodiments, the alloy can be fully described by thermodynamic models. Four thermodynamic modeling criteria can be used to define the alloys: 1) the maximum eutectic carbide/boride phase fraction, 2) the minimum temperature gap between the liquidus temperature of the austenite and the formation temperature of the eutectic carbide/boride phase, 3) the minimum level of C in liquid, and 4) the presence of both carbides and borides at a temperature no less than 80K below the liquidus temperature of the austenite or ferrite matrix phase.

The first thermodynamic criterion can be the maximum eutectic carbide and/or boride phase fraction. This criterion is related to the tendency for a hardfacing alloy to stress crack. As the phase fraction of the sum of any eutectic carbides and borides increases, the tendency for stress cracking can increase. The maximum limit for eutectic carbides/borides before stress cracking occurs has been determined experimentally to be 15 volume % (or about 15 volume %). Eutectic carbides/borides are defined as any carbide or boride phase which forms at a temperature equivalent to or below the liquidus temperature of the austenite. The eutectic carbide/boride phase fraction is defined as the sum total of carbides and borides which exist at 1300K (or about 1300K), which have a formation temperature at or below the liquidus temperature of the austenite. In some embodiments, the maximum eutectic carbide/boride phase fraction can be 15 mole % (or about 15 mole %). In some embodiments, the maximum eutectic carbide/boride phase fraction can be 10 mole % (or about 10 mole %). In some embodiments, the maximum eutectic carbide/boride phase fraction can be 5 mole % (or about 5 mole %).

The eutectic mole fraction will typically be highest in the un-diluted state, when the weld is re-applied over worn versions of itself at least 3 successive times. In some embodiments, this first described thermodynamic criterion can be met for a hardfacing alloy in the un-diluted state. The solidification diagram for one embodiment, Alloy 86, is shown in FIG. 1 for the undiluted state. As shown the total eutectic boride mole fraction ($Cr_2B+Fe,Mo_3B_2$) [102] is below 15%, and is at 14.2%.

The second thermodynamic criterion can be the grain boundary formation temperature gap. This criterion relates to the tendency of the alloy to hot tear. As the temperature gap increases, the tendency to hot tear can increase. It has been determined using experimental measurements that it may be advantageous if the temperature gap does not exceed 80K (or about 80K), which can thereby avoid hot tearing of the hardfacing material. The grain boundary formation temperature gap is defined as the difference in temperature between the austenite or ferrite liquidus temperature and the highest temperature at which any eutectic carbide or boride exists. In some embodiments, the maximum grain boundary formation temperature gap can be 80K (or about 80K). In some embodiments, the maximum grain boundary formation temperature gap can be 50K (or about 50K). In some embodiments, the maximum grain boundary formation temperature gap can be OK (or about OK). As shown when comparing FIG. 2 and FIG. 3, the initial solidifying matrix phase can either be ferritic or austenitic, and the grain boundary formation temperature gap is measured by using the highest formation temperature of either phase upon cooling from a liquid state.

Figure 3:
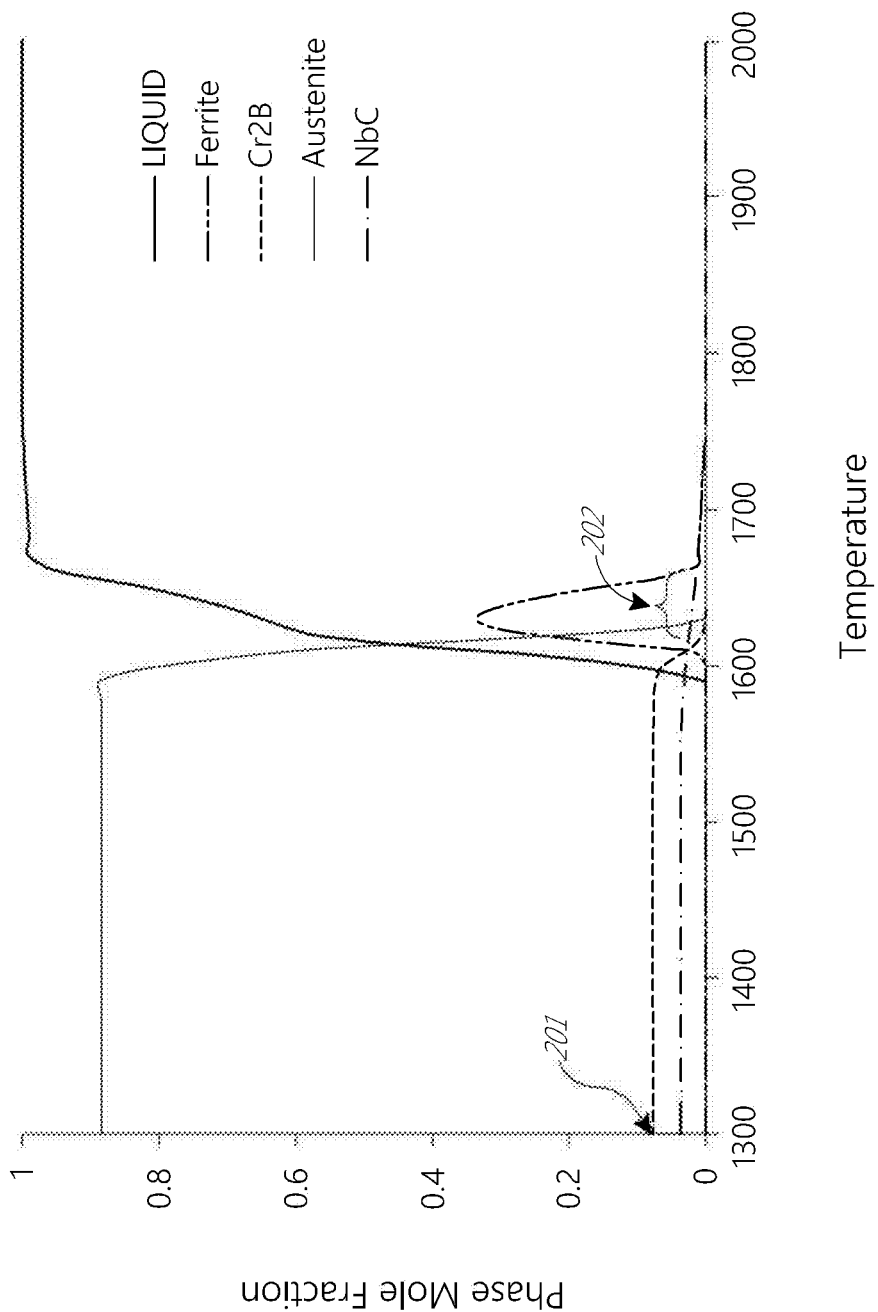
FIG. 3 illustrates a solidification diagram for an embodiment of a disclosed alloy (Alloy #86) in fully diluted composition.

The grain boundary formation temperature gap will typically be the largest in the diluted state, when the weld is applied over bare substrate material such as, for example, 41XX series or mild steels. In some embodiments, this second thermodynamic criteria can be met for the hardfacing alloy in the fully diluted state. In typical welding processes the diluted state can equate to 70% of the total alloy content of the original wire chemistry and 30% of the total alloy content of the substrate. The solidification diagram for the exemplary embodiment, Alloy 86, is shown in FIG. 3 for the diluted state, when welding over 4137 steel. As shown the grain boundary formation temperature gap [202] is 50K.

Figure 2:
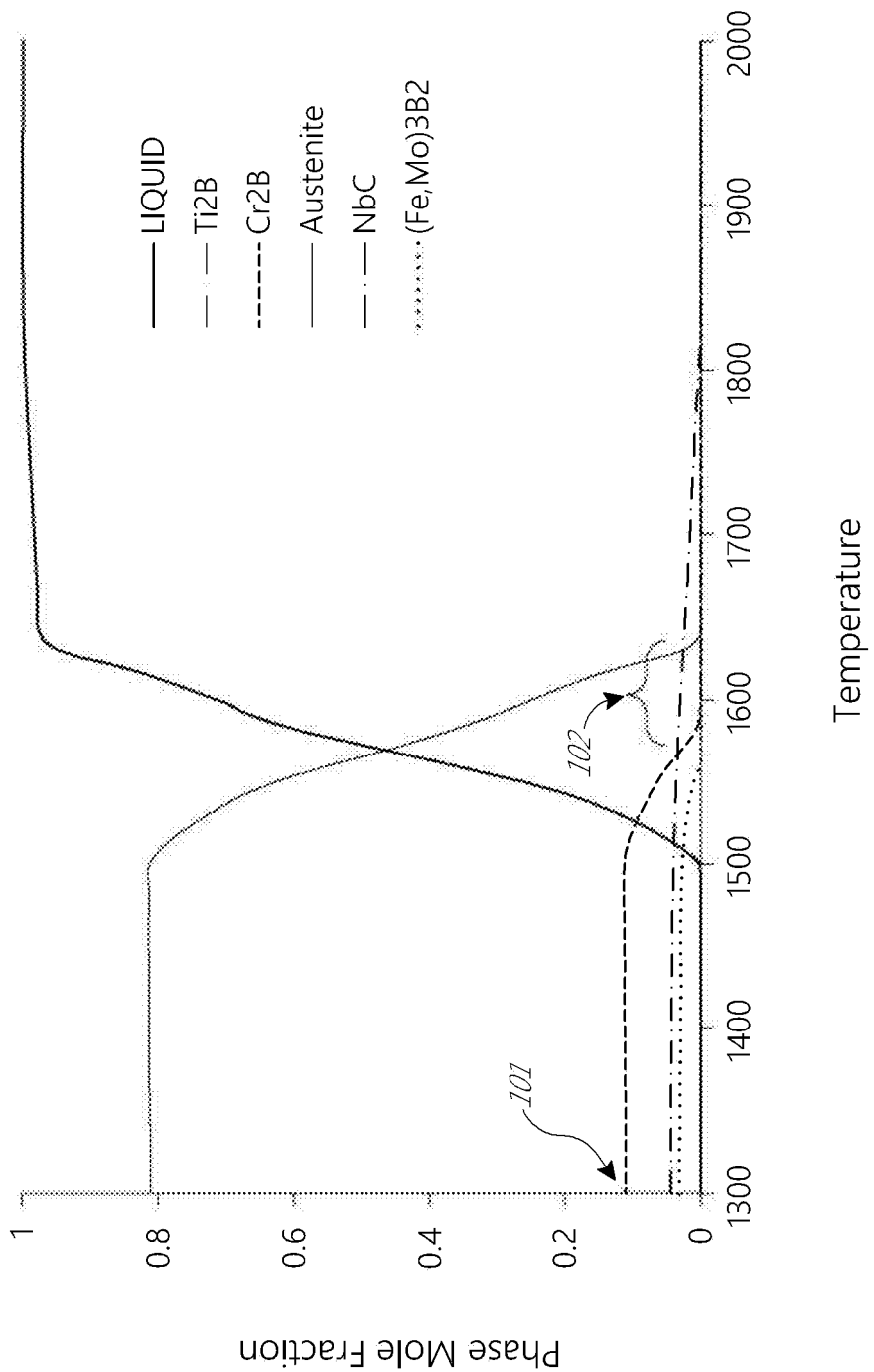
FIG. 2 illustrates a solidification diagram for an embodiment of a disclosed alloy (Alloy #86) in fully undiluted composition.

As shown in FIG. 2 and FIG. 3, the eutectic mole fraction for Alloy 86 in the fully diluted state [201] is 7.8% and the grain boundary formation temperature gap for the fully undiluted state [102] is 50K. Thus, Alloy 86 meets the thermodynamic criteria when both fully diluted and fully undiluted.

Many alloys meet either the first thermodynamic criterion or the second thermodynamic criterion but not both. Thus, computational modeling to evaluate extremely large compositional ranges can be used to design this type of material as both criteria are inversely related. Generally, as the eutectic carbide/boride phase fraction is decreased, the temperature gap is increased, and vice versa. Thus, the compositional range of alloys which simultaneously meet both these criteria is relatively narrow and not intuitive. Some hardfacing materials will not form grain boundary carbides or borides and thus do not meet criterion 2. It has been shown experimentally, that these alloys are highly susceptible to hot tearing.

The third thermodynamic criterion can be the minimum C level in the liquid. This criterion relates to the tendency for the hardfacing alloy to form significant fraction of martensite upon cooling and thus be hard and wear resistant. It has been determined experimentally that 0.5 weight % C (or about 0.5 weight % C) or greater in the liquid can create a significantly martensitic matrix under typical hardfacing deposition conditions. The minimum C level in the liquid is defined as the lowest weight fraction of carbon in the liquid over temperature span where the alloy is 100% liquid and the liquidus temperature of the austenite. However, as martensitic formation is cooling rate dependent, this criterion does not guarantee the presence of martensite in the matrix in every processing condition. In some embodiments, the minimum C level in the liquid can be 0.5 weight % (or about 0.5 weight %) or greater. In some embodiments, the minimum C level in the liquid can be 0.7 weight % (or about 0.7 weight %) or greater. In some embodiments, the minimum C level in the liquid can be 0.9 weight % (or about 0.9 weight %) or greater.

The fourth thermodynamic criteria is that the alloy can form both carbides and borides, and the carbides can be thermodynamically stable at a temperature equal to or greater than 80K (or about 80K) below the liquidus temperature of the austenite or ferrite matrix phase. This criterion relates to a hardbanding alloy's ability to be welded onto existing boron containing and/or carbon containing welds without exhibiting hot tearing or stress cracking.

Table 2 lists the thermodynamic properties for selected alloys evaluated in this disclosure. All alloys in this table meet the four thermodynamic criteria, as they all possess both carbides and borides at a temperature equal to or greater than 80K below the liquidus temperature of the austenite or ferrite matrix phase. Table 3 lists the compositions if alloys which meet the thermodynamic criteria listed in this disclosure.

TABLE 2

Table of thermodynamic properties for selected alloy compositions

| Alloy | Eutectic Mole Fraction | Grain Boundary Formation Temperature Gap | % C in Liquid |
|---|---|---|---|
| 86 - Undiluted | 12.2% | 50K | 0.51% |
| 86 - Dilute | 7.8% | 50K | 0.52% |
| M1 | 8.6% | 30K | 0.99% |
| M2 | 11.6% | 0K | 0.77% |

TABLE 3

Alloy chemistries in weight percent, balance Fe, for selected alloys evaluated using thermodynamic models which meet thermodynamic criteria

| Alloy | B | C | Cr | Mn | Mo | Nb | Si | Ti | V | W | Zr |
|---|---|---|---|---|---|---|---|---|---|---|---|
| M1 | 0.8 | 0.82 | 13.5 | 1.15 | 0.95 | 3.35 | 0.52 | 0.5 | 0.45 | 0 | 0 |
| M2 | 0.8 | 0.82 | 13.75 | 1.15 | 0.95 | 3.35 | 0.52 | 0.5 | 0.45 | 0 | 0 |
| M3 | 0.8 | 0.82 | 14 | 1.15 | 0.95 | 3.35 | 0.52 | 0.5 | 0.45 | 0 | 0 |
| M4 | 0.8 | 0.82 | 14.25 | 1.15 | 0.95 | 3.35 | 0.52 | 0.5 | 0.45 | 0 | 0 |
| M5 | 0.8 | 0.82 | 14.5 | 1.15 | 0.95 | 3.35 | 0.52 | 0.5 | 0.45 | 0 | 0 |
| M6 | 0.8 | 0.82 | 14.75 | 1.15 | 0.95 | 3.35 | 0.52 | 0.5 | 0.45 | 0 | 0 |
| M7 | 0.8 | 0.82 | 15 | 1.15 | 0.95 | 3.35 | 0.52 | 0.5 | 0.45 | 0 | 0 |
| M8 | 0.8 | 0.84 | 13.5 | 1.15 | 0.95 | 3.35 | 0.52 | 0.5 | 0.45 | 0 | 0 |
| M9 | 0.8 | 0.84 | 13.75 | 1.15 | 0.95 | 3.35 | 0.52 | 0.5 | 0.45 | 0 | 0 |
| M10 | 0.8 | 0.84 | 14 | 1.15 | 0.95 | 3.35 | 0.52 | 0.5 | 0.45 | 0 | 0 |
| M11 | 0.8 | 0.84 | 14.25 | 1.15 | 0.95 | 3.35 | 0.52 | 0.5 | 0.45 | 0 | 0 |
| M12 | 0.8 | 0.84 | 14.5 | 1.15 | 0.95 | 3.35 | 0.52 | 0.5 | 0.45 | 0 | 0 |
| M13 | 0.8 | 0.84 | 14.75 | 1.15 | 0.95 | 3.35 | 0.52 | 0.5 | 0.45 | 0 | 0 |
| M14 | 0.8 | 0.84 | 15 | 1.15 | 0.95 | 3.35 | 0.52 | 0.5 | 0.45 | 0 | 0 |
| M15 | 0.8 | 0.86 | 13.5 | 1.15 | 0.95 | 3.35 | 0.52 | 0.5 | 0.45 | 0 | 0 |
| M16 | 0.8 | 0.86 | 13.75 | 1.15 | 0.95 | 3.35 | 0.52 | 0.5 | 0.45 | 0 | 0 |
| M17 | 0.8 | 0.86 | 14 | 1.15 | 0.95 | 3.35 | 0.52 | 0.5 | 0.45 | 0 | 0 |
| M18 | 0.8 | 0.86 | 14.25 | 1.15 | 0.95 | 3.35 | 0.52 | 0.5 | 0.45 | 0 | 0 |
| M19 | 0.8 | 0.86 | 14.5 | 1.15 | 0.95 | 3.35 | 0.52 | 0.5 | 0.45 | 0 | 0 |
| M20 | 0.8 | 0.86 | 14.75 | 1.15 | 0.95 | 3.35 | 0.52 | 0.5 | 0.45 | 0 | 0 |
| M21 | 0.8 | 0.86 | 15 | 1.15 | 0.95 | 3.35 | 0.52 | 0.5 | 0.45 | 0 | 0 |
| M22 | 0.8 | 0.88 | 13.5 | 1.15 | 0.95 | 3.35 | 0.52 | 0.5 | 0.45 | 0 | 0 |
| M23 | 0.8 | 0.88 | 13.75 | 1.15 | 0.95 | 3.35 | 0.52 | 0.5 | 0.45 | 0 | 0 |
| M24 | 0.8 | 0.88 | 14 | 1.15 | 0.95 | 3.35 | 0.52 | 0.5 | 0.45 | 0 | 0 |
| M25 | 0.8 | 0.88 | 14.25 | 1.15 | 0.95 | 3.35 | 0.52 | 0.5 | 0.45 | 0 | 0 |
| M26 | 0.8 | 0.88 | 14.5 | 1.15 | 0.95 | 3.35 | 0.52 | 0.5 | 0.45 | 0 | 0 |
| M27 | 0.8 | 0.88 | 14.75 | 1.15 | 0.95 | 3.35 | 0.52 | 0.5 | 0.45 | 0 | 0 |
| M28 | 0.8 | 0.88 | 15 | 1.15 | 0.95 | 3.35 | 0.52 | 0.5 | 0.45 | 0 | 0 |
| M29 | 0.8 | 0.9 | 13.5 | 1.15 | 0.95 | 3.35 | 0.52 | 0.5 | 0.45 | 0 | 0 |
| M30 | 0.8 | 0.9 | 13.75 | 1.15 | 0.95 | 3.35 | 0.52 | 0.5 | 0.45 | 0 | 0 |
| M31 | 0.8 | 0.9 | 14 | 1.15 | 0.95 | 3.35 | 0.52 | 0.5 | 0.45 | 0 | 0 |
| M32 | 0.8 | 0.9 | 14.25 | 1.15 | 0.95 | 3.35 | 0.52 | 0.5 | 0.45 | 0 | 0 |
| M33 | 0.8 | 0.9 | 14.5 | 1.15 | 0.95 | 3.35 | 0.52 | 0.5 | 0.45 | 0 | 0 |
| M34 | 0.8 | 0.9 | 14.75 | 1.15 | 0.95 | 3.35 | 0.52 | 0.5 | 0.45 | 0 | 0 |
| M35 | 0.8 | 0.9 | 15 | 1.15 | 0.95 | 3.35 | 0.52 | 0.5 | 0.45 | 0 | 0 |
| M36 | 0.8 | 0.92 | 13.5 | 1.15 | 0.95 | 3.35 | 0.52 | 0.5 | 0.45 | 0 | 0 |
| M37 | 0.8 | 0.92 | 13.75 | 1.15 | 0.95 | 3.35 | 0.52 | 0.5 | 0.45 | 0 | 0 |
| M38 | 0.8 | 0.92 | 14 | 1.15 | 0.95 | 3.35 | 0.52 | 0.5 | 0.45 | 0 | 0 |
| M39 | 0.8 | 0.92 | 14.25 | 1.15 | 0.95 | 3.35 | 0.52 | 0.5 | 0.45 | 0 | 0 |
| M40 | 0.8 | 0.92 | 14.5 | 1.15 | 0.95 | 3.35 | 0.52 | 0.5 | 0.45 | 0 | 0 |
| M41 | 0.8 | 0.92 | 14.75 | 1.15 | 0.95 | 3.35 | 0.52 | 0.5 | 0.45 | 0 | 0 |
| M42 | 0.8 | 0.92 | 15 | 1.15 | 0.95 | 3.35 | 0.52 | 0.5 | 0.45 | 0 | 0 |
| M43 | 0.8 | 0.94 | 13.5 | 1.15 | 0.95 | 3.35 | 0.52 | 0.5 | 0.45 | 0 | 0 |
| M44 | 0.8 | 0.94 | 13.75 | 1.15 | 0.95 | 3.35 | 0.52 | 0.5 | 0.45 | 0 | 0 |
| M45 | 0.8 | 0.94 | 14 | 1.15 | 0.95 | 3.35 | 0.52 | 0.5 | 0.45 | 0 | 0 |
| M46 | 0.8 | 0.94 | 14.25 | 1.15 | 0.95 | 3.35 | 0.52 | 0.5 | 0.45 | 0 | 0 |
| M47 | 0.8 | 0.94 | 14.5 | 1.15 | 0.95 | 3.35 | 0.52 | 0.5 | 0.45 | 0 | 0 |
| M48 | 0.8 | 0.94 | 14.75 | 1.15 | 0.95 | 3.35 | 0.52 | 0.5 | 0.45 | 0 | 0 |
| M49 | 0.8 | 0.94 | 15 | 1.15 | 0.95 | 3.35 | 0.52 | 0.5 | 0.45 | 0 | 0 |
| M50 | 0.8 | 0.96 | 13.5 | 1.15 | 0.95 | 3.35 | 0.52 | 0.5 | 0.45 | 0 | 0 |
| M51 | 0.8 | 0.96 | 13.75 | 1.15 | 0.95 | 3.35 | 0.52 | 0.5 | 0.45 | 0 | 0 |
| M52 | 0.8 | 0.96 | 14 | 1.15 | 0.95 | 3.35 | 0.52 | 0.5 | 0.45 | 0 | 0 |
| M53 | 0.8 | 0.96 | 14.25 | 1.15 | 0.95 | 3.35 | 0.52 | 0.5 | 0.45 | 0 | 0 |
| M54 | 0.8 | 0.96 | 14.5 | 1.15 | 0.95 | 3.35 | 0.52 | 0.5 | 0.45 | 0 | 0 |
| M55 | 0.8 | 0.96 | 14.75 | 1.15 | 0.95 | 3.35 | 0.52 | 0.5 | 0.45 | 0 | 0 |

TABLE 3-continued

Alloy chemistries in weight percent, balance Fe, for selected alloys evaluated using thermodynamic models which meet thermodynamic criteria

| Alloy | B | C | Cr | Mn | Mo | Nb | Si | Ti | V | W | Zr |
|---|---|---|---|---|---|---|---|---|---|---|---|
| M56 | 0.8 | 0.96 | 15 | 1.15 | 0.95 | 3.35 | 0.52 | 0.5 | 0.45 | 0 | 0 |
| M57 | 0.8 | 0.98 | 13.5 | 1.15 | 0.95 | 3.35 | 0.52 | 0.5 | 0.45 | 0 | 0 |
| M58 | 0.8 | 0.98 | 13.75 | 1.15 | 0.95 | 3.35 | 0.52 | 0.5 | 0.45 | 0 | 0 |
| M59 | 0.8 | 0.98 | 14 | 1.15 | 0.95 | 3.35 | 0.52 | 0.5 | 0.45 | 0 | 0 |
| M60 | 0.8 | 0.98 | 14.25 | 1.15 | 0.95 | 3.35 | 0.52 | 0.5 | 0.45 | 0 | 0 |
| M61 | 0.8 | 0.98 | 14.5 | 1.15 | 0.95 | 3.35 | 0.52 | 0.5 | 0.45 | 0 | 0 |
| M62 | 0.8 | 0.98 | 14.75 | 1.15 | 0.95 | 3.35 | 0.52 | 0.5 | 0.45 | 0 | 0 |
| M63 | 0.8 | 0.98 | 15 | 1.15 | 0.95 | 3.35 | 0.52 | 0.5 | 0.45 | 0 | 0 |
| M64 | 0.8 | 1 | 13.5 | 1.15 | 0.95 | 3.35 | 0.52 | 0.5 | 0.45 | 0 | 0 |
| M65 | 0.8 | 1 | 13.75 | 1.15 | 0.95 | 3.35 | 0.52 | 0.5 | 0.45 | 0 | 0 |
| M66 | 0.8 | 1 | 14 | 1.15 | 0.95 | 3.35 | 0.52 | 0.5 | 0.45 | 0 | 0 |
| M67 | 0.8 | 1 | 14.25 | 1.15 | 0.95 | 3.35 | 0.52 | 0.5 | 0.45 | 0 | 0 |
| M68 | 0.8 | 1 | 14.5 | 1.15 | 0.95 | 3.35 | 0.52 | 0.5 | 0.45 | 0 | 0 |
| M69 | 0.8 | 1 | 14.75 | 1.15 | 0.95 | 3.35 | 0.52 | 0.5 | 0.45 | 0 | 0 |
| M70 | 0.8 | 1 | 15 | 1.15 | 0.95 | 3.35 | 0.52 | 0.5 | 0.45 | 0 | 0 |
| M71 | 0.8 | 1.02 | 13.5 | 1.15 | 0.95 | 3.35 | 0.52 | 0.5 | 0.45 | 0 | 0 |
| M72 | 0.8 | 1.02 | 13.75 | 1.15 | 0.95 | 3.35 | 0.52 | 0.5 | 0.45 | 0 | 0 |
| M73 | 0.8 | 1.02 | 14 | 1.15 | 0.95 | 3.35 | 0.52 | 0.5 | 0.45 | 0 | 0 |
| M74 | 0.8 | 1.02 | 14.25 | 1.15 | 0.95 | 3.35 | 0.52 | 0.5 | 0.45 | 0 | 0 |
| M75 | 0.8 | 1.02 | 14.5 | 1.15 | 0.95 | 3.35 | 0.52 | 0.5 | 0.45 | 0 | 0 |
| M76 | 0.8 | 1.02 | 14.75 | 1.15 | 0.95 | 3.35 | 0.52 | 0.5 | 0.45 | 0 | 0 |
| M77 | 0.8 | 1.02 | 15 | 1.15 | 0.95 | 3.35 | 0.52 | 0.5 | 0.45 | 0 | 0 |
| M78 | 0.8 | 1.04 | 13.5 | 1.15 | 0.95 | 3.35 | 0.52 | 0.5 | 0.45 | 0 | 0 |
| M79 | 0.8 | 1.04 | 13.75 | 1.15 | 0.95 | 3.35 | 0.52 | 0.5 | 0.45 | 0 | 0 |
| M80 | 0.8 | 1.04 | 14 | 1.15 | 0.95 | 3.35 | 0.52 | 0.5 | 0.45 | 0 | 0 |
| M81 | 0.8 | 1.04 | 14.25 | 1.15 | 0.95 | 3.35 | 0.52 | 0.5 | 0.45 | 0 | 0 |
| M82 | 1.1 | 0.9 | 5 | 0 | 1 | 2.5 | 0.5 | 1 | 0.5 | 0 | 0 |
| M83 | 1.1 | 0.9 | 5 | 0 | 1 | 3 | 0.5 | 1 | 0.5 | 0 | 0 |
| M84 | 1.1 | 0.9 | 5 | 0 | 1 | 3.5 | 0.5 | 1 | 0.5 | 0 | 0 |
| M85 | 1.1 | 0.9 | 5 | 0 | 1 | 4 | 0.5 | 1 | 0.5 | 0 | 0 |
| M86 | 1.1 | 0.9 | 5 | 0 | 1 | 5 | 0.5 | 0 | 0.5 | 0 | 0 |
| M87 | 0.7 | 0.8 | 14.25 | 1.1 | 1 | 3.5 | 0.5 | 0.5 | 0.5 | 0 | 0 |
| M88 | 0.7 | 0.9 | 14.25 | 1.1 | 1 | 3.5 | 0.5 | 0.5 | 0.5 | 0 | 0 |
| M89 | 0.7 | 1 | 14.25 | 1.1 | 1 | 3.5 | 0.5 | 0.5 | 0.5 | 0 | 0 |
| M90 | 0.8 | 0.9 | 14.25 | 1.1 | 1 | 3.5 | 0.5 | 0.5 | 0.5 | 0 | 0 |
| M91 | 0.8 | 1 | 14.25 | 1.1 | 1 | 3.5 | 0.5 | 0.5 | 0.5 | 0 | 0 |
| M92 | 0.9 | 0.9 | 14.25 | 1.1 | 1 | 3.5 | 0.5 | 0.5 | 0.5 | 0 | 0 |
| M93 | 0.9 | 1 | 14.25 | 1.1 | 1 | 3.5 | 0.5 | 0.5 | 0.5 | 0 | 0 |
| M94 | 0.8 | 0.95 | 1 | 0 | 1 | 3 | 0.5 | 0 | 0.5 | 0 | 0 |
| M95 | 0.8 | 0.95 | 2 | 0 | 1 | 2.5 | 0.5 | 1.5 | 0.5 | 0 | 0 |
| M96 | 0.8 | 0.95 | 2 | 0 | 1 | 4 | 0.5 | 0.5 | 0.5 | 0 | 0 |
| M97 | 0.8 | 0.95 | 2.5 | 0 | 1 | 3.5 | 0.5 | 0.5 | 0.5 | 0 | 0 |
| M98 | 0.8 | 0.95 | 2.5 | 0 | 1 | 4 | 0.5 | 0.5 | 0.5 | 0 | 0 |
| M99 | 0.8 | 0.95 | 2.5 | 0 | 1 | 4.5 | 0.5 | 0.5 | 0.5 | 0 | 0 |
| M100 | 0.8 | 0.95 | 2.5 | 0 | 1 | 5 | 0.5 | 1 | 0.5 | 0 | 0 |
| M101 | 0.8 | 0.95 | 3 | 0 | 1 | 3 | 0.5 | 0.5 | 0.5 | 0 | 0 |
| M102 | 0.8 | 0.95 | 3 | 0 | 1 | 3.5 | 0.5 | 0.5 | 0.5 | 0 | 0 |
| M103 | 0.8 | 0.95 | 3 | 0 | 1 | 4 | 0.5 | 0.5 | 0.5 | 0 | 0 |
| M104 | 0.8 | 0.95 | 3 | 0 | 1 | 4.5 | 0.5 | 0.5 | 0.5 | 0 | 0 |
| M105 | 0.8 | 0.95 | 3 | 0 | 1 | 4.5 | 0.5 | 1 | 0.5 | 0 | 0 |
| M106 | 0.8 | 0.95 | 3.5 | 0 | 1 | 3 | 0.5 | 0.5 | 0.5 | 0 | 0 |
| M107 | 0.8 | 0.95 | 3.5 | 0 | 1 | 3.5 | 0.5 | 0.5 | 0.5 | 0 | 0 |
| M108 | 0.8 | 0.95 | 3.5 | 0 | 1 | 4 | 0.5 | 0.5 | 0.5 | 0 | 0 |
| M109 | 0.8 | 0.95 | 3.5 | 0 | 1 | 4.5 | 0.5 | 0.5 | 0.5 | 0 | 0 |
| M110 | 0.8 | 0.95 | 4 | 0 | 1 | 2.5 | 0.5 | 0.5 | 0.5 | 0 | 0 |
| M111 | 0.8 | 0.95 | 4 | 0 | 1 | 3 | 0.5 | 0.5 | 0.5 | 0 | 0 |
| M112 | 0.8 | 0.95 | 4 | 0 | 1 | 3.5 | 0.5 | 0 | 0.5 | 0 | 0 |
| M113 | 0.8 | 0.95 | 4 | 0 | 1 | 3.5 | 0.5 | 0.5 | 0.5 | 0 | 0 |
| M114 | 0.8 | 0.95 | 4 | 0 | 1 | 4 | 0.5 | 0 | 0.5 | 0 | 0 |
| M115 | 0.8 | 0.95 | 4 | 0 | 1 | 4 | 0.5 | 0.5 | 0.5 | 0 | 0 |
| M116 | 0.8 | 0.95 | 4 | 0 | 1 | 4.5 | 0.5 | 0 | 0.5 | 0 | 0 |
| M117 | 0.8 | 0.95 | 4 | 0 | 1 | 4.5 | 0.5 | 0.5 | 0.5 | 0 | 0 |
| M118 | 0.8 | 0.95 | 4 | 0 | 1 | 5 | 0.5 | 0 | 0.5 | 0 | 0 |
| M119 | 0.8 | 0.95 | 4.5 | 0 | 1 | 2.5 | 0.5 | 0 | 0.5 | 0 | 0 |
| M120 | 0.8 | 0.95 | 4.5 | 0 | 1 | 2.5 | 0.5 | 0.5 | 0.5 | 0 | 0 |
| M121 | 0.8 | 0.95 | 4.5 | 0 | 1 | 3 | 0.5 | 0 | 0.5 | 0 | 0 |
| M122 | 0.8 | 0.95 | 4.5 | 0 | 1 | 3 | 0.5 | 0.5 | 0.5 | 0 | 0 |
| M123 | 0.8 | 0.95 | 4.5 | 0 | 1 | 3.5 | 0.5 | 0 | 0.5 | 0 | 0 |
| M124 | 0.8 | 0.95 | 4.5 | 0 | 1 | 3.5 | 0.5 | 0.5 | 0.5 | 0 | 0 |
| M125 | 0.8 | 0.95 | 4.5 | 0 | 1 | 4 | 0.5 | 0 | 0.5 | 0 | 0 |
| M126 | 0.8 | 0.95 | 4.5 | 0 | 1 | 4 | 0.5 | 0.5 | 0.5 | 0 | 0 |
| M127 | 0.8 | 0.95 | 4.5 | 0 | 1 | 4.5 | 0.5 | 0 | 0.5 | 0 | 0 |
| M128 | 0.8 | 0.95 | 4.5 | 0 | 1 | 4.5 | 0.5 | 0.5 | 0.5 | 0 | 0 |
| M129 | 0.8 | 0.95 | 4.5 | 0 | 1 | 5 | 0.5 | 0 | 0.5 | 0 | 0 |
| M130 | 0.8 | 0.95 | 4.5 | 0 | 1 | 5.5 | 0.5 | 0 | 0.5 | 0 | 0 |

TABLE 3-continued

Alloy chemistries in weight percent, balance Fe, for selected alloys evaluated using thermodynamic models which meet thermodynamic criteria

| Alloy | B | C | Cr | Mn | Mo | Nb | Si | Ti | V | W | Zr |
|---|---|---|---|---|---|---|---|---|---|---|---|
| M131 | 0.8 | 0.95 | 5 | 0 | 1 | 2.5 | 0.5 | 0 | 0.5 | 0 | 0 |
| M132 | 0.8 | 0.95 | 5 | 0 | 1 | 2.5 | 0.5 | 0.5 | 0.5 | 0 | 0 |
| M133 | 0.8 | 0.95 | 5 | 0 | 1 | 3 | 0.5 | 0 | 0.5 | 0 | 0 |
| M134 | 0.8 | 0.95 | 5 | 0 | 1 | 3 | 0.5 | 0.5 | 0.5 | 0 | 0 |
| M135 | 0.8 | 0.95 | 5 | 0 | 1 | 3.5 | 0.5 | 0 | 0.5 | 0 | 0 |
| M136 | 0.8 | 0.95 | 5 | 0 | 1 | 3.5 | 0.5 | 0.5 | 0.5 | 0 | 0 |
| M137 | 0.8 | 0.95 | 5 | 0 | 1 | 4 | 0.5 | 0 | 0.5 | 0 | 0 |
| M138 | 0.8 | 0.95 | 5 | 0 | 1 | 4 | 0.5 | 0.5 | 0.5 | 0 | 0 |
| M139 | 0.8 | 0.95 | 5 | 0 | 1 | 4.5 | 0.5 | 0 | 0.5 | 0 | 0 |
| M140 | 0.8 | 0.95 | 5 | 0 | 1 | 4.5 | 0.5 | 0.5 | 0.5 | 0 | 0 |
| M141 | 0.8 | 0.95 | 5 | 0 | 1 | 5 | 0.5 | 0 | 0.5 | 0 | 0 |
| M142 | 0.8 | 0.95 | 5 | 0 | 1 | 5.5 | 0.5 | 0.5 | 0.5 | 0 | 0 |
| M143 | 0.6 | 0.8 | 10 | 0 | 0 | 3.5 | 0 | 0 | 0 | 0 | 0 |
| M144 | 0.6 | 0.8 | 12 | 0 | 0 | 3.5 | 0 | 0 | 0 | 0 | 0 |
| M145 | 0.6 | 0.8 | 14 | 0 | 0 | 3.5 | 0 | 0 | 0 | 0 | 0 |
| M146 | 0.6 | 0.8 | 16 | 0 | 0 | 3.5 | 0 | 0 | 0 | 0 | 0 |
| M147 | 0.6 | 0.8 | 18 | 0 | 0 | 3.5 | 0 | 0 | 0 | 0 | 0 |
| M148 | 0.6 | 0.8 | 20 | 0 | 0 | 3.5 | 0 | 0 | 0 | 0 | 0 |
| M149 | 0.6 | 0.8 | 22 | 0 | 0 | 3.5 | 0 | 0 | 0 | 0 | 0 |
| M150 | 0.6 | 1 | 10 | 0 | 0 | 3.5 | 0 | 0 | 0 | 0 | 0 |
| M151 | 0.6 | 1 | 12 | 0 | 0 | 3.5 | 0 | 0 | 0 | 0 | 0 |
| M152 | 0.6 | 1 | 14 | 0 | 0 | 3.5 | 0 | 0 | 0 | 0 | 0 |
| M153 | 0.6 | 1 | 16 | 0 | 0 | 3.5 | 0 | 0 | 0 | 0 | 0 |
| M154 | 0.6 | 1 | 18 | 0 | 0 | 3.5 | 0 | 0 | 0 | 0 | 0 |
| M155 | 0.6 | 1.2 | 10 | 0 | 0 | 3.5 | 0 | 0 | 0 | 0 | 0 |
| M156 | 0.6 | 1.2 | 12 | 0 | 0 | 3.5 | 0 | 0 | 0 | 0 | 0 |
| M157 | 0.6 | 1.2 | 14 | 0 | 0 | 3.5 | 0 | 0 | 0 | 0 | 0 |
| M158 | 0.8 | 0.8 | 10 | 0 | 0 | 3.5 | 0 | 0 | 0 | 0 | 0 |
| M159 | 0.8 | 0.8 | 12 | 0 | 0 | 3.5 | 0 | 0 | 0 | 0 | 0 |
| M160 | 0.8 | 0.8 | 14 | 0 | 0 | 3.5 | 0 | 0 | 0 | 0 | 0 |
| M161 | 0.8 | 0.8 | 16 | 0 | 0 | 3.5 | 0 | 0 | 0 | 0 | 0 |
| M162 | 0.8 | 0.8 | 18 | 0 | 0 | 3.5 | 0 | 0 | 0 | 0 | 0 |
| M163 | 0.8 | 1 | 10 | 0 | 0 | 3.5 | 0 | 0 | 0 | 0 | 0 |
| M164 | 0.8 | 1 | 12 | 0 | 0 | 3.5 | 0 | 0 | 0 | 0 | 0 |
| M165 | 0.8 | 1 | 14 | 0 | 0 | 3.5 | 0 | 0 | 0 | 0 | 0 |
| M166 | 0.8 | 1.2 | 10 | 0 | 0 | 3.5 | 0 | 0 | 0 | 0 | 0 |
| M167 | 1 | 0.8 | 10 | 0 | 0 | 3.5 | 0 | 0 | 0 | 0 | 0 |
| M168 | 1 | 0.8 | 12 | 0 | 0 | 3.5 | 0 | 0 | 0 | 0 | 0 |
| M169 | 1 | 0.8 | 14 | 0 | 0 | 3.5 | 0 | 0 | 0 | 0 | 0 |
| M170 | 1 | 0.8 | 16 | 0 | 0 | 3.5 | 0 | 0 | 0 | 0 | 0 |
| M171 | 1 | 0.8 | 18 | 0 | 0 | 3.5 | 0 | 0 | 0 | 0 | 0 |
| M172 | 1 | 1 | 10 | 0 | 0 | 3.5 | 0 | 0 | 0 | 0 | 0 |
| M173 | 0.5 | 1.25 | 1 | 0 | 1 | 5 | 0.5 | 1.5 | 0.5 | 0 | 0 |
| M174 | 0.5 | 1.25 | 1 | 0 | 1 | 5.5 | 0.5 | 1.5 | 0.5 | 0 | 0 |
| M175 | 0.5 | 1.25 | 1.5 | 0 | 1 | 2.5 | 0.5 | 1 | 0.5 | 0 | 0 |
| M176 | 0.5 | 1.25 | 1.5 | 0 | 1 | 3 | 0.5 | 1 | 0.5 | 0 | 0 |
| M177 | 0.5 | 1.25 | 1.5 | 0 | 1 | 3.5 | 0.5 | 1 | 0.5 | 0 | 0 |
| M178 | 0.5 | 1.25 | 1.5 | 0 | 1 | 4 | 0.5 | 1 | 0.5 | 0 | 0 |
| M179 | 0.5 | 1.25 | 2 | 0 | 1 | 2.5 | 0.5 | 1 | 0.5 | 0 | 0 |
| M180 | 0.5 | 1.25 | 2 | 0 | 1 | 3 | 0.5 | 1 | 0.5 | 0 | 0 |
| M181 | 0.5 | 1.25 | 2 | 0 | 1 | 3.5 | 0.5 | 0 | 0.5 | 0 | 0 |
| M182 | 0.5 | 1.25 | 2.5 | 0 | 1 | 2.5 | 0.5 | 1 | 0.5 | 0 | 0 |
| M183 | 0.5 | 1.25 | 2.5 | 0 | 1 | 3 | 0.5 | 1 | 0.5 | 0 | 0 |
| M184 | 0.5 | 1.25 | 2.5 | 0 | 1 | 5.5 | 0.5 | 1 | 0.5 | 0 | 0 |
| M185 | 0.5 | 1.25 | 3 | 0 | 1 | 2.5 | 0.5 | 1 | 0.5 | 0 | 0 |
| M186 | 0.5 | 1.25 | 3 | 0 | 1 | 3 | 0.5 | 1 | 0.5 | 0 | 0 |
| M187 | 0.5 | 1.25 | 3 | 0 | 1 | 5.5 | 0.5 | 1 | 0.5 | 0 | 0 |
| M188 | 0.5 | 1.25 | 3.5 | 0 | 1 | 2.5 | 0.5 | 1 | 0.5 | 0 | 0 |
| M189 | 0.5 | 1.25 | 3.5 | 0 | 1 | 3 | 0.5 | 1 | 0.5 | 0 | 0 |
| M190 | 0.5 | 1.25 | 3.5 | 0 | 1 | 5.5 | 0.5 | 1 | 0.5 | 0 | 0 |
| M191 | 0.5 | 1.25 | 4 | 0 | 1 | 3 | 0.5 | 0.5 | 0.5 | 0 | 0 |
| M192 | 0.5 | 1.25 | 4 | 0 | 1 | 5.5 | 0.5 | 1 | 0.5 | 0 | 0 |
| M193 | 0.5 | 1.25 | 4.5 | 0 | 1 | 2.5 | 0.5 | 1.5 | 0.5 | 0 | 0 |
| M194 | 0.5 | 1.25 | 4.5 | 0 | 1 | 5.5 | 0.5 | 1 | 0.5 | 0 | 0 |
| M195 | 0.5 | 1.25 | 5 | 0 | 1 | 2.5 | 0.5 | 1 | 0.5 | 0 | 0 |
| M196 | 0.5 | 1.25 | 5 | 0 | 1 | 3 | 0.5 | 1 | 0.5 | 0 | 0 |
| M197 | 0.5 | 1.25 | 5 | 0 | 1 | 4 | 0.5 | 1 | 0.5 | 0 | 0 |
| M198 | 0.5 | 1.25 | 5 | 0 | 1 | 5.5 | 0.5 | 1 | 0.5 | 0 | 0 |
| M199 | 0.8 | 0.95 | 0.5 | 0 | 1 | 1.5 | 0.5 | 1 | 0.5 | 0 | 0 |
| M200 | 0.8 | 0.95 | 0.5 | 0 | 1 | 2 | 0.5 | 1 | 0.5 | 0 | 0 |
| M201 | 0.8 | 0.95 | 0.5 | 0 | 1 | 2.25 | 0.5 | 1.75 | 0.5 | 0 | 0 |
| M202 | 0.8 | 0.95 | 0.5 | 0 | 1 | 2.75 | 0.5 | 1.5 | 0.5 | 0 | 0 |
| M203 | 0.8 | 0.95 | 0.5 | 0 | 1 | 3 | 0.5 | 2 | 0.5 | 0 | 0 |
| M204 | 0.8 | 0.95 | 0.5 | 0 | 1 | 3.25 | 0.5 | 1 | 0.5 | 0 | 0 |
| M205 | 0.5 | 0.95 | 0.5 | 1 | 1 | 2 | 0.5 | 1.5 | 0 | 0 | 0 |

TABLE 3-continued

Alloy chemistries in weight percent, balance Fe, for selected alloys evaluated using thermodynamic models which meet thermodynamic criteria

| Alloy | B | C | Cr | Mn | Mo | Nb | Si | Ti | V | W | Zr |
|---|---|---|---|---|---|---|---|---|---|---|---|
| M206 | 0.5 | 0.95 | 0.5 | 1 | 1 | 2.5 | 0.5 | 0.5 | 0 | 0 | 0 |
| M207 | 0.5 | 0.95 | 0.5 | 1 | 1 | 2.5 | 0.5 | 1.5 | 0 | 0 | 0 |
| M208 | 0.5 | 0.95 | 0.5 | 1 | 1 | 3 | 0.5 | 0.5 | 0 | 0 | 0 |
| M209 | 0.5 | 0.95 | 0.5 | 1 | 1 | 3.5 | 0.5 | 0.5 | 0 | 0 | 0 |
| M210 | 0.5 | 0.95 | 0.5 | 1 | 1 | 4 | 0.5 | 0.5 | 0 | 0 | 0 |
| M211 | 0.5 | 0.95 | 0.5 | 1 | 1 | 4 | 0.5 | 1 | 0 | 0 | 0 |
| M212 | 0.65 | 0.95 | 0.5 | 1 | 1 | 2 | 0.5 | 0.5 | 0 | 0 | 0 |
| M213 | 0.65 | 0.95 | 0.5 | 1 | 1 | 2 | 0.5 | 1.5 | 0 | 0 | 0 |
| M214 | 0.65 | 0.95 | 0.5 | 1 | 1 | 2.5 | 0.5 | 2 | 0 | 0 | 0 |
| M215 | 0.65 | 0.95 | 0.5 | 1 | 1 | 3 | 0.5 | 1 | 0 | 0 | 0 |
| M216 | 0.65 | 0.95 | 0.5 | 1 | 1 | 3.5 | 0.5 | 1 | 0 | 0 | 0 |
| M217 | 1.07 | 0.65 | 3.36 | 0.78 | 0.68 | 2.67 | 0.44 | 0.45 | 0.36 | 0 | 0 |
| M218 | 0.1 | 0.95 | 5.5 | 1 | 0.7 | 0 | 0.5 | 2.3 | 0.07 | 0 | 0 |
| M219 | 0.1 | 0.95 | 5.5 | 1 | 0.7 | 0.25 | 0.5 | 2.3 | 0.07 | 0 | 0 |
| M220 | 0.1 | 0.95 | 5.5 | 1 | 0.7 | 0.5 | 0.5 | 2.3 | 0.07 | 0 | 0 |
| M221 | 0.1 | 0.95 | 5.5 | 1 | 0.7 | 0.75 | 0.5 | 2.3 | 0.07 | 0 | 0 |
| M222 | 0.1 | 0.95 | 5.5 | 1 | 0.7 | 1 | 0.5 | 2.3 | 0.07 | 0 | 0 |
| M223 | 0.1 | 0.95 | 5.5 | 1 | 0.7 | 2 | 0.5 | 2.3 | 0.07 | 0 | 0 |
| M224 | 0.1 | 0.95 | 5.5 | 1 | 0.7 | 2.25 | 0.5 | 2.3 | 0.07 | 0 | 0 |
| M225 | 0.1 | 0.95 | 5.5 | 1 | 0.7 | 2.5 | 0.5 | 2.3 | 0.07 | 0 | 0 |
| M226 | 0.2 | 0.95 | 5.5 | 1 | 0.7 | 0.25 | 0.5 | 2.3 | 0.07 | 0 | 0 |
| M227 | 0.2 | 0.95 | 5.5 | 1 | 0.7 | 0.5 | 0.5 | 2.3 | 0.07 | 0 | 0 |
| M228 | 0.2 | 0.95 | 5.5 | 1 | 0.7 | 0.75 | 0.5 | 2.3 | 0.07 | 0 | 0 |
| M229 | 0.2 | 0.95 | 5.5 | 1 | 0.7 | 1 | 0.5 | 2.3 | 0.07 | 0 | 0 |
| M230 | 0.2 | 0.95 | 5.5 | 1 | 0.7 | 2.25 | 0.5 | 2.3 | 0.07 | 0 | 0 |
| M231 | 0.8 | 0.95 | 5.5 | 1 | 0.7 | 3.25 | 0.5 | 2.3 | 0.07 | 0 | 0 |
| M232 | 1 | 0.95 | 5.5 | 1 | 0.7 | 3.5 | 0.5 | 2.3 | 0.07 | 0 | 0 |
| M233 | 1 | 0.95 | 5.5 | 1 | 0.7 | 3.75 | 0.5 | 2.3 | 0.07 | 0 | 0 |
| M234 | 0.6 | 1.06 | 5.2 | 1 | 0.75 | 2.45 | 0.42 | 0.35 | 0.35 | 0 | 0 |
| M235 | 0.7 | 1.06 | 5.2 | 1 | 0.75 | 2.45 | 0.42 | 0.35 | 0.35 | 0 | 0 |
| M236 | 0.8 | 1.06 | 5.2 | 1 | 0.75 | 2.45 | 0.42 | 0.35 | 0.35 | 0 | 0 |
| M237 | 0.9 | 1.06 | 5.2 | 1 | 0.75 | 2.45 | 0.42 | 0.35 | 0.35 | 0 | 0 |
| M238 | 0.5 | 1.35 | 7 | 1.1 | 1 | 3.5 | 0.5 | 0.5 | 0.5 | 0 | 0 |
| M239 | 0.6 | 1.35 | 7 | 1.1 | 1 | 3.5 | 0.5 | 0.5 | 0.5 | 0 | 0 |
| M240 | 0.7 | 1.35 | 7 | 1.1 | 1 | 3.5 | 0.5 | 0.5 | 0.5 | 0 | 0 |
| M241 | 0.9 | 1.35 | 7 | 1.1 | 1 | 3.5 | 0.5 | 0.5 | 0.5 | 0 | 0 |
| M242 | 0.6725 | 1.005 | 4.9675 | 0.83 | 0.7 | 2.45 | 0.35 | 0.35 | 0.35 | 0 | 0 |
| M243 | 0.7617 | 1.2465 | 6.3902 | 1.019 | 0.91 | 3.185 | 0.455 | 0.455 | 0.455 | 0 | 0 |
| M244 | 0.7885 | 1.3189 | 6.8171 | 1.0757 | 0.973 | 3.4055 | 0.4865 | 0.4865 | 0.4865 | 0 | 0 |
| M245 | 0.6725 | 0.83 | 4.9675 | 0.83 | 0.7 | 2.45 | 0.35 | 0.35 | 0.35 | 0 | 0 |
| M246 | 0.7617 | 1.019 | 6.3902 | 1.019 | 0.91 | 3.185 | 0.455 | 0.455 | 0.455 | 0 | 0 |
| M247 | 0.7885 | 1.0757 | 6.8171 | 1.0757 | 0.973 | 3.4055 | 0.4865 | 0.4865 | 0.4865 | 0 | 0 |
| M248 | 0.6725 | 1.11 | 4.9675 | 0.83 | 0.7 | 2.45 | 0.35 | 0.35 | 0.35 | 0 | 0 |
| M249 | 0.7617 | 1.383 | 6.3902 | 1.019 | 0.91 | 3.185 | 0.455 | 0.455 | 0.455 | 0 | 0 |
| M250 | 0.7885 | 1.4649 | 6.8171 | 1.0757 | 0.973 | 3.4055 | 0.4865 | 0.4865 | 0.4865 | 0 | 0 |
| M251 | 0.8 | 0.95 | 4 | 1.1 | 1 | 3.5 | 0.5 | 0.5 | 0.5 | 0 | 0 |
| M252 | 0.8 | 1.05 | 4 | 1.1 | 1 | 3.5 | 0.5 | 0.5 | 0.5 | 0 | 0 |
| M253 | 0.8 | 1.05 | 7 | 1.1 | 1 | 3.5 | 0.5 | 0.5 | 0.5 | 0 | 0 |
| M254 | 0.8 | 1.15 | 4 | 1.1 | 1 | 3.5 | 0.5 | 0.5 | 0.5 | 0 | 0 |
| M255 | 0.8 | 1.15 | 7 | 1.1 | 1 | 3.5 | 0.5 | 0.5 | 0.5 | 0 | 0 |
| M256 | 0.8 | 1.25 | 4 | 1.1 | 1 | 3.5 | 0.5 | 0.5 | 0.5 | 0 | 0 |
| M257 | 0.8 | 1.25 | 7 | 1.1 | 1 | 3.5 | 0.5 | 0.5 | 0.5 | 0 | 0 |
| M258 | 0.8 | 1.35 | 4 | 1.1 | 1 | 3.5 | 0.5 | 0.5 | 0.5 | 0 | 0 |
| M259 | 0.8 | 1.35 | 7 | 1.1 | 1 | 3.5 | 0.5 | 0.5 | 0.5 | 0 | 0 |
| M260 | 1 | 0.95 | 4 | 1.1 | 1 | 3.5 | 0.5 | 0.5 | 0.5 | 0 | 0 |
| M261 | 1 | 0.95 | 7 | 1.1 | 1 | 3.5 | 0.5 | 0.5 | 0.5 | 0 | 0 |
| M262 | 1 | 1.05 | 4 | 1.1 | 1 | 3.5 | 0.5 | 0.5 | 0.5 | 0 | 0 |
| M263 | 1 | 1.05 | 7 | 1.1 | 1 | 3.5 | 0.5 | 0.5 | 0.5 | 0 | 0 |
| M264 | 1 | 1.15 | 4 | 1.1 | 1 | 3.5 | 0.5 | 0.5 | 0.5 | 0 | 0 |
| M265 | 1 | 1.15 | 7 | 1.1 | 1 | 3.5 | 0.5 | 0.5 | 0.5 | 0 | 0 |
| M266 | 1 | 1.25 | 4 | 1.1 | 1 | 3.5 | 0.5 | 0.5 | 0.5 | 0 | 0 |
| M267 | 1 | 1.25 | 7 | 1.1 | 1 | 3.5 | 0.5 | 0.5 | 0.5 | 0 | 0 |
| M268 | 1 | 1.35 | 4 | 1.1 | 1 | 3.5 | 0.5 | 0.5 | 0.5 | 0 | 0 |
| M269 | 1 | 1.35 | 7 | 1.1 | 1 | 3.5 | 0.5 | 0.5 | 0.5 | 0 | 0 |
| M270 | 0.88 | 0.78 | 3.51 | 0.54 | 0.66 | 2.17 | 0.42 | 0.36 | 0.31 | 0 | 0 |
| M271 | 0.3 | 0.95 | 5.5 | 1 | 0.7 | 0 | 0.5 | 2.3 | 0.07 | 0 | 0 |
| M272 | 0.3 | 0.95 | 5.5 | 1 | 0.7 | 0.25 | 0.5 | 2.3 | 0.07 | 0 | 0 |
| M273 | 0.3 | 0.95 | 5.5 | 1 | 0.7 | 0.5 | 0.5 | 2.3 | 0.07 | 0 | 0 |
| M274 | 0.3 | 0.95 | 5.5 | 1 | 0.7 | 0.75 | 0.5 | 2.3 | 0.07 | 0 | 0 |
| M275 | 0.3 | 0.95 | 5.5 | 1 | 0.7 | 1 | 0.5 | 2.3 | 0.07 | 0 | 0 |
| M276 | 0.3 | 0.95 | 5.5 | 1 | 0.7 | 1.25 | 0.5 | 2.3 | 0.07 | 0 | 0 |
| M277 | 0.3 | 0.95 | 5.5 | 1 | 0.7 | 1.5 | 0.5 | 2.3 | 0.07 | 0 | 0 |
| M278 | 0.3 | 0.95 | 5.5 | 1 | 0.7 | 1.75 | 0.5 | 2.3 | 0.07 | 0 | 0 |
| M279 | 0.3 | 0.95 | 5.5 | 1 | 0.7 | 2 | 0.5 | 2.3 | 0.07 | 0 | 0 |
| M280 | 0.56 | 1.06 | 5.4 | 1 | 0.75 | 2.5 | 0.42 | 0.35 | 0.35 | 0 | 0 |

TABLE 3-continued

Alloy chemistries in weight percent, balance Fe, for selected alloys evaluated using thermodynamic models which meet thermodynamic criteria

| Alloy | B | C | Cr | Mn | Mo | Nb | Si | Ti | V | W | Zr |
|---|---|---|---|---|---|---|---|---|---|---|---|
| M281 | 0.76 | 1.06 | 3.79 | 1.01 | 0 | 2.45 | 0.42 | 0.35 | 0.35 | 0 | 0 |
| M282 | 0.86 | 1.06 | 3.79 | 1.01 | 0 | 2.45 | 0.42 | 0.35 | 0.35 | 0 | 0 |
| M283 | 0.4 | 1.35 | 9 | 1 | 0.75 | 2.45 | 0.42 | 0.35 | 0.35 | 0 | 0 |
| M284 | 0.4 | 1.35 | 10 | 1 | 0.75 | 2.45 | 0.42 | 0.35 | 0.35 | 0 | 0 |
| M285 | 0.5 | 1.35 | 8 | 1 | 0.75 | 2.45 | 0.42 | 0.35 | 0.35 | 0 | 0 |
| M286 | 0.5 | 1.35 | 9 | 1 | 0.75 | 2.45 | 0.42 | 0.35 | 0.35 | 0 | 0 |
| M287 | 0.5 | 1.35 | 10 | 1 | 0.75 | 2.45 | 0.42 | 0.35 | 0.35 | 0 | 0 |
| M288 | 0.4 | 0.7 | 10 | 1 | 0.75 | 2.45 | 0.42 | 0.35 | 0.35 | 0 | 0 |
| M289 | 0.4 | 0.8 | 10 | 1 | 0.75 | 2.45 | 0.42 | 0.35 | 0.35 | 0 | 0 |
| M290 | 0.4 | 0.9 | 10 | 1 | 0.75 | 2.45 | 0.42 | 0.35 | 0.35 | 0 | 0 |
| M291 | 0.4 | 1 | 10 | 1 | 0.75 | 2.45 | 0.42 | 0.35 | 0.35 | 0 | 0 |
| M292 | 0.4 | 1.1 | 10 | 1 | 0.75 | 2.45 | 0.42 | 0.35 | 0.35 | 0 | 0 |
| M293 | 0.63 | 0.7 | 10 | 1 | 0.75 | 2.45 | 0.42 | 0.35 | 0.35 | 0 | 0 |
| M294 | 0.63 | 0.8 | 10 | 1 | 0.75 | 2.45 | 0.42 | 0.35 | 0.35 | 0 | 0 |
| M295 | 0.63 | 0.9 | 10 | 1 | 0.75 | 2.45 | 0.42 | 0.35 | 0.35 | 0 | 0 |
| M296 | 0.63 | 1 | 10 | 1 | 0.75 | 2.45 | 0.42 | 0.35 | 0.35 | 0 | 0 |
| M297 | 0.63 | 1.1 | 10 | 1 | 0.75 | 2.45 | 0.42 | 0.35 | 0.35 | 0 | 0 |
| M298 | 0.1 | 0.7 | 1 | 1 | 1 | 3 | 0.65 | 0.65 | 0.5 | 0 | 0 |
| M299 | 0.1 | 0.7 | 2 | 1 | 1 | 3 | 0.65 | 0.65 | 0.5 | 0 | 0 |
| M300 | 0.5 | 1.25 | 1 | 0 | 1 | 3.5 | 0.5 | 2.5 | 0.5 | 0 | 0 |
| M301 | 0.5 | 1.25 | 1 | 0 | 1 | 5 | 0.5 | 1 | 0.5 | 0 | 0 |
| M302 | 0.5 | 1.25 | 1 | 0 | 1 | 4 | 0.5 | 1.5 | 0.5 | 0 | 0 |
| M303 | 0.5 | 1.25 | 1.5 | 0 | 1 | 5 | 0.5 | 1 | 0.5 | 0 | 0 |
| M304 | 1.1 | 0.9 | 1.5 | 0 | 1 | 4 | 0.5 | 2 | 0.5 | 0 | 0 |
| M305 | 0.5 | 1.25 | 2 | 0 | 1 | 4 | 0.5 | 1.5 | 0.5 | 0 | 0 |
| M306 | 0.5 | 1.25 | 2 | 0 | 1 | 4.5 | 0.5 | 1.5 | 0.5 | 0 | 0 |
| M307 | 0.5 | 1.25 | 2 | 0 | 1 | 3.5 | 0.5 | 1.5 | 0.5 | 0 | 0 |
| M308 | 0.5 | 1.25 | 2 | 0 | 1 | 4 | 0.5 | 1 | 0.5 | 0 | 0 |
| M309 | 0.5 | 1.25 | 2 | 0 | 1 | 2.5 | 0.5 | 2.5 | 0.5 | 0 | 0 |
| M310 | 0.5 | 1.25 | 2 | 0 | 1 | 3.5 | 0.5 | 1 | 0.5 | 0 | 0 |
| M311 | 1.1 | 0.65 | 2 | 0 | 1 | 3 | 0.5 | 1.5 | 0.5 | 0 | 0 |
| M312 | 0.5 | 1.25 | 2.5 | 0 | 1 | 4 | 0.5 | 1.5 | 0.5 | 0 | 0 |
| M313 | 0.5 | 1.25 | 2.5 | 0 | 1 | 4 | 0.5 | 1 | 0.5 | 0 | 0 |
| M314 | 0.5 | 1.25 | 2.5 | 0 | 1 | 4.5 | 0.5 | 1.5 | 0.5 | 0 | 0 |
| M315 | 0.5 | 1.25 | 2.5 | 0 | 1 | 4.5 | 0.5 | 1 | 0.5 | 0 | 0 |
| M316 | 0.5 | 1.25 | 2.5 | 0 | 1 | 3.5 | 0.5 | 1.5 | 0.5 | 0 | 0 |
| M317 | 0.5 | 1.25 | 2.5 | 0 | 1 | 3.5 | 0.5 | 1 | 0.5 | 0 | 0 |
| M318 | 1.1 | 0.9 | 2.5 | 0 | 1 | 4 | 0.5 | 2 | 0.5 | 0 | 0 |
| M319 | 0.5 | 1.25 | 3 | 0 | 1 | 4 | 0.5 | 2 | 0.5 | 0 | 0 |
| M320 | 0.5 | 1.25 | 3 | 0 | 1 | 4 | 0.5 | 1.5 | 0.5 | 0 | 0 |
| M321 | 0.5 | 1.25 | 3 | 0 | 1 | 4.5 | 0.5 | 1.5 | 0.5 | 0 | 0 |
| M322 | 0.5 | 1.25 | 3 | 0 | 1 | 5 | 0.5 | 1 | 0.5 | 0 | 0 |
| M323 | 0.5 | 1.25 | 3 | 0 | 1 | 3.5 | 0.5 | 1.5 | 0.5 | 0 | 0 |
| M324 | 0.5 | 1.25 | 3 | 0 | 1 | 3.5 | 0.5 | 1 | 0.5 | 0 | 0 |
| M325 | 1.1 | 0.9 | 3 | 0 | 1 | 4 | 0.5 | 2 | 0.5 | 0 | 0 |
| M326 | 0.5 | 1.25 | 3.5 | 0 | 1 | 3.5 | 0.5 | 1.5 | 0.5 | 0 | 0 |
| M327 | 0.5 | 1.25 | 3.5 | 0 | 1 | 4 | 0.5 | 1.5 | 0.5 | 0 | 0 |
| M328 | 0.5 | 1.25 | 3.5 | 0 | 1 | 4 | 0.5 | 1 | 0.5 | 0 | 0 |
| M329 | 0.5 | 1.25 | 3.5 | 0 | 1 | 4.5 | 0.5 | 1 | 0.5 | 0 | 0 |
| M330 | 0.2 | 0.7 | 1 | 1 | 1 | 3 | 0.65 | 0.65 | 0.5 | 0 | 0 |
| M331 | 0.2 | 0.7 | 2 | 1 | 1 | 3 | 0.65 | 0.65 | 0.5 | 0 | 0 |
| M332 | 0.2 | 0.7 | 3 | 1 | 1 | 3 | 0.65 | 0.65 | 0.5 | 0 | 0 |
| M333 | 0.2 | 0.8 | 1 | 1 | 1 | 3 | 0.65 | 0.65 | 0.5 | 0 | 0 |
| M334 | 0.2 | 0.8 | 2 | 1 | 1 | 3 | 0.65 | 0.65 | 0.5 | 0 | 0 |
| M335 | 0.2 | 0.8 | 3 | 1 | 1 | 3 | 0.65 | 0.65 | 0.5 | 0 | 0 |
| M336 | 0.2 | 0.8 | 4 | 1 | 1 | 3 | 0.65 | 0.65 | 0.5 | 0 | 0 |
| M337 | 0.2 | 0.9 | 1 | 1 | 1 | 3 | 0.65 | 0.65 | 0.5 | 0 | 0 |
| M338 | 0.3 | 0.7 | 1 | 1 | 1 | 3 | 0.65 | 0.65 | 0.5 | 0 | 0 |
| M339 | 0.3 | 0.8 | 1 | 1 | 1 | 3 | 0.65 | 0.65 | 0.5 | 0 | 0 |
| M340 | 0.3 | 0.8 | 2 | 1 | 1 | 3 | 0.65 | 0.65 | 0.5 | 0 | 0 |
| M341 | 0.3 | 0.8 | 3 | 1 | 1 | 3 | 0.65 | 0.65 | 0.5 | 0 | 0 |
| M342 | 0.3 | 0.8 | 4 | 1 | 1 | 3 | 0.65 | 0.65 | 0.5 | 0 | 0 |
| M343 | 0.3 | 0.9 | 1 | 1 | 1 | 3 | 0.65 | 0.65 | 0.5 | 0 | 0 |
| M344 | 0.3 | 0.9 | 2 | 1 | 1 | 3 | 0.65 | 0.65 | 0.5 | 0 | 0 |
| M345 | 0.3 | 0.9 | 3 | 1 | 1 | 3 | 0.65 | 0.65 | 0.5 | 0 | 0 |
| M346 | 0.3 | 0.9 | 4 | 1 | 1 | 3 | 0.65 | 0.65 | 0.5 | 0 | 0 |
| M347 | 0.3 | 0.9 | 5 | 1 | 1 | 3 | 0.65 | 0.65 | 0.5 | 0 | 0 |
| M348 | 0.3 | 1 | 1 | 1 | 1 | 3 | 0.65 | 0.65 | 0.5 | 0 | 0 |
| M349 | 0.3 | 1 | 2 | 1 | 1 | 3 | 0.65 | 0.65 | 0.5 | 0 | 0 |
| M350 | 0.3 | 1 | 3 | 1 | 1 | 3 | 0.65 | 0.65 | 0.5 | 0 | 0 |
| M351 | 0.4 | 0.7 | 1 | 1 | 1 | 3 | 0.65 | 0.65 | 0.5 | 0 | 0 |
| M352 | 0.4 | 0.7 | 2 | 1 | 1 | 3 | 0.65 | 0.65 | 0.5 | 0 | 0 |
| M353 | 0.4 | 0.8 | 1 | 1 | 1 | 3 | 0.65 | 0.65 | 0.5 | 0 | 0 |
| M354 | 0.4 | 0.8 | 2 | 1 | 1 | 3 | 0.65 | 0.65 | 0.5 | 0 | 0 |
| M355 | 0.4 | 0.8 | 3 | 1 | 1 | 3 | 0.65 | 0.65 | 0.5 | 0 | 0 |

TABLE 3-continued

Alloy chemistries in weight percent, balance Fe, for selected alloys evaluated using thermodynamic models which meet thermodynamic criteria

| Alloy | B | C | Cr | Mn | Mo | Nb | Si | Ti | V | W | Zr |
|---|---|---|---|---|---|---|---|---|---|---|---|
| M356 | 0.4 | 0.8 | 4 | 1 | 1 | 3 | 0.65 | 0.65 | 0.5 | 0 | 0 |
| M357 | 0.4 | 0.8 | 5 | 1 | 1 | 3 | 0.65 | 0.65 | 0.5 | 0 | 0 |
| M358 | 0.4 | 0.9 | 1 | 1 | 1 | 3 | 0.65 | 0.65 | 0.5 | 0 | 0 |
| M359 | 0.4 | 0.9 | 2 | 1 | 1 | 3 | 0.65 | 0.65 | 0.5 | 0 | 0 |
| M360 | 0.4 | 0.9 | 3 | 1 | 1 | 3 | 0.65 | 0.65 | 0.5 | 0 | 0 |
| M361 | 0.4 | 0.9 | 4 | 1 | 1 | 3 | 0.65 | 0.65 | 0.5 | 0 | 0 |
| M362 | 0.4 | 0.9 | 5 | 1 | 1 | 3 | 0.65 | 0.65 | 0.5 | 0 | 0 |
| M363 | 0.4 | 0.9 | 6 | 1 | 1 | 3 | 0.65 | 0.65 | 0.5 | 0 | 0 |
| M364 | 0.4 | 1 | 1 | 1 | 1 | 3 | 0.65 | 0.65 | 0.5 | 0 | 0 |
| M365 | 0.4 | 1 | 2 | 1 | 1 | 3 | 0.65 | 0.65 | 0.5 | 0 | 0 |
| M366 | 0.4 | 1 | 3 | 1 | 1 | 3 | 0.65 | 0.65 | 0.5 | 0 | 0 |
| M367 | 0.4 | 1 | 4 | 1 | 1 | 3 | 0.65 | 0.65 | 0.5 | 0 | 0 |
| M368 | 0.4 | 1 | 5 | 1 | 1 | 3 | 0.65 | 0.65 | 0.5 | 0 | 0 |
| M369 | 0.4 | 1 | 6 | 1 | 1 | 3 | 0.65 | 0.65 | 0.5 | 0 | 0 |
| M370 | 0.4 | 1 | 7 | 1 | 1 | 3 | 0.65 | 0.65 | 0.5 | 0 | 0 |
| M371 | 0.4 | 1.1 | 1 | 1 | 1 | 3 | 0.65 | 0.65 | 0.5 | 0 | 0 |
| M372 | 0.4 | 1.1 | 2 | 1 | 1 | 3 | 0.65 | 0.65 | 0.5 | 0 | 0 |
| M373 | 0.4 | 1.1 | 3 | 1 | 1 | 3 | 0.65 | 0.65 | 0.5 | 0 | 0 |
| M374 | 0.4 | 1.1 | 4 | 1 | 1 | 3 | 0.65 | 0.65 | 0.5 | 0 | 0 |
| M375 | 0.4 | 1.1 | 7 | 1 | 1 | 3 | 0.65 | 0.65 | 0.5 | 0 | 0 |
| M376 | 0.4 | 1.1 | 8 | 1 | 1 | 3 | 0.65 | 0.65 | 0.5 | 0 | 0 |
| M377 | 0.4 | 1.1 | 9 | 1 | 1 | 3 | 0.65 | 0.65 | 0.5 | 0 | 0 |
| M378 | 0.3 | 0.7 | 3.5 | 0.75 | 0.75 | 2.75 | 0.5 | 0.5 | 0.5 | 0 | 0 |
| M379 | 0.3 | 0.8 | 3.5 | 0.75 | 0.75 | 2.75 | 0.5 | 0.5 | 0.5 | 0 | 0 |
| M380 | 0.4 | 0.7 | 3.5 | 0.75 | 0.75 | 2.75 | 0.5 | 0.5 | 0.5 | 0 | 0 |
| M381 | 0.4 | 0.8 | 3.5 | 0.75 | 0.75 | 2.75 | 0.5 | 0.5 | 0.5 | 0 | 0 |
| M382 | 0.4 | 0.9 | 3.5 | 0.75 | 0.75 | 2.75 | 0.5 | 0.5 | 0.5 | 0 | 0 |
| M383 | 0.5 | 0.7 | 3.5 | 0.75 | 0.75 | 2.75 | 0.5 | 0.5 | 0.5 | 0 | 0 |
| M384 | 0.5 | 0.8 | 3.5 | 0.75 | 0.75 | 2.75 | 0.5 | 0.5 | 0.5 | 0 | 0 |
| M385 | 0.5 | 0.9 | 3.5 | 0.75 | 0.75 | 2.75 | 0.5 | 0.5 | 0.5 | 0 | 0 |
| M386 | 0.5 | 1 | 3.5 | 0.75 | 0.75 | 2.75 | 0.5 | 0.5 | 0.5 | 0 | 0 |
| M387 | 0.6 | 0.7 | 3.5 | 0.75 | 0.75 | 2.75 | 0.5 | 0.5 | 0.5 | 0 | 0 |
| M388 | 0.6 | 0.8 | 3.5 | 0.75 | 0.75 | 2.75 | 0.5 | 0.5 | 0.5 | 0 | 0 |
| M389 | 0.6 | 0.9 | 3.5 | 0.75 | 0.75 | 2.75 | 0.5 | 0.5 | 0.5 | 0 | 0 |
| M390 | 0.6 | 1 | 3.5 | 0.75 | 0.75 | 2.75 | 0.5 | 0.5 | 0.5 | 0 | 0 |
| M391 | 0.6 | 1.1 | 3.5 | 0.75 | 0.75 | 2.75 | 0.5 | 0.5 | 0.5 | 0 | 0 |
| M392 | 0.7 | 0.9 | 3.5 | 0.75 | 0.75 | 2.75 | 0.5 | 0.5 | 0.5 | 0 | 0 |
| M393 | 0.7 | 1 | 3.5 | 0.75 | 0.75 | 2.75 | 0.5 | 0.5 | 0.5 | 0 | 0 |
| M394 | 0.7 | 1.1 | 3.5 | 0.75 | 0.75 | 2.75 | 0.5 | 0.5 | 0.5 | 0 | 0 |
| M395 | 0.7 | 1.2 | 3.5 | 0.75 | 0.75 | 2.75 | 0.5 | 0.5 | 0.5 | 0 | 0 |
| M396 | 0.7 | 1.3 | 3.5 | 0.75 | 0.75 | 2.75 | 0.5 | 0.5 | 0.5 | 0 | 0 |
| M397 | 0.8 | 0.6 | 3.5 | 0.75 | 0.75 | 2.75 | 0.5 | 0.5 | 0.5 | 0 | 0 |
| M398 | 0.8 | 0.7 | 3.5 | 0.75 | 0.75 | 2.75 | 0.5 | 0.5 | 0.5 | 0 | 0 |
| M399 | 0.8 | 0.8 | 3.5 | 0.75 | 0.75 | 2.75 | 0.5 | 0.5 | 0.5 | 0 | 0 |
| M400 | 0.8 | 0.9 | 3.5 | 0.75 | 0.75 | 2.75 | 0.5 | 0.5 | 0.5 | 0 | 0 |
| M401 | 0.8 | 1 | 3.5 | 0.75 | 0.75 | 2.75 | 0.5 | 0.5 | 0.5 | 0 | 0 |
| M402 | 0.8 | 1.1 | 3.5 | 0.75 | 0.75 | 2.75 | 0.5 | 0.5 | 0.5 | 0 | 0 |
| M403 | 0.8 | 1.2 | 3.5 | 0.75 | 0.75 | 2.75 | 0.5 | 0.5 | 0.5 | 0 | 0 |
| M404 | 0.8 | 1.3 | 3.5 | 0.75 | 0.75 | 2.75 | 0.5 | 0.5 | 0.5 | 0 | 0 |
| M405 | 0.8 | 1.4 | 3.5 | 0.75 | 0.75 | 2.75 | 0.5 | 0.5 | 0.5 | 0 | 0 |
| M406 | 0.9 | 0.6 | 3.5 | 0.75 | 0.75 | 2.75 | 0.5 | 0.5 | 0.5 | 0 | 0 |
| M407 | 0.9 | 0.7 | 3.5 | 0.75 | 0.75 | 2.75 | 0.5 | 0.5 | 0.5 | 0 | 0 |
| M408 | 0.9 | 0.8 | 3.5 | 0.75 | 0.75 | 2.75 | 0.5 | 0.5 | 0.5 | 0 | 0 |
| M409 | 0.9 | 0.9 | 3.5 | 0.75 | 0.75 | 2.75 | 0.5 | 0.5 | 0.5 | 0 | 0 |
| M410 | 0.9 | 1 | 3.5 | 0.75 | 0.75 | 2.75 | 0.5 | 0.5 | 0.5 | 0 | 0 |
| M411 | 0.9 | 1.1 | 3.5 | 0.75 | 0.75 | 2.75 | 0.5 | 0.5 | 0.5 | 0 | 0 |
| M412 | 0.9 | 1.2 | 3.5 | 0.75 | 0.75 | 2.75 | 0.5 | 0.5 | 0.5 | 0 | 0 |
| M413 | 0.9 | 1.3 | 3.5 | 0.75 | 0.75 | 2.75 | 0.5 | 0.5 | 0.5 | 0 | 0 |
| M414 | 0.9 | 1.4 | 3.5 | 0.75 | 0.75 | 2.75 | 0.5 | 0.5 | 0.5 | 0 | 0 |
| M415 | 0.9 | 1.5 | 3.5 | 0.75 | 0.75 | 2.75 | 0.5 | 0.5 | 0.5 | 0 | 0 |
| M416 | 1 | 0.7 | 3.5 | 0.75 | 0.75 | 2.75 | 0.5 | 0.5 | 0.5 | 0 | 0 |
| M417 | 1 | 0.8 | 3.5 | 0.75 | 0.75 | 2.75 | 0.5 | 0.5 | 0.5 | 0 | 0 |
| M418 | 1 | 0.9 | 3.5 | 0.75 | 0.75 | 2.75 | 0.5 | 0.5 | 0.5 | 0 | 0 |
| M419 | 1 | 1 | 3.5 | 0.75 | 0.75 | 2.75 | 0.5 | 0.5 | 0.5 | 0 | 0 |
| M420 | 1 | 1.1 | 3.5 | 0.75 | 0.75 | 2.75 | 0.5 | 0.5 | 0.5 | 0 | 0 |
| M421 | 1 | 1.2 | 3.5 | 0.75 | 0.75 | 2.75 | 0.5 | 0.5 | 0.5 | 0 | 0 |
| M422 | 1 | 1.3 | 3.5 | 0.75 | 0.75 | 2.75 | 0.5 | 0.5 | 0.5 | 0 | 0 |
| M423 | 1 | 1.4 | 3.5 | 0.75 | 0.75 | 2.75 | 0.5 | 0.5 | 0.5 | 0 | 0 |
| M424 | 0.4 | 0.8 | 20 | 0 | 0 | 0 | 0 | 2 | 0 | 0 | 0 |
| M425 | 0.4 | 0.9 | 15 | 0 | 0 | 0 | 0 | 2 | 0 | 0 | 0 |
| M426 | 0.4 | 0.9 | 20 | 0 | 0 | 0 | 0 | 2 | 0 | 0 | 0 |
| M427 | 0.4 | 1 | 15 | 0 | 0 | 0 | 0 | 2 | 0 | 0 | 0 |
| M428 | 0.4 | 1 | 20 | 0 | 0 | 0 | 0 | 2 | 0 | 0 | 0 |
| M429 | 0.4 | 1 | 20 | 0 | 0 | 0 | 0 | 3 | 0 | 0 | 0 |
| M430 | 0.4 | 1.1 | 15 | 0 | 0 | 0 | 0 | 2 | 0 | 0 | 0 |

TABLE 3-continued

Alloy chemistries in weight percent, balance Fe, for selected alloys evaluated using thermodynamic models which meet thermodynamic criteria

| Alloy | B | C | Cr | Mn | Mo | Nb | Si | Ti | V | W | Zr |
|---|---|---|---|---|---|---|---|---|---|---|---|
| M431 | 0.4 | 1.1 | 20 | 0 | 0 | 0 | 0 | 3 | 0 | 0 | 0 |
| M432 | 0.4 | 1.2 | 15 | 0 | 0 | 0 | 0 | 2 | 0 | 0 | 0 |
| M433 | 0.4 | 1.2 | 15 | 0 | 0 | 0 | 0 | 3 | 0 | 0 | 0 |
| M434 | 0.4 | 1.2 | 20 | 0 | 0 | 0 | 0 | 3 | 0 | 0 | 0 |
| M435 | 0.4 | 1.2 | 20 | 0 | 0 | 0 | 0 | 4 | 0 | 0 | 0 |
| M436 | 0.4 | 1.3 | 15 | 0 | 0 | 0 | 0 | 2 | 0 | 0 | 0 |
| M437 | 0.4 | 1.3 | 15 | 0 | 0 | 0 | 0 | 3 | 0 | 0 | 0 |
| M438 | 0.4 | 1.3 | 15 | 0 | 0 | 0 | 0 | 4 | 0 | 0 | 0 |
| M439 | 0.4 | 1.4 | 15 | 0 | 0 | 0 | 0 | 3 | 0 | 0 | 0 |
| M440 | 0.4 | 1.4 | 15 | 0 | 0 | 0 | 0 | 4 | 0 | 0 | 0 |
| M441 | 0.4 | 1.4 | 20 | 0 | 0 | 0 | 0 | 3 | 0 | 0 | 0 |
| M442 | 0.4 | 1.4 | 20 | 0 | 0 | 0 | 0 | 4 | 0 | 0 | 0 |
| M443 | 0.4 | 1.4 | 20 | 0 | 0 | 0 | 0 | 5 | 0 | 0 | 0 |
| M444 | 0.4 | 1.5 | 15 | 0 | 0 | 0 | 0 | 2 | 0 | 0 | 0 |
| M445 | 0.4 | 1.5 | 15 | 0 | 0 | 0 | 0 | 3 | 0 | 0 | 0 |
| M446 | 0.4 | 1.5 | 15 | 0 | 0 | 0 | 0 | 4 | 0 | 0 | 0 |
| M447 | 0.4 | 1.5 | 20 | 0 | 0 | 0 | 0 | 4 | 0 | 0 | 0 |
| M448 | 0.4 | 1.5 | 20 | 0 | 0 | 0 | 0 | 5 | 0 | 0 | 0 |
| M449 | 0.4 | 1.6 | 15 | 0 | 0 | 0 | 0 | 4 | 0 | 0 | 0 |
| M450 | 0.4 | 1.6 | 15 | 0 | 0 | 0 | 0 | 5 | 0 | 0 | 0 |
| M451 | 0.4 | 1.6 | 20 | 0 | 0 | 0 | 0 | 4 | 0 | 0 | 0 |
| M452 | 0.4 | 1.6 | 20 | 0 | 0 | 0 | 0 | 5 | 0 | 0 | 0 |
| M453 | 0.4 | 1.7 | 15 | 0 | 0 | 0 | 0 | 3 | 0 | 0 | 0 |
| M454 | 0.4 | 1.7 | 15 | 0 | 0 | 0 | 0 | 4 | 0 | 0 | 0 |
| M455 | 0.4 | 1.7 | 15 | 0 | 0 | 0 | 0 | 5 | 0 | 0 | 0 |
| M456 | 0.4 | 1.7 | 20 | 0 | 0 | 0 | 0 | 4 | 0 | 0 | 0 |
| M457 | 0.4 | 1.7 | 20 | 0 | 0 | 0 | 0 | 5 | 0 | 0 | 0 |
| M458 | 0.4 | 1.7 | 20 | 0 | 0 | 0 | 0 | 6 | 0 | 0 | 0 |
| M459 | 0.4 | 1.8 | 15 | 0 | 0 | 0 | 0 | 3 | 0 | 0 | 0 |
| M460 | 0.4 | 1.8 | 15 | 0 | 0 | 0 | 0 | 5 | 0 | 0 | 0 |
| M461 | 0.4 | 1.8 | 15 | 0 | 0 | 0 | 0 | 6 | 0 | 0 | 0 |
| M462 | 0.4 | 1.8 | 20 | 0 | 0 | 0 | 0 | 5 | 0 | 0 | 0 |
| M463 | 0.4 | 1.8 | 20 | 0 | 0 | 0 | 0 | 6 | 0 | 0 | 0 |
| M464 | 0.4 | 1.9 | 15 | 0 | 0 | 0 | 0 | 4 | 0 | 0 | 0 |
| M465 | 0.4 | 1.9 | 15 | 0 | 0 | 0 | 0 | 5 | 0 | 0 | 0 |
| M466 | 0.4 | 1.9 | 15 | 0 | 0 | 0 | 0 | 6 | 0 | 0 | 0 |
| M467 | 0.4 | 1.9 | 20 | 0 | 0 | 0 | 0 | 6 | 0 | 0 | 0 |
| M468 | 0.4 | 1.9 | 20 | 0 | 0 | 0 | 0 | 7 | 0 | 0 | 0 |
| M469 | 0.4 | 2 | 15 | 0 | 0 | 0 | 0 | 4 | 0 | 0 | 0 |
| M470 | 0.4 | 2 | 15 | 0 | 0 | 0 | 0 | 6 | 0 | 0 | 0 |
| M471 | 0.4 | 2 | 20 | 0 | 0 | 0 | 0 | 6 | 0 | 0 | 0 |
| M472 | 0.4 | 2 | 20 | 0 | 0 | 0 | 0 | 7 | 0 | 0 | 0 |
| M473 | 0.5 | 0.9 | 20 | 0 | 0 | 0 | 0 | 2 | 0 | 0 | 0 |
| M474 | 0.5 | 1 | 20 | 0 | 0 | 0 | 0 | 2 | 0 | 0 | 0 |
| M475 | 0.5 | 1.1 | 15 | 0 | 0 | 0 | 0 | 2 | 0 | 0 | 0 |
| M476 | 0.5 | 1.1 | 20 | 0 | 0 | 0 | 0 | 2 | 0 | 0 | 0 |
| M477 | 0.5 | 1.1 | 20 | 0 | 0 | 0 | 0 | 3 | 0 | 0 | 0 |
| M478 | 0.5 | 1.2 | 20 | 0 | 0 | 0 | 0 | 3 | 0 | 0 | 0 |
| M479 | 0.5 | 1.3 | 15 | 0 | 0 | 0 | 0 | 3 | 0 | 0 | 0 |
| M480 | 0.5 | 1.3 | 20 | 0 | 0 | 0 | 0 | 3 | 0 | 0 | 0 |
| M481 | 0.5 | 1.3 | 20 | 0 | 0 | 0 | 0 | 4 | 0 | 0 | 0 |
| M482 | 0.5 | 1.4 | 20 | 0 | 0 | 0 | 0 | 4 | 0 | 0 | 0 |
| M483 | 0.5 | 1.5 | 15 | 0 | 0 | 0 | 0 | 4 | 0 | 0 | 0 |
| M484 | 0.5 | 1.5 | 20 | 0 | 0 | 0 | 0 | 4 | 0 | 0 | 0 |
| M485 | 0.5 | 1.5 | 20 | 0 | 0 | 0 | 0 | 5 | 0 | 0 | 0 |
| M486 | 0.5 | 1.6 | 20 | 0 | 0 | 0 | 0 | 4 | 0 | 0 | 0 |
| M487 | 0.5 | 1.6 | 20 | 0 | 0 | 0 | 0 | 5 | 0 | 0 | 0 |
| M488 | 0.5 | 1.7 | 15 | 0 | 0 | 0 | 0 | 5 | 0 | 0 | 0 |
| M489 | 0.5 | 1.7 | 20 | 0 | 0 | 0 | 0 | 5 | 0 | 0 | 0 |
| M490 | 0.5 | 1.7 | 20 | 0 | 0 | 0 | 0 | 6 | 0 | 0 | 0 |
| M491 | 0.5 | 1.8 | 20 | 0 | 0 | 0 | 0 | 5 | 0 | 0 | 0 |
| M492 | 0.5 | 1.8 | 20 | 0 | 0 | 0 | 0 | 6 | 0 | 0 | 0 |
| M493 | 0.5 | 1.9 | 20 | 0 | 0 | 0 | 0 | 5 | 0 | 0 | 0 |
| M494 | 0.5 | 1.9 | 20 | 0 | 0 | 0 | 0 | 6 | 0 | 0 | 0 |
| M495 | 0.5 | 2 | 20 | 0 | 0 | 0 | 0 | 6 | 0 | 0 | 0 |
| M496 | 0.5 | 2 | 20 | 0 | 0 | 0 | 0 | 7 | 0 | 0 | 0 |
| M497 | 0.6 | 0.9 | 20 | 0 | 0 | 0 | 0 | 2 | 0 | 0 | 0 |
| M498 | 0.6 | 1 | 20 | 0 | 0 | 0 | 0 | 2 | 0 | 0 | 0 |
| M499 | 0.6 | 1.1 | 20 | 0 | 0 | 0 | 0 | 3 | 0 | 0 | 0 |
| M500 | 0.6 | 1.2 | 20 | 0 | 0 | 0 | 0 | 3 | 0 | 0 | 0 |
| M501 | 0.6 | 1.3 | 20 | 0 | 0 | 0 | 0 | 3 | 0 | 0 | 0 |
| M502 | 0.6 | 1.3 | 20 | 0 | 0 | 0 | 0 | 4 | 0 | 0 | 0 |
| M503 | 0.6 | 1.4 | 15 | 0 | 0 | 0 | 0 | 3 | 0 | 0 | 0 |
| M504 | 0.6 | 1.4 | 15 | 0 | 0 | 0 | 0 | 4 | 0 | 0 | 0 |
| M505 | 0.6 | 1.4 | 15 | 0 | 0 | 0 | 0 | 5 | 0 | 0 | 0 |

TABLE 3-continued

Alloy chemistries in weight percent, balance Fe, for selected alloys evaluated using thermodynamic models which meet thermodynamic criteria

| Alloy | B | C | Cr | Mn | Mo | Nb | Si | Ti | V | W | Zr |
|---|---|---|---|---|---|---|---|---|---|---|---|
| M506 | 0.6 | 1.4 | 20 | 0 | 0 | 0 | 0 | 4 | 0 | 0 | 0 |
| M507 | 0.6 | 1.5 | 15 | 0 | 0 | 0 | 0 | 3 | 0 | 0 | 0 |
| M508 | 0.6 | 1.5 | 15 | 0 | 0 | 0 | 0 | 4 | 0 | 0 | 0 |
| M509 | 0.6 | 1.5 | 15 | 0 | 0 | 0 | 0 | 6 | 0 | 0 | 0 |
| M510 | 0.6 | 1.5 | 20 | 0 | 0 | 0 | 0 | 4 | 0 | 0 | 0 |
| M511 | 0.6 | 1.5 | 20 | 0 | 0 | 0 | 0 | 5 | 0 | 0 | 0 |
| M512 | 0.6 | 1.6 | 15 | 0 | 0 | 0 | 0 | 3 | 0 | 0 | 0 |
| M513 | 0.6 | 1.6 | 15 | 0 | 0 | 0 | 0 | 4 | 0 | 0 | 0 |
| M514 | 0.6 | 1.6 | 15 | 0 | 0 | 0 | 0 | 5 | 0 | 0 | 0 |
| M515 | 0.6 | 1.6 | 15 | 0 | 0 | 0 | 0 | 6 | 0 | 0 | 0 |
| M516 | 0.6 | 1.6 | 20 | 0 | 0 | 0 | 0 | 5 | 0 | 0 | 0 |
| M517 | 0.6 | 1.7 | 15 | 0 | 0 | 0 | 0 | 4 | 0 | 0 | 0 |
| M518 | 0.6 | 1.7 | 15 | 0 | 0 | 0 | 0 | 5 | 0 | 0 | 0 |
| M519 | 0.6 | 1.7 | 20 | 0 | 0 | 0 | 0 | 5 | 0 | 0 | 0 |
| M520 | 0.6 | 1.7 | 20 | 0 | 0 | 0 | 0 | 6 | 0 | 0 | 0 |
| M521 | 0.6 | 1.8 | 15 | 0 | 0 | 0 | 0 | 4 | 0 | 0 | 0 |
| M522 | 0.6 | 1.8 | 15 | 0 | 0 | 0 | 0 | 5 | 0 | 0 | 0 |
| M523 | 0.6 | 1.8 | 15 | 0 | 0 | 0 | 0 | 6 | 0 | 0 | 0 |
| M524 | 0.6 | 1.8 | 15 | 0 | 0 | 0 | 0 | 7 | 0 | 0 | 0 |
| M525 | 0.6 | 1.8 | 20 | 0 | 0 | 0 | 0 | 5 | 0 | 0 | 0 |
| M526 | 0.6 | 1.8 | 20 | 0 | 0 | 0 | 0 | 6 | 0 | 0 | 0 |
| M527 | 0.6 | 1.9 | 15 | 0 | 0 | 0 | 0 | 4 | 0 | 0 | 0 |
| M528 | 0.6 | 1.9 | 15 | 0 | 0 | 0 | 0 | 5 | 0 | 0 | 0 |
| M529 | 0.6 | 1.9 | 15 | 0 | 0 | 0 | 0 | 6 | 0 | 0 | 0 |
| M530 | 0.6 | 1.9 | 20 | 0 | 0 | 0 | 0 | 6 | 0 | 0 | 0 |
| M531 | 0.6 | 1.9 | 20 | 0 | 0 | 0 | 0 | 7 | 0 | 0 | 0 |
| M532 | 0.6 | 2 | 15 | 0 | 0 | 0 | 0 | 5 | 0 | 0 | 0 |
| M533 | 0.6 | 2 | 15 | 0 | 0 | 0 | 0 | 6 | 0 | 0 | 0 |
| M534 | 0.6 | 2 | 15 | 0 | 0 | 0 | 0 | 7 | 0 | 0 | 0 |
| M535 | 0.6 | 2 | 15 | 0 | 0 | 0 | 0 | 8 | 0 | 0 | 0 |
| M536 | 0.6 | 2 | 20 | 0 | 0 | 0 | 0 | 6 | 0 | 0 | 0 |
| M537 | 0.6 | 2 | 20 | 0 | 0 | 0 | 0 | 7 | 0 | 0 | 0 |
| M538 | 0.7 | 0.8 | 20 | 0 | 0 | 0 | 0 | 2 | 0 | 0 | 0 |
| M539 | 0.7 | 0.9 | 15 | 0 | 0 | 0 | 0 | 2 | 0 | 0 | 0 |
| M540 | 0.7 | 0.9 | 15 | 0 | 0 | 0 | 0 | 3 | 0 | 0 | 0 |
| M541 | 0.7 | 0.9 | 20 | 0 | 0 | 0 | 0 | 2 | 0 | 0 | 0 |
| M542 | 0.7 | 1 | 15 | 0 | 0 | 0 | 0 | 2 | 0 | 0 | 0 |
| M543 | 0.7 | 1 | 20 | 0 | 0 | 0 | 0 | 3 | 0 | 0 | 0 |
| M544 | 0.7 | 1.1 | 15 | 0 | 0 | 0 | 0 | 2 | 0 | 0 | 0 |
| M545 | 0.7 | 1.1 | 15 | 0 | 0 | 0 | 0 | 3 | 0 | 0 | 0 |
| M546 | 0.7 | 1.1 | 15 | 0 | 0 | 0 | 0 | 4 | 0 | 0 | 0 |
| M547 | 0.7 | 1.1 | 20 | 0 | 0 | 0 | 0 | 3 | 0 | 0 | 0 |
| M548 | 0.7 | 1.2 | 15 | 0 | 0 | 0 | 0 | 2 | 0 | 0 | 0 |
| M549 | 0.7 | 1.2 | 15 | 0 | 0 | 0 | 0 | 3 | 0 | 0 | 0 |
| M550 | 0.7 | 1.2 | 20 | 0 | 0 | 0 | 0 | 3 | 0 | 0 | 0 |
| M551 | 0.7 | 1.3 | 15 | 0 | 0 | 0 | 0 | 3 | 0 | 0 | 0 |
| M552 | 0.7 | 1.3 | 15 | 0 | 0 | 0 | 0 | 4 | 0 | 0 | 0 |
| M553 | 0.7 | 1.3 | 15 | 0 | 0 | 0 | 0 | 5 | 0 | 0 | 0 |
| M554 | 0.7 | 1.3 | 20 | 0 | 0 | 0 | 0 | 4 | 0 | 0 | 0 |
| M555 | 0.7 | 1.4 | 15 | 0 | 0 | 0 | 0 | 3 | 0 | 0 | 0 |
| M556 | 0.7 | 1.4 | 15 | 0 | 0 | 0 | 0 | 4 | 0 | 0 | 0 |
| M557 | 0.7 | 1.4 | 20 | 0 | 0 | 0 | 0 | 4 | 0 | 0 | 0 |
| M558 | 0.7 | 1.5 | 15 | 0 | 0 | 0 | 0 | 3 | 0 | 0 | 0 |
| M559 | 0.7 | 1.5 | 15 | 0 | 0 | 0 | 0 | 4 | 0 | 0 | 0 |
| M560 | 0.7 | 1.5 | 15 | 0 | 0 | 0 | 0 | 5 | 0 | 0 | 0 |
| M561 | 0.7 | 1.5 | 20 | 0 | 0 | 0 | 0 | 5 | 0 | 0 | 0 |
| M562 | 0.7 | 1.6 | 15 | 0 | 0 | 0 | 0 | 4 | 0 | 0 | 0 |
| M563 | 0.7 | 1.6 | 20 | 0 | 0 | 0 | 0 | 5 | 0 | 0 | 0 |
| M564 | 0.7 | 1.7 | 15 | 0 | 0 | 0 | 0 | 4 | 0 | 0 | 0 |
| M565 | 0.7 | 1.7 | 15 | 0 | 0 | 0 | 0 | 5 | 0 | 0 | 0 |
| M566 | 0.7 | 1.7 | 15 | 0 | 0 | 0 | 0 | 6 | 0 | 0 | 0 |
| M567 | 0.7 | 1.7 | 20 | 0 | 0 | 0 | 0 | 5 | 0 | 0 | 0 |
| M568 | 0.7 | 1.8 | 15 | 0 | 0 | 0 | 0 | 4 | 0 | 0 | 0 |
| M569 | 0.7 | 1.8 | 15 | 0 | 0 | 0 | 0 | 5 | 0 | 0 | 0 |
| M570 | 0.7 | 1.8 | 20 | 0 | 0 | 0 | 0 | 6 | 0 | 0 | 0 |
| M571 | 0.6 | 1.5 | 15 | 0 | 0 | 0 | 0 | 0 | 6 | 0 | 0 |
| M572 | 0.7 | 1.9 | 15 | 0 | 0 | 0 | 0 | 5 | 0 | 0 | 0 |
| M573 | 0.7 | 1.9 | 20 | 0 | 0 | 0 | 0 | 6 | 0 | 0 | 0 |
| M574 | 0.7 | 2 | 15 | 0 | 0 | 0 | 0 | 5 | 0 | 0 | 0 |
| M575 | 0.7 | 2 | 15 | 0 | 0 | 0 | 0 | 6 | 0 | 0 | 0 |
| M576 | 0.7 | 2 | 20 | 0 | 0 | 0 | 0 | 6 | 0 | 0 | 0 |
| M577 | 0.7 | 2 | 20 | 0 | 0 | 0 | 0 | 7 | 0 | 0 | 0 |
| M578 | 0.8 | 0.9 | 20 | 0 | 0 | 0 | 0 | 2 | 0 | 0 | 0 |
| M579 | 0.8 | 1.1 | 15 | 0 | 0 | 0 | 0 | 2 | 0 | 0 | 0 |
| M580 | 0.7 | 0.8 | 15 | 0 | 0 | 0 | 0 | 0 | 3 | 0 | 0 |

TABLE 3-continued

Alloy chemistries in weight percent, balance Fe, for selected alloys evaluated using thermodynamic models which meet thermodynamic criteria

| Alloy | B | C | Cr | Mn | Mo | Nb | Si | Ti | V | W | Zr |
|---|---|---|---|---|---|---|---|---|---|---|---|
| M581 | 0.8 | 1.4 | 15 | 0 | 0 | 0 | 0 | 3 | 0 | 0 | 0 |
| M582 | 0.7 | 0.8 | 15 | 0 | 0 | 0 | 0 | 0 | 4 | 0 | 0 |
| M583 | 0.7 | 0.8 | 15 | 0 | 0 | 0 | 0 | 0 | 5 | 0 | 0 |
| M584 | 0.8 | 1.4 | 20 | 0 | 0 | 0 | 0 | 4 | 0 | 0 | 0 |
| M585 | 0.7 | 0.9 | 15 | 0 | 0 | 0 | 0 | 0 | 4 | 0 | 0 |
| M586 | 0.8 | 1.6 | 20 | 0 | 0 | 0 | 0 | 5 | 0 | 0 | 0 |
| M587 | 0.7 | 1 | 15 | 0 | 0 | 0 | 0 | 0 | 4 | 0 | 0 |
| M588 | 0.8 | 1.7 | 15 | 0 | 0 | 0 | 0 | 4 | 0 | 0 | 0 |
| M589 | 0.8 | 1.8 | 20 | 0 | 0 | 0 | 0 | 6 | 0 | 0 | 0 |
| M590 | 0.8 | 1.9 | 15 | 0 | 0 | 0 | 0 | 5 | 0 | 0 | 0 |
| M591 | 0.8 | 1.9 | 20 | 0 | 0 | 0 | 0 | 6 | 0 | 0 | 0 |
| M592 | 0.8 | 2 | 15 | 0 | 0 | 0 | 0 | 5 | 0 | 0 | 0 |
| M593 | 0.7 | 1.2 | 20 | 0 | 0 | 0 | 0 | 0 | 9 | 0 | 0 |
| M594 | 0.7 | 1.2 | 20 | 0 | 0 | 0 | 0 | 0 | 10 | 0 | 0 |
| M595 | 0.7 | 1.3 | 20 | 0 | 0 | 0 | 0 | 0 | 9 | 0 | 0 |
| M596 | 0.7 | 1.3 | 20 | 0 | 0 | 0 | 0 | 0 | 10 | 0 | 0 |
| M597 | 0.7 | 1.4 | 15 | 0 | 0 | 0 | 0 | 0 | 6 | 0 | 0 |
| M598 | 0.7 | 1.4 | 15 | 0 | 0 | 0 | 0 | 0 | 7 | 0 | 0 |
| M599 | 0.7 | 1.5 | 15 | 0 | 0 | 0 | 0 | 0 | 7 | 0 | 0 |
| M600 | 0.7 | 1.6 | 15 | 0 | 0 | 0 | 0 | 0 | 7 | 0 | 0 |
| M601 | 0.7 | 2 | 15 | 0 | 0 | 0 | 0 | 0 | 10 | 0 | 0 |
| M602 | 0.8 | 0.8 | 15 | 0 | 0 | 0 | 0 | 0 | 4 | 0 | 0 |
| M603 | 0.8 | 0.8 | 15 | 0 | 0 | 0 | 0 | 0 | 5 | 0 | 0 |
| M604 | 0.8 | 0.8 | 15 | 0 | 0 | 0 | 0 | 0 | 6 | 0 | 0 |
| M605 | 0.9 | 1.9 | 15 | 0 | 0 | 0 | 0 | 5 | 0 | 0 | 0 |
| M606 | 0.8 | 0.8 | 20 | 0 | 0 | 0 | 0 | 0 | 7 | 0 | 0 |
| M607 | 0.8 | 0.9 | 15 | 0 | 0 | 0 | 0 | 0 | 4 | 0 | 0 |
| M608 | 0.8 | 0.9 | 15 | 0 | 0 | 0 | 0 | 0 | 5 | 0 | 0 |
| M609 | 0.4 | 0.8 | 15 | 0 | 0 | 5 | 0 | 0 | 0 | 0 | 0 |
| M610 | 0.4 | 0.8 | 20 | 0 | 0 | 2 | 0 | 0 | 0 | 0 | 0 |
| M611 | 0.4 | 0.8 | 20 | 0 | 0 | 3 | 0 | 0 | 0 | 0 | 0 |
| M612 | 0.4 | 0.8 | 20 | 0 | 0 | 4 | 0 | 0 | 0 | 0 | 0 |
| M613 | 0.4 | 0.8 | 20 | 0 | 0 | 5 | 0 | 0 | 0 | 0 | 0 |
| M614 | 0.4 | 0.9 | 15 | 0 | 0 | 2 | 0 | 0 | 0 | 0 | 0 |
| M615 | 0.4 | 0.9 | 15 | 0 | 0 | 6 | 0 | 0 | 0 | 0 | 0 |
| M616 | 0.5 | 1.25 | 3.5 | 0 | 1 | 3 | 0.5 | 1.5 | 0.5 | 0 | 0 |
| M617 | 0.5 | 1.25 | 3.5 | 0 | 1 | 5 | 0.5 | 1 | 0.5 | 0 | 0 |
| M618 | 0.5 | 1.25 | 3.5 | 0 | 1 | 4.5 | 0.5 | 1.5 | 0.5 | 0 | 0 |
| M619 | 0.5 | 1.25 | 3.5 | 0 | 1 | 2.5 | 0.5 | 1.5 | 0.5 | 0 | 0 |
| M620 | 0.5 | 1.25 | 3.5 | 0 | 1 | 3.5 | 0.5 | 2 | 0.5 | 0 | 0 |
| M621 | 0.5 | 1.25 | 4 | 0 | 1 | 2.5 | 0.5 | 1.5 | 0.5 | 0 | 0 |
| M622 | 0.5 | 1.25 | 4 | 0 | 1 | 3.5 | 0.5 | 1 | 0.5 | 0 | 0 |
| M623 | 0.5 | 1.25 | 4 | 0 | 1 | 3 | 0.5 | 1 | 0.5 | 0 | 0 |
| M624 | 0.5 | 1.25 | 4 | 0 | 1 | 3 | 0.5 | 1.5 | 0.5 | 0 | 0 |
| M625 | 0.5 | 1.25 | 4 | 0 | 1 | 2.5 | 0.5 | 1 | 0.5 | 0 | 0 |
| M626 | 0.5 | 1.25 | 4 | 0 | 1 | 3.5 | 0.5 | 1.5 | 0.5 | 0 | 0 |
| M627 | 0.5 | 1.25 | 4 | 0 | 1 | 5 | 0.5 | 1 | 0.5 | 0 | 0 |
| M628 | 0.5 | 1.25 | 4 | 0 | 1 | 4 | 0.5 | 1.5 | 0.5 | 0 | 0 |
| M629 | 0.5 | 1.25 | 4 | 0 | 1 | 4.5 | 0.5 | 1.5 | 0.5 | 0 | 0 |
| M630 | 0.5 | 1.25 | 4.5 | 0 | 1 | 2.5 | 0.5 | 1 | 0.5 | 0 | 0 |
| M631 | 0.5 | 1.25 | 4.5 | 0 | 1 | 3 | 0.5 | 1 | 0.5 | 0 | 0 |
| M632 | 0.5 | 1.25 | 4.5 | 0 | 1 | 3.5 | 0.5 | 1 | 0.5 | 0 | 0 |
| M633 | 0.5 | 1.25 | 4.5 | 0 | 1 | 4 | 0.5 | 1 | 0.5 | 0 | 0 |
| M634 | 0.5 | 1.25 | 4.5 | 0 | 1 | 4.5 | 0.5 | 1 | 0.5 | 0 | 0 |
| M635 | 0.5 | 1.25 | 4.5 | 0 | 1 | 5 | 0.5 | 1 | 0.5 | 0 | 0 |
| M636 | 0.5 | 1.25 | 4.5 | 0 | 1 | 3.5 | 0.5 | 1.5 | 0.5 | 0 | 0 |
| M637 | 0.5 | 1.25 | 4.5 | 0 | 1 | 4 | 0.5 | 1.5 | 0.5 | 0 | 0 |
| M638 | 0.5 | 1.25 | 4.5 | 0 | 1 | 4.5 | 0.5 | 1.5 | 0.5 | 0 | 0 |
| M639 | 0.5 | 1.25 | 5 | 0 | 1 | 3 | 0.5 | 0.5 | 0.5 | 0 | 0 |
| M640 | 0.5 | 1.25 | 5 | 0 | 1 | 3.5 | 0.5 | 0.5 | 0.5 | 0 | 0 |
| M641 | 0.5 | 1.25 | 5 | 0 | 1 | 3.5 | 0.5 | 1 | 0.5 | 0 | 0 |
| M642 | 0.5 | 1.25 | 5 | 0 | 1 | 4 | 0.5 | 1.5 | 0.5 | 0 | 0 |
| M643 | 0.8 | 1 | 20 | 0 | 0 | 0 | 0 | 0 | 9 | 0 | 0 |
| M644 | 0.4 | 0.9 | 20 | 0 | 0 | 3 | 0 | 0 | 0 | 0 | 0 |
| M645 | 0.8 | 1 | 20 | 0 | 0 | 0 | 0 | 0 | 10 | 0 | 0 |
| M646 | 0.4 | 0.9 | 20 | 0 | 0 | 4 | 0 | 0 | 0 | 0 | 0 |
| M647 | 0.4 | 0.9 | 20 | 0 | 0 | 5 | 0 | 0 | 0 | 0 | 0 |
| M648 | 0.4 | 0.9 | 20 | 0 | 0 | 6 | 0 | 0 | 0 | 0 | 0 |
| M649 | 0.4 | 1 | 15 | 0 | 0 | 2 | 0 | 0 | 0 | 0 | 0 |
| M650 | 0.4 | 1 | 15 | 0 | 0 | 3 | 0 | 0 | 0 | 0 | 0 |
| M651 | 0.4 | 1 | 15 | 0 | 0 | 7 | 0 | 0 | 0 | 0 | 0 |
| M652 | 0.4 | 1 | 20 | 0 | 0 | 3 | 0 | 0 | 0 | 0 | 0 |
| M653 | 0.4 | 1 | 20 | 0 | 0 | 4 | 0 | 0 | 0 | 0 | 0 |
| M654 | 0.8 | 1.1 | 20 | 0 | 0 | 0 | 0 | 0 | 8 | 0 | 0 |
| M655 | 0.4 | 1 | 20 | 0 | 0 | 5 | 0 | 0 | 0 | 0 | 0 |

TABLE 3-continued

Alloy chemistries in weight percent, balance Fe, for selected alloys evaluated using thermodynamic models which meet thermodynamic criteria

| Alloy | B | C | Cr | Mn | Mo | Nb | Si | Ti | V | W | Zr |
|---|---|---|---|---|---|---|---|---|---|---|---|
| M656 | 0.8 | 1.1 | 20 | 0 | 0 | 0 | 0 | 0 | 9 | 0 | 0 |
| M657 | 0.4 | 1 | 20 | 0 | 0 | 6 | 0 | 0 | 0 | 0 | 0 |
| M658 | 0.8 | 1.1 | 20 | 0 | 0 | 0 | 0 | 0 | 10 | 0 | 0 |
| M659 | 0.4 | 1.1 | 15 | 0 | 0 | 2 | 0 | 0 | 0 | 0 | 0 |
| M660 | 0.4 | 1.1 | 15 | 0 | 0 | 3 | 0 | 0 | 0 | 0 | 0 |
| M661 | 0.4 | 1.1 | 15 | 0 | 0 | 4 | 0 | 0 | 0 | 0 | 0 |
| M662 | 0.8 | 1.2 | 15 | 0 | 0 | 0 | 0 | 0 | 6 | 0 | 0 |
| M663 | 0.8 | 1.2 | 15 | 0 | 0 | 0 | 0 | 0 | 7 | 0 | 0 |
| M664 | 0.8 | 1.2 | 15 | 0 | 0 | 0 | 0 | 0 | 8 | 0 | 0 |
| M665 | 0.8 | 1.2 | 15 | 0 | 0 | 0 | 0 | 0 | 9 | 0 | 0 |
| M666 | 0.4 | 1.1 | 15 | 0 | 0 | 8 | 0 | 0 | 0 | 0 | 0 |
| M667 | 0.8 | 1.2 | 15 | 0 | 0 | 0 | 0 | 0 | 10 | 0 | 0 |
| M668 | 0.4 | 1.1 | 20 | 0 | 0 | 4 | 0 | 0 | 0 | 0 | 0 |
| M669 | 0.4 | 1.1 | 20 | 0 | 0 | 5 | 0 | 0 | 0 | 0 | 0 |
| M670 | 0.4 | 1.1 | 20 | 0 | 0 | 6 | 0 | 0 | 0 | 0 | 0 |
| M671 | 0.4 | 1.1 | 20 | 0 | 0 | 7 | 0 | 0 | 0 | 0 | 0 |
| M672 | 0.4 | 1.2 | 15 | 0 | 0 | 2 | 0 | 0 | 0 | 0 | 0 |
| M673 | 0.8 | 1.2 | 20 | 0 | 0 | 0 | 0 | 0 | 9 | 0 | 0 |
| M674 | 0.4 | 1.2 | 15 | 0 | 0 | 3 | 0 | 0 | 0 | 0 | 0 |
| M675 | 0.8 | 1.2 | 20 | 0 | 0 | 0 | 0 | 0 | 10 | 0 | 0 |
| M676 | 0.4 | 1.2 | 15 | 0 | 0 | 4 | 0 | 0 | 0 | 0 | 0 |
| M677 | 0.4 | 1.2 | 15 | 0 | 0 | 5 | 0 | 0 | 0 | 0 | 0 |
| M678 | 0.4 | 1.2 | 15 | 0 | 0 | 8 | 0 | 0 | 0 | 0 | 0 |
| M679 | 0.8 | 1.3 | 15 | 0 | 0 | 0 | 0 | 0 | 6 | 0 | 0 |
| M680 | 0.8 | 1.3 | 15 | 0 | 0 | 0 | 0 | 0 | 7 | 0 | 0 |
| M681 | 0.8 | 1.3 | 15 | 0 | 0 | 0 | 0 | 0 | 8 | 0 | 0 |
| M682 | 0.8 | 1.3 | 15 | 0 | 0 | 0 | 0 | 0 | 9 | 0 | 0 |
| M683 | 0.4 | 1.2 | 20 | 0 | 0 | 5 | 0 | 0 | 0 | 0 | 0 |
| M684 | 0.4 | 1.2 | 20 | 0 | 0 | 6 | 0 | 0 | 0 | 0 | 0 |
| M685 | 0.4 | 1.2 | 20 | 0 | 0 | 7 | 0 | 0 | 0 | 0 | 0 |
| M686 | 0.4 | 1.2 | 20 | 0 | 0 | 8 | 0 | 0 | 0 | 0 | 0 |
| M687 | 0.4 | 1.3 | 15 | 0 | 0 | 3 | 0 | 0 | 0 | 0 | 0 |
| M688 | 0.4 | 1.3 | 15 | 0 | 0 | 4 | 0 | 0 | 0 | 0 | 0 |
| M689 | 0.4 | 1.3 | 15 | 0 | 0 | 5 | 0 | 0 | 0 | 0 | 0 |
| M690 | 0.4 | 1.3 | 15 | 0 | 0 | 6 | 0 | 0 | 0 | 0 | 0 |
| M691 | 0.8 | 1.3 | 20 | 0 | 0 | 0 | 0 | 0 | 10 | 0 | 0 |
| M692 | 0.8 | 1.4 | 15 | 0 | 0 | 0 | 0 | 0 | 7 | 0 | 0 |
| M693 | 0.4 | 1.3 | 20 | 0 | 0 | 6 | 0 | 0 | 0 | 0 | 0 |
| M694 | 0.8 | 1.4 | 15 | 0 | 0 | 0 | 0 | 0 | 8 | 0 | 0 |
| M695 | 0.4 | 1.3 | 20 | 0 | 0 | 7 | 0 | 0 | 0 | 0 | 0 |
| M696 | 0.8 | 1.4 | 15 | 0 | 0 | 0 | 0 | 0 | 9 | 0 | 0 |
| M697 | 0.4 | 1.3 | 20 | 0 | 0 | 8 | 0 | 0 | 0 | 0 | 0 |
| M698 | 0.4 | 1.4 | 15 | 0 | 0 | 4 | 0 | 0 | 0 | 0 | 0 |
| M699 | 0.4 | 1.4 | 15 | 0 | 0 | 5 | 0 | 0 | 0 | 0 | 0 |
| M700 | 0.4 | 1.4 | 15 | 0 | 0 | 6 | 0 | 0 | 0 | 0 | 0 |
| M701 | 0.4 | 1.4 | 15 | 0 | 0 | 7 | 0 | 0 | 0 | 0 | 0 |
| M702 | 0.8 | 1.4 | 20 | 0 | 0 | 0 | 0 | 0 | 10 | 0 | 0 |
| M703 | 0.4 | 1.4 | 20 | 0 | 0 | 7 | 0 | 0 | 0 | 0 | 0 |
| M704 | 0.4 | 1.4 | 20 | 0 | 0 | 8 | 0 | 0 | 0 | 0 | 0 |
| M705 | 0.8 | 1.5 | 15 | 0 | 0 | 0 | 0 | 0 | 7 | 0 | 0 |
| M706 | 0.8 | 1.5 | 15 | 0 | 0 | 0 | 0 | 0 | 8 | 0 | 0 |
| M707 | 0.4 | 1.5 | 15 | 0 | 0 | 5 | 0 | 0 | 0 | 0 | 0 |
| M708 | 0.4 | 1.5 | 15 | 0 | 0 | 6 | 0 | 0 | 0 | 0 | 0 |
| M709 | 0.4 | 1.5 | 15 | 0 | 0 | 7 | 0 | 0 | 0 | 0 | 0 |
| M710 | 0.4 | 1.5 | 15 | 0 | 0 | 8 | 0 | 0 | 0 | 0 | 0 |
| M711 | 0.4 | 1.5 | 20 | 0 | 0 | 8 | 0 | 0 | 0 | 0 | 0 |
| M712 | 0.4 | 1.6 | 15 | 0 | 0 | 5 | 0 | 0 | 0 | 0 | 0 |
| M713 | 0.4 | 1.6 | 15 | 0 | 0 | 6 | 0 | 0 | 0 | 0 | 0 |
| M714 | 0.8 | 1.6 | 15 | 0 | 0 | 0 | 0 | 0 | 8 | 0 | 0 |
| M715 | 0.4 | 1.6 | 15 | 0 | 0 | 7 | 0 | 0 | 0 | 0 | 0 |
| M716 | 0.4 | 1.6 | 15 | 0 | 0 | 8 | 0 | 0 | 0 | 0 | 0 |
| M717 | 0.4 | 1.7 | 15 | 0 | 0 | 6 | 0 | 0 | 0 | 0 | 0 |
| M718 | 0.4 | 1.7 | 15 | 0 | 0 | 7 | 0 | 0 | 0 | 0 | 0 |
| M719 | 0.4 | 1.7 | 15 | 0 | 0 | 8 | 0 | 0 | 0 | 0 | 0 |
| M720 | 0.8 | 1.7 | 15 | 0 | 0 | 0 | 0 | 0 | 8 | 0 | 0 |
| M721 | 0.4 | 1.8 | 15 | 0 | 0 | 7 | 0 | 0 | 0 | 0 | 0 |
| M722 | 0.4 | 1.8 | 15 | 0 | 0 | 8 | 0 | 0 | 0 | 0 | 0 |
| M723 | 0.8 | 1.8 | 15 | 0 | 0 | 0 | 0 | 0 | 10 | 0 | 0 |
| M724 | 0.4 | 1.9 | 15 | 0 | 0 | 8 | 0 | 0 | 0 | 0 | 0 |
| M725 | 0.8 | 1.9 | 15 | 0 | 0 | 0 | 0 | 0 | 9 | 0 | 0 |
| M726 | 0.8 | 1.9 | 15 | 0 | 0 | 0 | 0 | 0 | 10 | 0 | 0 |
| M727 | 0.5 | 0.8 | 15 | 0 | 0 | 2 | 0 | 0 | 0 | 0 | 0 |
| M728 | 0.5 | 0.8 | 15 | 0 | 0 | 3 | 0 | 0 | 0 | 0 | 0 |
| M729 | 0.5 | 0.8 | 15 | 0 | 0 | 5 | 0 | 0 | 0 | 0 | 0 |
| M730 | 0.5 | 0.8 | 20 | 0 | 0 | 2 | 0 | 0 | 0 | 0 | 0 |

TABLE 3-continued

Alloy chemistries in weight percent, balance Fe, for selected alloys evaluated using thermodynamic models which meet thermodynamic criteria

| Alloy | B | C | Cr | Mn | Mo | Nb | Si | Ti | V | W | Zr |
|---|---|---|---|---|---|---|---|---|---|---|---|
| M731 | 0.5 | 0.8 | 20 | 0 | 0 | 3 | 0 | 0 | 0 | 0 | 0 |
| M732 | 0.5 | 0.8 | 20 | 0 | 0 | 4 | 0 | 0 | 0 | 0 | 0 |
| M733 | 0.5 | 0.9 | 15 | 0 | 0 | 2 | 0 | 0 | 0 | 0 | 0 |
| M734 | 0.5 | 0.9 | 15 | 0 | 0 | 3 | 0 | 0 | 0 | 0 | 0 |
| M735 | 0.5 | 0.9 | 15 | 0 | 0 | 4 | 0 | 0 | 0 | 0 | 0 |
| M736 | 0.5 | 0.9 | 15 | 0 | 0 | 5 | 0 | 0 | 0 | 0 | 0 |
| M737 | 0.5 | 0.9 | 15 | 0 | 0 | 6 | 0 | 0 | 0 | 0 | 0 |
| M738 | 0.9 | 0.8 | 15 | 0 | 0 | 0 | 0 | 0 | 4 | 0 | 0 |
| M739 | 0.9 | 0.8 | 15 | 0 | 0 | 0 | 0 | 0 | 5 | 0 | 0 |
| M740 | 0.9 | 0.8 | 15 | 0 | 0 | 0 | 0 | 0 | 6 | 0 | 0 |
| M741 | 0.5 | 0.9 | 20 | 0 | 0 | 3 | 0 | 0 | 0 | 0 | 0 |
| M742 | 0.5 | 0.9 | 20 | 0 | 0 | 4 | 0 | 0 | 0 | 0 | 0 |
| M743 | 0.5 | 0.9 | 20 | 0 | 0 | 5 | 0 | 0 | 0 | 0 | 0 |
| M744 | 0.5 | 1 | 15 | 0 | 0 | 2 | 0 | 0 | 0 | 0 | 0 |
| M745 | 0.5 | 1 | 15 | 0 | 0 | 3 | 0 | 0 | 0 | 0 | 0 |
| M746 | 0.5 | 1 | 15 | 0 | 0 | 4 | 0 | 0 | 0 | 0 | 0 |
| M747 | 0.5 | 1 | 15 | 0 | 0 | 5 | 0 | 0 | 0 | 0 | 0 |
| M748 | 0.9 | 0.8 | 20 | 0 | 0 | 0 | 0 | 0 | 7 | 0 | 0 |
| M749 | 0.5 | 1 | 15 | 0 | 0 | 6 | 0 | 0 | 0 | 0 | 0 |
| M750 | 0.5 | 1 | 15 | 0 | 0 | 7 | 0 | 0 | 0 | 0 | 0 |
| M751 | 0.5 | 1 | 20 | 0 | 0 | 4 | 0 | 0 | 0 | 0 | 0 |
| M752 | 0.9 | 0.9 | 15 | 0 | 0 | 0 | 0 | 0 | 5 | 0 | 0 |
| M753 | 0.5 | 1 | 20 | 0 | 0 | 5 | 0 | 0 | 0 | 0 | 0 |
| M754 | 0.9 | 0.9 | 15 | 0 | 0 | 0 | 0 | 0 | 6 | 0 | 0 |
| M755 | 0.5 | 1 | 20 | 0 | 0 | 6 | 0 | 0 | 0 | 0 | 0 |
| M756 | 0.5 | 1.1 | 15 | 0 | 0 | 2 | 0 | 0 | 0 | 0 | 0 |
| M757 | 0.5 | 1.1 | 15 | 0 | 0 | 3 | 0 | 0 | 0 | 0 | 0 |
| M758 | 0.5 | 1.1 | 15 | 0 | 0 | 4 | 0 | 0 | 0 | 0 | 0 |
| M759 | 0.5 | 1.1 | 15 | 0 | 0 | 5 | 0 | 0 | 0 | 0 | 0 |
| M760 | 0.5 | 1.1 | 15 | 0 | 0 | 6 | 0 | 0 | 0 | 0 | 0 |
| M761 | 0.5 | 1.1 | 15 | 0 | 0 | 7 | 0 | 0 | 0 | 0 | 0 |
| M762 | 0.9 | 0.9 | 20 | 0 | 0 | 0 | 0 | 0 | 8 | 0 | 0 |
| M763 | 0.9 | 0.9 | 20 | 0 | 0 | 0 | 0 | 0 | 9 | 0 | 0 |
| M764 | 0.9 | 0.9 | 20 | 0 | 0 | 0 | 0 | 0 | 10 | 0 | 0 |
| M765 | 0.5 | 1.1 | 20 | 0 | 0 | 5 | 0 | 0 | 0 | 0 | 0 |
| M766 | 0.5 | 1.1 | 20 | 0 | 0 | 6 | 0 | 0 | 0 | 0 | 0 |
| M767 | 0.5 | 1.1 | 20 | 0 | 0 | 7 | 0 | 0 | 0 | 0 | 0 |
| M768 | 0.9 | 1 | 15 | 0 | 0 | 0 | 0 | 0 | 5 | 0 | 0 |
| M769 | 0.5 | 1.2 | 15 | 0 | 0 | 3 | 0 | 0 | 0 | 0 | 0 |
| M770 | 0.5 | 1.2 | 15 | 0 | 0 | 4 | 0 | 0 | 0 | 0 | 0 |
| M771 | 0.5 | 1.2 | 15 | 0 | 0 | 5 | 0 | 0 | 0 | 0 | 0 |
| M772 | 0.9 | 1 | 15 | 0 | 0 | 0 | 0 | 0 | 9 | 0 | 0 |
| M773 | 0.9 | 1 | 15 | 0 | 0 | 0 | 0 | 0 | 10 | 0 | 0 |
| M774 | 0.5 | 1.2 | 15 | 0 | 0 | 6 | 0 | 0 | 0 | 0 | 0 |
| M775 | 0.5 | 1.2 | 15 | 0 | 0 | 7 | 0 | 0 | 0 | 0 | 0 |
| M776 | 0.9 | 1 | 20 | 0 | 0 | 0 | 0 | 0 | 8 | 0 | 0 |
| M777 | 0.5 | 1.2 | 20 | 0 | 0 | 6 | 0 | 0 | 0 | 0 | 0 |
| M778 | 0.9 | 1 | 20 | 0 | 0 | 0 | 0 | 0 | 9 | 0 | 0 |
| M779 | 0.5 | 1.2 | 20 | 0 | 0 | 7 | 0 | 0 | 0 | 0 | 0 |
| M780 | 0.9 | 1 | 20 | 0 | 0 | 0 | 0 | 0 | 10 | 0 | 0 |
| M781 | 0.5 | 1.2 | 20 | 0 | 0 | 8 | 0 | 0 | 0 | 0 | 0 |
| M782 | 0.5 | 1.3 | 15 | 0 | 0 | 4 | 0 | 0 | 0 | 0 | 0 |
| M783 | 0.5 | 1.3 | 15 | 0 | 0 | 5 | 0 | 0 | 0 | 0 | 0 |
| M784 | 0.9 | 1.1 | 15 | 0 | 0 | 0 | 0 | 0 | 6 | 0 | 0 |
| M785 | 0.5 | 1.3 | 15 | 0 | 0 | 6 | 0 | 0 | 0 | 0 | 0 |
| M786 | 0.9 | 1.1 | 15 | 0 | 0 | 0 | 0 | 0 | 7 | 0 | 0 |
| M787 | 0.5 | 1.3 | 15 | 0 | 0 | 7 | 0 | 0 | 0 | 0 | 0 |
| M788 | 0.9 | 1.1 | 15 | 0 | 0 | 0 | 0 | 0 | 8 | 0 | 0 |
| M789 | 0.5 | 1.3 | 15 | 0 | 0 | 8 | 0 | 0 | 0 | 0 | 0 |
| M790 | 0.9 | 1.1 | 15 | 0 | 0 | 0 | 0 | 0 | 9 | 0 | 0 |
| M791 | 0.9 | 1.1 | 15 | 0 | 0 | 0 | 0 | 0 | 10 | 0 | 0 |
| M792 | 0.5 | 1.3 | 20 | 0 | 0 | 7 | 0 | 0 | 0 | 0 | 0 |
| M793 | 0.5 | 1.3 | 20 | 0 | 0 | 8 | 0 | 0 | 0 | 0 | 0 |
| M794 | 0.9 | 1.1 | 20 | 0 | 0 | 0 | 0 | 0 | 9 | 0 | 0 |
| M795 | 0.9 | 1.1 | 20 | 0 | 0 | 0 | 0 | 0 | 10 | 0 | 0 |
| M796 | 0.5 | 1.4 | 15 | 0 | 0 | 5 | 0 | 0 | 0 | 0 | 0 |
| M797 | 0.5 | 1.4 | 15 | 0 | 0 | 6 | 0 | 0 | 0 | 0 | 0 |
| M798 | 0.5 | 1.4 | 15 | 0 | 0 | 7 | 0 | 0 | 0 | 0 | 0 |
| M799 | 0.5 | 1.4 | 15 | 0 | 0 | 8 | 0 | 0 | 0 | 0 | 0 |
| M800 | 0.9 | 1.2 | 15 | 0 | 0 | 0 | 0 | 0 | 6 | 0 | 0 |
| M801 | 0.9 | 1.2 | 15 | 0 | 0 | 0 | 0 | 0 | 7 | 0 | 0 |
| M802 | 0.9 | 1.2 | 15 | 0 | 0 | 0 | 0 | 0 | 8 | 0 | 0 |
| M803 | 0.9 | 1.2 | 15 | 0 | 0 | 0 | 0 | 0 | 9 | 0 | 0 |
| M804 | 0.9 | 1.2 | 15 | 0 | 0 | 0 | 0 | 0 | 10 | 0 | 0 |
| M805 | 0.5 | 1.4 | 20 | 0 | 0 | 7 | 0 | 0 | 0 | 0 | 0 |

TABLE 3-continued

Alloy chemistries in weight percent, balance Fe, for selected alloys evaluated using thermodynamic models which meet thermodynamic criteria

| Alloy | B | C | Cr | Mn | Mo | Nb | Si | Ti | V | W | Zr |
|---|---|---|---|---|---|---|---|---|---|---|---|
| M806 | 0.5 | 1.4 | 20 | 0 | 0 | 8 | 0 | 0 | 0 | 0 | 0 |
| M807 | 0.5 | 1.5 | 15 | 0 | 0 | 5 | 0 | 0 | 0 | 0 | 0 |
| M808 | 0.5 | 1.5 | 15 | 0 | 0 | 6 | 0 | 0 | 0 | 0 | 0 |
| M809 | 0.9 | 1.2 | 20 | 0 | 0 | 0 | 0 | 0 | 9 | 0 | 0 |
| M810 | 0.5 | 1.5 | 15 | 0 | 0 | 7 | 0 | 0 | 0 | 0 | 0 |
| M811 | 0.9 | 1.2 | 20 | 0 | 0 | 0 | 0 | 0 | 10 | 0 | 0 |
| M812 | 0.5 | 1.5 | 15 | 0 | 0 | 8 | 0 | 0 | 0 | 0 | 0 |
| M813 | 0.9 | 1.3 | 15 | 0 | 0 | 0 | 0 | 0 | 6 | 0 | 0 |
| M814 | 0.9 | 1.3 | 15 | 0 | 0 | 0 | 0 | 0 | 7 | 0 | 0 |
| M815 | 0.9 | 1.3 | 15 | 0 | 0 | 0 | 0 | 0 | 8 | 0 | 0 |
| M816 | 0.5 | 1.5 | 20 | 0 | 0 | 8 | 0 | 0 | 0 | 0 | 0 |
| M817 | 0.9 | 1.3 | 15 | 0 | 0 | 0 | 0 | 0 | 9 | 0 | 0 |
| M818 | 0.9 | 1.3 | 15 | 0 | 0 | 0 | 0 | 0 | 10 | 0 | 0 |
| M819 | 0.5 | 1.6 | 15 | 0 | 0 | 6 | 0 | 0 | 0 | 0 | 0 |
| M820 | 0.5 | 1.6 | 15 | 0 | 0 | 7 | 0 | 0 | 0 | 0 | 0 |
| M821 | 0.5 | 1.6 | 15 | 0 | 0 | 8 | 0 | 0 | 0 | 0 | 0 |
| M822 | 0.9 | 1.3 | 20 | 0 | 0 | 0 | 0 | 0 | 10 | 0 | 0 |
| M823 | 0.9 | 1.4 | 15 | 0 | 0 | 0 | 0 | 0 | 7 | 0 | 0 |
| M824 | 0.9 | 1.4 | 15 | 0 | 0 | 0 | 0 | 0 | 8 | 0 | 0 |
| M825 | 0.9 | 1.4 | 15 | 0 | 0 | 0 | 0 | 0 | 9 | 0 | 0 |
| M826 | 0.9 | 1.4 | 15 | 0 | 0 | 0 | 0 | 0 | 10 | 0 | 0 |
| M827 | 0.5 | 1.7 | 15 | 0 | 0 | 7 | 0 | 0 | 0 | 0 | 0 |
| M828 | 0.5 | 1.7 | 15 | 0 | 0 | 8 | 0 | 0 | 0 | 0 | 0 |
| M829 | 0.5 | 1.8 | 15 | 0 | 0 | 8 | 0 | 0 | 0 | 0 | 0 |
| M830 | 0.6 | 0.8 | 15 | 0 | 0 | 2 | 0 | 0 | 0 | 0 | 0 |
| M831 | 0.6 | 0.8 | 15 | 0 | 0 | 3 | 0 | 0 | 0 | 0 | 0 |
| M832 | 0.6 | 0.8 | 20 | 0 | 0 | 3 | 0 | 0 | 0 | 0 | 0 |
| M833 | 0.6 | 0.8 | 20 | 0 | 0 | 4 | 0 | 0 | 0 | 0 | 0 |
| M834 | 0.6 | 0.9 | 15 | 0 | 0 | 2 | 0 | 0 | 0 | 0 | 0 |
| M835 | 0.6 | 0.9 | 15 | 0 | 0 | 3 | 0 | 0 | 0 | 0 | 0 |
| M836 | 0.6 | 0.9 | 15 | 0 | 0 | 4 | 0 | 0 | 0 | 0 | 0 |
| M837 | 0.6 | 0.9 | 20 | 0 | 0 | 4 | 0 | 0 | 0 | 0 | 0 |
| M838 | 0.6 | 0.9 | 20 | 0 | 0 | 5 | 0 | 0 | 0 | 0 | 0 |
| M839 | 0.6 | 1 | 15 | 0 | 0 | 2 | 0 | 0 | 0 | 0 | 0 |
| M840 | 0.6 | 1 | 15 | 0 | 0 | 3 | 0 | 0 | 0 | 0 | 0 |
| M841 | 0.6 | 1 | 15 | 0 | 0 | 4 | 0 | 0 | 0 | 0 | 0 |
| M842 | 0.6 | 1 | 15 | 0 | 0 | 5 | 0 | 0 | 0 | 0 | 0 |
| M843 | 0.6 | 1 | 20 | 0 | 0 | 5 | 0 | 0 | 0 | 0 | 0 |
| M844 | 0.6 | 1.1 | 15 | 0 | 0 | 3 | 0 | 0 | 0 | 0 | 0 |
| M845 | 0.6 | 1.1 | 15 | 0 | 0 | 4 | 0 | 0 | 0 | 0 | 0 |
| M846 | 0.6 | 1.1 | 15 | 0 | 0 | 5 | 0 | 0 | 0 | 0 | 0 |
| M847 | 0.6 | 1.1 | 15 | 0 | 0 | 6 | 0 | 0 | 0 | 0 | 0 |
| M848 | 0.6 | 1.1 | 20 | 0 | 0 | 5 | 0 | 0 | 0 | 0 | 0 |
| M849 | 0.6 | 1.1 | 20 | 0 | 0 | 6 | 0 | 0 | 0 | 0 | 0 |
| M850 | 0.6 | 1.2 | 15 | 0 | 0 | 4 | 0 | 0 | 0 | 0 | 0 |
| M851 | 0.6 | 1.2 | 15 | 0 | 0 | 5 | 0 | 0 | 0 | 0 | 0 |
| M852 | 0.6 | 1.2 | 15 | 0 | 0 | 6 | 0 | 0 | 0 | 0 | 0 |
| M853 | 0.6 | 1.2 | 20 | 0 | 0 | 6 | 0 | 0 | 0 | 0 | 0 |
| M854 | 0.6 | 1.2 | 20 | 0 | 0 | 7 | 0 | 0 | 0 | 0 | 0 |
| M855 | 0.6 | 1.3 | 15 | 0 | 0 | 5 | 0 | 0 | 0 | 0 | 0 |
| M856 | 0.6 | 1.3 | 15 | 0 | 0 | 6 | 0 | 0 | 0 | 0 | 0 |
| M857 | 0.6 | 1.3 | 15 | 0 | 0 | 7 | 0 | 0 | 0 | 0 | 0 |
| M858 | 0.6 | 1.3 | 20 | 0 | 0 | 7 | 0 | 0 | 0 | 0 | 0 |
| M859 | 0.6 | 1.3 | 20 | 0 | 0 | 8 | 0 | 0 | 0 | 0 | 0 |
| M860 | 0.6 | 1.4 | 15 | 0 | 0 | 6 | 0 | 0 | 0 | 0 | 0 |
| M861 | 0.6 | 1.4 | 15 | 0 | 0 | 7 | 0 | 0 | 0 | 0 | 0 |
| M862 | 0.6 | 1.4 | 15 | 0 | 0 | 8 | 0 | 0 | 0 | 0 | 0 |
| M863 | 0.6 | 1.4 | 20 | 0 | 0 | 8 | 0 | 0 | 0 | 0 | 0 |
| M864 | 0.6 | 1.5 | 15 | 0 | 0 | 6 | 0 | 0 | 0 | 0 | 0 |
| M865 | 0.6 | 1.5 | 15 | 0 | 0 | 7 | 0 | 0 | 0 | 0 | 0 |
| M866 | 0.6 | 1.5 | 15 | 0 | 0 | 8 | 0 | 0 | 0 | 0 | 0 |
| M867 | 0.6 | 1.6 | 15 | 0 | 0 | 7 | 0 | 0 | 0 | 0 | 0 |
| M868 | 0.6 | 1.6 | 15 | 0 | 0 | 8 | 0 | 0 | 0 | 0 | 0 |
| M869 | 0.6 | 1.7 | 15 | 0 | 0 | 8 | 0 | 0 | 0 | 0 | 0 |
| M870 | 0.7 | 0.8 | 15 | 0 | 0 | 2 | 0 | 0 | 0 | 0 | 0 |
| M871 | 0.7 | 0.8 | 20 | 0 | 0 | 3 | 0 | 0 | 0 | 0 | 0 |
| M872 | 0.7 | 0.9 | 15 | 0 | 0 | 2 | 0 | 0 | 0 | 0 | 0 |
| M873 | 0.7 | 0.9 | 15 | 0 | 0 | 3 | 0 | 0 | 0 | 0 | 0 |
| M874 | 0.7 | 0.9 | 20 | 0 | 0 | 4 | 0 | 0 | 0 | 0 | 0 |
| M875 | 0.7 | 1 | 15 | 0 | 0 | 3 | 0 | 0 | 0 | 0 | 0 |
| M876 | 0.7 | 1 | 20 | 0 | 0 | 5 | 0 | 0 | 0 | 0 | 0 |
| M877 | 0.7 | 1.1 | 15 | 0 | 0 | 4 | 0 | 0 | 0 | 0 | 0 |
| M878 | 0.7 | 1.1 | 20 | 0 | 0 | 6 | 0 | 0 | 0 | 0 | 0 |
| M879 | 0.7 | 1.2 | 15 | 0 | 0 | 5 | 0 | 0 | 0 | 0 | 0 |
| M880 | 0.7 | 1.2 | 20 | 0 | 0 | 7 | 0 | 0 | 0 | 0 | 0 |

TABLE 3-continued

Alloy chemistries in weight percent, balance Fe, for selected alloys evaluated using thermodynamic models which meet thermodynamic criteria

| Alloy | B | C | Cr | Mn | Mo | Nb | Si | Ti | V | W | Zr |
|---|---|---|---|---|---|---|---|---|---|---|---|
| M881 | 0.7 | 1.3 | 20 | 0 | 0 | 8 | 0 | 0 | 0 | 0 | 0 |
| M882 | 0.7 | 1.4 | 15 | 0 | 0 | 6 | 0 | 0 | 0 | 0 | 0 |
| M883 | 0.7 | 1.5 | 15 | 0 | 0 | 7 | 0 | 0 | 0 | 0 | 0 |
| M884 | 0.7 | 1.6 | 15 | 0 | 0 | 8 | 0 | 0 | 0 | 0 | 0 |
| M885 | 0.9 | 1.4 | 20 | 0 | 0 | 0 | 0 | 0 | 10 | 0 | 0 |
| M886 | 0.9 | 1.5 | 15 | 0 | 0 | 0 | 0 | 0 | 7 | 0 | 0 |
| M887 | 0.9 | 1.5 | 15 | 0 | 0 | 0 | 0 | 0 | 8 | 0 | 0 |
| M888 | 0.9 | 1.5 | 15 | 0 | 0 | 0 | 0 | 0 | 9 | 0 | 0 |
| M889 | 0.9 | 1.6 | 15 | 0 | 0 | 0 | 0 | 0 | 8 | 0 | 0 |
| M890 | 0.9 | 1.6 | 15 | 0 | 0 | 0 | 0 | 0 | 9 | 0 | 0 |
| M891 | 0.9 | 1.7 | 15 | 0 | 0 | 0 | 0 | 0 | 8 | 0 | 0 |
| M892 | 0.9 | 1.7 | 15 | 0 | 0 | 0 | 0 | 0 | 9 | 0 | 0 |
| M893 | 0.9 | 1.7 | 15 | 0 | 0 | 0 | 0 | 0 | 10 | 0 | 0 |
| M894 | 0.9 | 1.8 | 15 | 0 | 0 | 0 | 0 | 0 | 9 | 0 | 0 |
| M895 | 0.9 | 1.8 | 15 | 0 | 0 | 0 | 0 | 0 | 10 | 0 | 0 |
| M896 | 0.9 | 1.9 | 15 | 0 | 0 | 0 | 0 | 0 | 9 | 0 | 0 |
| M897 | 0.9 | 1.9 | 15 | 0 | 0 | 0 | 0 | 0 | 10 | 0 | 0 |
| M898 | 0.9 | 2 | 15 | 0 | 0 | 0 | 0 | 0 | 10 | 0 | 0 |
| M899 | 0.4 | 0.8 | 12 | 0 | 0 | 0 | 0 | 0 | 0 | 0 | 2 |
| M900 | 0.4 | 0.9 | 12 | 0 | 0 | 0 | 0 | 0 | 0 | 0 | 3 |
| M901 | 0.4 | 0.9 | 14 | 0 | 0 | 0 | 0 | 0 | 0 | 0 | 3 |
| M902 | 0.4 | 1 | 12 | 0 | 0 | 0 | 0 | 0 | 0 | 0 | 4 |
| M903 | 0.4 | 1 | 14 | 0 | 0 | 0 | 0 | 0 | 0 | 0 | 4 |
| M904 | 0.4 | 1.1 | 12 | 0 | 0 | 0 | 0 | 0 | 0 | 0 | 5 |
| M905 | 0.4 | 1.1 | 14 | 0 | 0 | 0 | 0 | 0 | 0 | 0 | 5 |
| M906 | 0.4 | 1.2 | 12 | 0 | 0 | 0 | 0 | 0 | 0 | 0 | 5 |
| M907 | 0.4 | 1.2 | 12 | 0 | 0 | 0 | 0 | 0 | 0 | 0 | 6 |
| M908 | 0.4 | 1.2 | 14 | 0 | 0 | 0 | 0 | 0 | 0 | 0 | 6 |
| M909 | 0.4 | 1.3 | 12 | 0 | 0 | 0 | 0 | 0 | 0 | 0 | 6 |
| M910 | 0.4 | 1.4 | 12 | 0 | 0 | 0 | 0 | 0 | 0 | 0 | 7 |
| M911 | 0.4 | 1.4 | 14 | 0 | 0 | 0 | 0 | 0 | 0 | 0 | 7 |
| M912 | 0.4 | 1.5 | 12 | 0 | 0 | 0 | 0 | 0 | 0 | 0 | 8 |
| M913 | 0.4 | 1.5 | 14 | 0 | 0 | 0 | 0 | 0 | 0 | 0 | 8 |
| M914 | 0.4 | 1.7 | 16 | 0 | 0 | 0 | 0 | 0 | 0 | 0 | 6 |
| M915 | 0.4 | 1.8 | 16 | 0 | 0 | 0 | 0 | 0 | 0 | 0 | 7 |
| M916 | 0.4 | 1.9 | 16 | 0 | 0 | 0 | 0 | 0 | 0 | 0 | 8 |
| M917 | 0.4 | 2 | 16 | 0 | 0 | 0 | 0 | 0 | 0 | 0 | 8 |
| M918 | 0.5 | 0.8 | 12 | 0 | 0 | 0 | 0 | 0 | 0 | 0 | 2 |
| M919 | 0.5 | 0.8 | 14 | 0 | 0 | 0 | 0 | 0 | 0 | 0 | 2 |
| M920 | 0.5 | 0.9 | 12 | 0 | 0 | 0 | 0 | 0 | 0 | 0 | 3 |
| M921 | 0.5 | 0.9 | 14 | 0 | 0 | 0 | 0 | 0 | 0 | 0 | 3 |
| M922 | 0.5 | 1 | 12 | 0 | 0 | 0 | 0 | 0 | 0 | 0 | 3 |
| M923 | 0.5 | 1 | 12 | 0 | 0 | 0 | 0 | 0 | 0 | 0 | 4 |
| M924 | 0.5 | 1 | 14 | 0 | 0 | 0 | 0 | 0 | 0 | 0 | 4 |
| M925 | 0.5 | 1.1 | 12 | 0 | 0 | 0 | 0 | 0 | 0 | 0 | 4 |
| M926 | 0.5 | 1.1 | 12 | 0 | 0 | 0 | 0 | 0 | 0 | 0 | 5 |
| M927 | 0.5 | 1.1 | 14 | 0 | 0 | 0 | 0 | 0 | 0 | 0 | 4 |
| M928 | 0.5 | 1.1 | 14 | 0 | 0 | 0 | 0 | 0 | 0 | 0 | 5 |
| M929 | 0.5 | 1.2 | 12 | 0 | 0 | 0 | 0 | 0 | 0 | 0 | 5 |
| M930 | 0.5 | 1.2 | 12 | 0 | 0 | 0 | 0 | 0 | 0 | 0 | 6 |
| M931 | 0.5 | 1.2 | 14 | 0 | 0 | 0 | 0 | 0 | 0 | 0 | 5 |
| M932 | 0.5 | 1.2 | 14 | 0 | 0 | 0 | 0 | 0 | 0 | 0 | 6 |
| M933 | 0.5 | 1.2 | 16 | 0 | 0 | 0 | 0 | 0 | 0 | 0 | 6 |
| M934 | 0.5 | 1.3 | 12 | 0 | 0 | 0 | 0 | 0 | 0 | 0 | 6 |
| M935 | 0.5 | 1.3 | 12 | 0 | 0 | 0 | 0 | 0 | 0 | 0 | 7 |
| M936 | 0.5 | 1.3 | 14 | 0 | 0 | 0 | 0 | 0 | 0 | 0 | 6 |
| M937 | 0.5 | 1.3 | 16 | 0 | 0 | 0 | 0 | 0 | 0 | 0 | 4 |
| M938 | 0.5 | 1.4 | 12 | 0 | 0 | 0 | 0 | 0 | 0 | 0 | 7 |
| M939 | 0.5 | 1.4 | 14 | 0 | 0 | 0 | 0 | 0 | 0 | 0 | 7 |
| M940 | 0.5 | 1.5 | 12 | 0 | 0 | 0 | 0 | 0 | 0 | 0 | 7 |
| M941 | 0.5 | 1.5 | 12 | 0 | 0 | 0 | 0 | 0 | 0 | 0 | 8 |
| M942 | 0.5 | 1.5 | 14 | 0 | 0 | 0 | 0 | 0 | 0 | 0 | 8 |
| M943 | 0.5 | 1.5 | 16 | 0 | 0 | 0 | 0 | 0 | 0 | 0 | 5 |
| M944 | 0.5 | 1.6 | 12 | 0 | 0 | 0 | 0 | 0 | 0 | 0 | 8 |
| M945 | 0.5 | 1.6 | 14 | 0 | 0 | 0 | 0 | 0 | 0 | 0 | 8 |
| M946 | 0.5 | 1.6 | 16 | 0 | 0 | 0 | 0 | 0 | 0 | 0 | 6 |
| M947 | 0.5 | 1.7 | 14 | 0 | 0 | 0 | 0 | 0 | 0 | 0 | 6 |
| M948 | 0.5 | 1.7 | 16 | 0 | 0 | 0 | 0 | 0 | 0 | 0 | 7 |
| M949 | 0.5 | 1.8 | 14 | 0 | 0 | 0 | 0 | 0 | 0 | 0 | 7 |
| M950 | 0.5 | 1.8 | 16 | 0 | 0 | 0 | 0 | 0 | 0 | 0 | 8 |
| M951 | 0.5 | 1.9 | 14 | 0 | 0 | 0 | 0 | 0 | 0 | 0 | 8 |
| M952 | 0.5 | 1.9 | 16 | 0 | 0 | 0 | 0 | 0 | 0 | 0 | 8 |
| M953 | 0.6 | 0.8 | 12 | 0 | 0 | 0 | 0 | 0 | 0 | 0 | 2 |
| M954 | 0.6 | 0.8 | 12 | 0 | 0 | 0 | 0 | 0 | 0 | 0 | 3 |
| M955 | 0.6 | 0.8 | 14 | 0 | 0 | 0 | 0 | 0 | 0 | 0 | 2 |

TABLE 3-continued

Alloy chemistries in weight percent, balance Fe, for selected alloys evaluated using thermodynamic models which meet thermodynamic criteria

| Alloy | B | C | Cr | Mn | Mo | Nb | Si | Ti | V | W | Zr |
|---|---|---|---|---|---|---|---|---|---|---|---|
| M956 | 0.6 | 0.8 | 16 | 0 | 0 | 0 | 0 | 0 | 0 | 0 | 2 |
| M957 | 0.6 | 0.9 | 12 | 0 | 0 | 0 | 0 | 0 | 0 | 0 | 2 |
| M958 | 0.6 | 0.9 | 12 | 0 | 0 | 0 | 0 | 0 | 0 | 0 | 3 |
| M959 | 0.6 | 0.9 | 14 | 0 | 0 | 0 | 0 | 0 | 0 | 0 | 2 |
| M960 | 0.6 | 0.9 | 14 | 0 | 0 | 0 | 0 | 0 | 0 | 0 | 3 |
| M961 | 0.6 | 0.9 | 16 | 0 | 0 | 0 | 0 | 0 | 0 | 0 | 3 |
| M962 | 0.6 | 1 | 12 | 0 | 0 | 0 | 0 | 0 | 0 | 0 | 3 |
| M963 | 0.6 | 1 | 12 | 0 | 0 | 0 | 0 | 0 | 0 | 0 | 4 |
| M964 | 0.6 | 1 | 14 | 0 | 0 | 0 | 0 | 0 | 0 | 0 | 3 |
| M965 | 0.6 | 1 | 14 | 0 | 0 | 0 | 0 | 0 | 0 | 0 | 4 |
| M966 | 0.6 | 1 | 16 | 0 | 0 | 0 | 0 | 0 | 0 | 0 | 2 |
| M967 | 0.6 | 1 | 16 | 0 | 0 | 0 | 0 | 0 | 0 | 0 | 4 |
| M968 | 0.6 | 1.1 | 12 | 0 | 0 | 0 | 0 | 0 | 0 | 0 | 4 |
| M969 | 0.6 | 1.1 | 12 | 0 | 0 | 0 | 0 | 0 | 0 | 0 | 5 |
| M970 | 0.6 | 1.1 | 14 | 0 | 0 | 0 | 0 | 0 | 0 | 0 | 4 |
| M971 | 0.6 | 1.1 | 14 | 0 | 0 | 0 | 0 | 0 | 0 | 0 | 5 |
| M972 | 0.6 | 1.1 | 16 | 0 | 0 | 0 | 0 | 0 | 0 | 0 | 3 |
| M973 | 0.6 | 1.1 | 16 | 0 | 0 | 0 | 0 | 0 | 0 | 0 | 4 |
| M974 | 0.6 | 1.1 | 16 | 0 | 0 | 0 | 0 | 0 | 0 | 0 | 5 |
| M975 | 0.6 | 1.2 | 12 | 0 | 0 | 0 | 0 | 0 | 0 | 0 | 5 |
| M976 | 0.6 | 1.2 | 12 | 0 | 0 | 0 | 0 | 0 | 0 | 0 | 6 |
| M977 | 0.6 | 1.2 | 14 | 0 | 0 | 0 | 0 | 0 | 0 | 0 | 3 |
| M978 | 0.6 | 1.2 | 14 | 0 | 0 | 0 | 0 | 0 | 0 | 0 | 5 |
| M979 | 0.6 | 1.2 | 14 | 0 | 0 | 0 | 0 | 0 | 0 | 0 | 6 |
| M980 | 0.6 | 1.2 | 16 | 0 | 0 | 0 | 0 | 0 | 0 | 0 | 4 |
| M981 | 0.6 | 1.2 | 16 | 0 | 0 | 0 | 0 | 0 | 0 | 0 | 5 |
| M982 | 0.6 | 1.2 | 16 | 0 | 0 | 0 | 0 | 0 | 0 | 0 | 6 |
| M983 | 0.6 | 1.3 | 12 | 0 | 0 | 0 | 0 | 0 | 0 | 0 | 5 |
| M984 | 0.6 | 1.3 | 12 | 0 | 0 | 0 | 0 | 0 | 0 | 0 | 6 |
| M985 | 0.6 | 1.3 | 12 | 0 | 0 | 0 | 0 | 0 | 0 | 0 | 7 |
| M986 | 0.6 | 1.3 | 14 | 0 | 0 | 0 | 0 | 0 | 0 | 0 | 4 |
| M987 | 0.6 | 1.3 | 14 | 0 | 0 | 0 | 0 | 0 | 0 | 0 | 5 |
| M988 | 0.6 | 1.3 | 14 | 0 | 0 | 0 | 0 | 0 | 0 | 0 | 6 |
| M989 | 0.6 | 1.3 | 14 | 0 | 0 | 0 | 0 | 0 | 0 | 0 | 7 |
| M990 | 0.6 | 1.3 | 16 | 0 | 0 | 0 | 0 | 0 | 0 | 0 | 5 |
| M991 | 0.6 | 1.3 | 16 | 0 | 0 | 0 | 0 | 0 | 0 | 0 | 6 |
| M992 | 0.6 | 1.3 | 16 | 0 | 0 | 0 | 0 | 0 | 0 | 0 | 7 |
| M993 | 0.6 | 1.4 | 12 | 0 | 0 | 0 | 0 | 0 | 0 | 0 | 6 |
| M994 | 0.6 | 1.4 | 12 | 0 | 0 | 0 | 0 | 0 | 0 | 0 | 7 |
| M995 | 0.6 | 1.4 | 14 | 0 | 0 | 0 | 0 | 0 | 0 | 0 | 5 |
| M996 | 0.6 | 1.4 | 14 | 0 | 0 | 0 | 0 | 0 | 0 | 0 | 6 |
| M997 | 0.6 | 1.4 | 14 | 0 | 0 | 0 | 0 | 0 | 0 | 0 | 7 |
| M998 | 0.6 | 1.4 | 16 | 0 | 0 | 0 | 0 | 0 | 0 | 0 | 5 |
| M999 | 0.6 | 1.4 | 16 | 0 | 0 | 0 | 0 | 0 | 0 | 0 | 6 |
| M1000 | 0.6 | 1.4 | 16 | 0 | 0 | 0 | 0 | 0 | 0 | 0 | 7 |
| M1001 | 0.6 | 1.5 | 12 | 0 | 0 | 0 | 0 | 0 | 0 | 0 | 7 |
| M1002 | 0.6 | 1.5 | 12 | 0 | 0 | 0 | 0 | 0 | 0 | 0 | 8 |
| M1003 | 0.6 | 1.5 | 14 | 0 | 0 | 0 | 0 | 0 | 0 | 0 | 6 |
| M1004 | 0.6 | 1.5 | 14 | 0 | 0 | 0 | 0 | 0 | 0 | 0 | 7 |
| M1005 | 0.6 | 1.5 | 14 | 0 | 0 | 0 | 0 | 0 | 0 | 0 | 8 |
| M1006 | 0.6 | 1.5 | 16 | 0 | 0 | 0 | 0 | 0 | 0 | 0 | 6 |
| M1007 | 0.6 | 1.5 | 16 | 0 | 0 | 0 | 0 | 0 | 0 | 0 | 7 |
| M1008 | 0.6 | 1.5 | 16 | 0 | 0 | 0 | 0 | 0 | 0 | 0 | 8 |
| M1009 | 0.6 | 1.6 | 12 | 0 | 0 | 0 | 0 | 0 | 0 | 0 | 8 |
| M1010 | 0.6 | 1.6 | 14 | 0 | 0 | 0 | 0 | 0 | 0 | 0 | 6 |
| M1011 | 0.6 | 1.6 | 14 | 0 | 0 | 0 | 0 | 0 | 0 | 0 | 7 |
| M1012 | 0.6 | 1.6 | 14 | 0 | 0 | 0 | 0 | 0 | 0 | 0 | 8 |
| M1013 | 0.6 | 1.6 | 16 | 0 | 0 | 0 | 0 | 0 | 0 | 0 | 7 |
| M1014 | 0.6 | 1.6 | 16 | 0 | 0 | 0 | 0 | 0 | 0 | 0 | 8 |
| M1015 | 0.6 | 1.7 | 12 | 0 | 0 | 0 | 0 | 0 | 0 | 0 | 6 |
| M1016 | 0.6 | 1.7 | 12 | 0 | 0 | 0 | 0 | 0 | 0 | 0 | 8 |
| M1017 | 0.6 | 1.7 | 14 | 0 | 0 | 0 | 0 | 0 | 0 | 0 | 7 |
| M1018 | 0.6 | 1.7 | 14 | 0 | 0 | 0 | 0 | 0 | 0 | 0 | 8 |
| M1019 | 0.6 | 1.7 | 16 | 0 | 0 | 0 | 0 | 0 | 0 | 0 | 8 |
| M1020 | 0.6 | 1.8 | 12 | 0 | 0 | 0 | 0 | 0 | 0 | 0 | 7 |
| M1021 | 0.6 | 1.8 | 14 | 0 | 0 | 0 | 0 | 0 | 0 | 0 | 8 |
| M1022 | 0.6 | 1.9 | 12 | 0 | 0 | 0 | 0 | 0 | 0 | 0 | 8 |
| M1023 | 0.7 | 0.8 | 12 | 0 | 0 | 0 | 0 | 0 | 0 | 0 | 2 |
| M1024 | 0.7 | 0.8 | 12 | 0 | 0 | 0 | 0 | 0 | 0 | 0 | 3 |
| M1025 | 0.7 | 0.8 | 14 | 0 | 0 | 0 | 0 | 0 | 0 | 0 | 2 |
| M1026 | 0.7 | 0.8 | 14 | 0 | 0 | 0 | 0 | 0 | 0 | 0 | 3 |
| M1027 | 0.7 | 0.8 | 16 | 0 | 0 | 0 | 0 | 0 | 0 | 0 | 3 |
| M1028 | 0.7 | 0.9 | 12 | 0 | 0 | 0 | 0 | 0 | 0 | 0 | 2 |
| M1029 | 0.7 | 0.9 | 12 | 0 | 0 | 0 | 0 | 0 | 0 | 0 | 3 |
| M1030 | 0.7 | 0.9 | 14 | 0 | 0 | 0 | 0 | 0 | 0 | 0 | 3 |

TABLE 3-continued

Alloy chemistries in weight percent, balance Fe, for selected alloys evaluated using thermodynamic models which meet thermodynamic criteria

| Alloy | B | C | Cr | Mn | Mo | Nb | Si | Ti | V | W | Zr |
|---|---|---|---|---|---|---|---|---|---|---|---|
| M1031 | 0.7 | 1 | 12 | 0 | 0 | 0 | 0 | 0 | 0 | 0 | 3 |
| M1032 | 0.7 | 1 | 12 | 0 | 0 | 0 | 0 | 0 | 0 | 0 | 4 |
| M1033 | 0.7 | 1 | 14 | 0 | 0 | 0 | 0 | 0 | 0 | 0 | 4 |
| M1034 | 0.7 | 1 | 16 | 0 | 0 | 0 | 0 | 0 | 0 | 0 | 4 |
| M1035 | 0.7 | 1.1 | 12 | 0 | 0 | 0 | 0 | 0 | 0 | 0 | 3 |
| M1036 | 0.7 | 1.1 | 12 | 0 | 0 | 0 | 0 | 0 | 0 | 0 | 4 |
| M1037 | 0.7 | 1.1 | 12 | 0 | 0 | 0 | 0 | 0 | 0 | 0 | 5 |
| M1038 | 0.7 | 1.1 | 14 | 0 | 0 | 0 | 0 | 0 | 0 | 0 | 5 |
| M1039 | 0.7 | 1.1 | 16 | 0 | 0 | 0 | 0 | 0 | 0 | 0 | 5 |
| M1040 | 0.7 | 1.2 | 12 | 0 | 0 | 0 | 0 | 0 | 0 | 0 | 3 |
| M1041 | 0.7 | 1.2 | 12 | 0 | 0 | 0 | 0 | 0 | 0 | 0 | 4 |
| M1042 | 0.7 | 1.2 | 12 | 0 | 0 | 0 | 0 | 0 | 0 | 0 | 5 |
| M1043 | 0.7 | 1.2 | 12 | 0 | 0 | 0 | 0 | 0 | 0 | 0 | 6 |
| M1044 | 0.7 | 1.2 | 14 | 0 | 0 | 0 | 0 | 0 | 0 | 0 | 6 |
| M1045 | 0.7 | 1.2 | 16 | 0 | 0 | 0 | 0 | 0 | 0 | 0 | 6 |
| M1046 | 0.7 | 1.3 | 12 | 0 | 0 | 0 | 0 | 0 | 0 | 0 | 4 |
| M1047 | 0.7 | 1.3 | 12 | 0 | 0 | 0 | 0 | 0 | 0 | 0 | 5 |
| M1048 | 0.7 | 1.3 | 12 | 0 | 0 | 0 | 0 | 0 | 0 | 0 | 6 |
| M1049 | 0.7 | 1.3 | 12 | 0 | 0 | 0 | 0 | 0 | 0 | 0 | 7 |
| M1050 | 0.7 | 1.3 | 14 | 0 | 0 | 0 | 0 | 0 | 0 | 0 | 7 |
| M1051 | 0.7 | 1.4 | 12 | 0 | 0 | 0 | 0 | 0 | 0 | 0 | 5 |
| M1052 | 0.7 | 1.4 | 12 | 0 | 0 | 0 | 0 | 0 | 0 | 0 | 6 |
| M1053 | 0.7 | 1.4 | 12 | 0 | 0 | 0 | 0 | 0 | 0 | 0 | 7 |
| M1054 | 0.7 | 1.5 | 12 | 0 | 0 | 0 | 0 | 0 | 0 | 0 | 6 |
| M1055 | 0.7 | 1.5 | 12 | 0 | 0 | 0 | 0 | 0 | 0 | 0 | 7 |
| M1056 | 0.7 | 1.5 | 12 | 0 | 0 | 0 | 0 | 0 | 0 | 0 | 8 |
| M1057 | 0.7 | 1.6 | 12 | 0 | 0 | 0 | 0 | 0 | 0 | 0 | 8 |
| M1058 | 0.7 | 1.7 | 12 | 0 | 0 | 0 | 0 | 0 | 0 | 0 | 7 |
| M1059 | 0.7 | 1.8 | 12 | 0 | 0 | 0 | 0 | 0 | 0 | 0 | 8 |
| M1060 | 0.8 | 0.8 | 12 | 0 | 0 | 0 | 0 | 0 | 0 | 0 | 2 |
| M1061 | 0.8 | 0.8 | 12 | 0 | 0 | 0 | 0 | 0 | 0 | 0 | 3 |
| M1062 | 0.8 | 0.9 | 12 | 0 | 0 | 0 | 0 | 0 | 0 | 0 | 3 |
| M1063 | 0.8 | 1 | 12 | 0 | 0 | 0 | 0 | 0 | 0 | 0 | 4 |
| M1064 | 0.8 | 1.1 | 12 | 0 | 0 | 0 | 0 | 0 | 0 | 0 | 5 |
| M1065 | 0.8 | 1.2 | 12 | 0 | 0 | 0 | 0 | 0 | 0 | 0 | 6 |
| M1066 | 0.4 | 0.9 | 16 | 1 | 1 | 0 | 0.5 | 2 | 0 | 0 | 0 |
| M1067 | 0.4 | 1 | 14 | 1 | 1 | 0 | 0.5 | 2 | 0 | 0 | 0 |
| M1068 | 0.4 | 1 | 16 | 1 | 1 | 0 | 0.5 | 2 | 0 | 0 | 0 |
| M1069 | 0.4 | 1.1 | 12 | 1 | 1 | 0 | 0.5 | 2 | 0 | 0 | 0 |
| M1070 | 0.4 | 1.1 | 14 | 1 | 1 | 0 | 0.5 | 2 | 0 | 0 | 0 |
| M1071 | 0.4 | 1.1 | 16 | 1 | 1 | 0 | 0.5 | 2 | 0 | 0 | 0 |
| M1072 | 0.4 | 1.2 | 12 | 1 | 1 | 0 | 0.5 | 2 | 0 | 0 | 0 |
| M1073 | 0.4 | 1.2 | 14 | 1 | 1 | 0 | 0.5 | 3 | 0 | 0 | 0 |
| M1074 | 0.4 | 1.2 | 16 | 1 | 1 | 0 | 0.5 | 2 | 0 | 0 | 0 |
| M1075 | 0.4 | 1.2 | 16 | 1 | 1 | 0 | 0.5 | 3 | 0 | 0 | 0 |
| M1076 | 0.4 | 1.3 | 12 | 1 | 1 | 0 | 0.5 | 3 | 0 | 0 | 0 |
| M1077 | 0.4 | 1.3 | 14 | 1 | 1 | 0 | 0.5 | 3 | 0 | 0 | 0 |
| M1078 | 0.4 | 1.3 | 16 | 1 | 1 | 0 | 0.5 | 2 | 0 | 0 | 0 |
| M1079 | 0.4 | 1.3 | 16 | 1 | 1 | 0 | 0.5 | 3 | 0 | 0 | 0 |
| M1080 | 0.4 | 1.4 | 12 | 1 | 1 | 0 | 0.5 | 3 | 0 | 0 | 0 |
| M1081 | 0.4 | 1.4 | 14 | 1 | 1 | 0 | 0.5 | 4 | 0 | 0 | 0 |
| M1082 | 0.4 | 1.4 | 16 | 1 | 1 | 0 | 0.5 | 2 | 0 | 0 | 0 |
| M1083 | 0.4 | 1.4 | 16 | 1 | 1 | 0 | 0.5 | 3 | 0 | 0 | 0 |
| M1084 | 0.4 | 1.4 | 16 | 1 | 1 | 0 | 0.5 | 4 | 0 | 0 | 0 |
| M1085 | 0.4 | 1.5 | 12 | 1 | 1 | 0 | 0.5 | 4 | 0 | 0 | 0 |
| M1086 | 0.4 | 1.5 | 14 | 1 | 1 | 0 | 0.5 | 2 | 0 | 0 | 0 |
| M1087 | 0.4 | 1.5 | 14 | 1 | 1 | 0 | 0.5 | 4 | 0 | 0 | 0 |
| M1088 | 0.4 | 1.5 | 16 | 1 | 1 | 0 | 0.5 | 2 | 0 | 0 | 0 |
| M1089 | 0.4 | 1.5 | 16 | 1 | 1 | 0 | 0.5 | 3 | 0 | 0 | 0 |
| M1090 | 0.4 | 1.5 | 16 | 1 | 1 | 0 | 0.5 | 4 | 0 | 0 | 0 |
| M1091 | 0.4 | 1.6 | 12 | 1 | 1 | 0 | 0.5 | 2 | 0 | 0 | 0 |
| M1092 | 0.4 | 1.6 | 12 | 1 | 1 | 0 | 0.5 | 4 | 0 | 0 | 0 |
| M1093 | 0.4 | 1.6 | 14 | 1 | 1 | 0 | 0.5 | 2 | 0 | 0 | 0 |
| M1094 | 0.4 | 1.6 | 16 | 1 | 1 | 0 | 0.5 | 3 | 0 | 0 | 0 |
| M1095 | 0.4 | 1.6 | 16 | 1 | 1 | 0 | 0.5 | 4 | 0 | 0 | 0 |
| M1096 | 0.4 | 1.6 | 16 | 1 | 1 | 0 | 0.5 | 5 | 0 | 0 | 0 |
| M1097 | 0.4 | 1.7 | 12 | 1 | 1 | 0 | 0.5 | 2 | 0 | 0 | 0 |
| M1098 | 0.4 | 1.7 | 14 | 1 | 1 | 0 | 0.5 | 5 | 0 | 0 | 0 |
| M1099 | 0.4 | 1.7 | 16 | 1 | 1 | 0 | 0.5 | 3 | 0 | 0 | 0 |
| M1100 | 0.4 | 1.7 | 16 | 1 | 1 | 0 | 0.5 | 4 | 0 | 0 | 0 |
| M1101 | 0.4 | 1.7 | 16 | 1 | 1 | 0 | 0.5 | 5 | 0 | 0 | 0 |
| M1102 | 0.4 | 1.8 | 12 | 1 | 1 | 0 | 0.5 | 5 | 0 | 0 | 0 |
| M1103 | 0.4 | 1.8 | 14 | 1 | 1 | 0 | 0.5 | 3 | 0 | 0 | 0 |
| M1104 | 0.4 | 1.8 | 16 | 1 | 1 | 0 | 0.5 | 3 | 0 | 0 | 0 |
| M1105 | 0.4 | 1.8 | 16 | 1 | 1 | 0 | 0.5 | 4 | 0 | 0 | 0 |

TABLE 3-continued

Alloy chemistries in weight percent, balance Fe, for selected alloys evaluated using thermodynamic models which meet thermodynamic criteria

| Alloy | B | C | Cr | Mn | Mo | Nb | Si | Ti | V | W | Zr |
|---|---|---|---|---|---|---|---|---|---|---|---|
| M1106 | 0.4 | 1.8 | 16 | 1 | 1 | 0 | 0.5 | 5 | 0 | 0 | 0 |
| M1107 | 0.4 | 1.8 | 16 | 1 | 1 | 0 | 0.5 | 6 | 0 | 0 | 0 |
| M1108 | 0.4 | 1.9 | 12 | 1 | 1 | 0 | 0.5 | 3 | 0 | 0 | 0 |
| M1109 | 0.4 | 1.9 | 14 | 1 | 1 | 0 | 0.5 | 3 | 0 | 0 | 0 |
| M1110 | 0.4 | 1.9 | 14 | 1 | 1 | 0 | 0.5 | 6 | 0 | 0 | 0 |
| M1111 | 0.4 | 1.9 | 16 | 1 | 1 | 0 | 0.5 | 4 | 0 | 0 | 0 |
| M1112 | 0.4 | 1.9 | 16 | 1 | 1 | 0 | 0.5 | 5 | 0 | 0 | 0 |
| M1113 | 0.4 | 1.9 | 16 | 1 | 1 | 0 | 0.5 | 6 | 0 | 0 | 0 |
| M1114 | 0.4 | 2 | 12 | 1 | 1 | 0 | 0.5 | 3 | 0 | 0 | 0 |
| M1115 | 0.4 | 2 | 12 | 1 | 1 | 0 | 0.5 | 6 | 0 | 0 | 0 |
| M1116 | 0.4 | 2 | 14 | 1 | 1 | 0 | 0.5 | 4 | 0 | 0 | 0 |
| M1117 | 0.4 | 2 | 16 | 1 | 1 | 0 | 0.5 | 4 | 0 | 0 | 0 |
| M1118 | 0.4 | 2 | 16 | 1 | 1 | 0 | 0.5 | 5 | 0 | 0 | 0 |
| M1119 | 0.4 | 2 | 16 | 1 | 1 | 0 | 0.5 | 6 | 0 | 0 | 0 |
| M1120 | 0.5 | 1 | 16 | 1 | 1 | 0 | 0.5 | 2 | 0 | 0 | 0 |
| M1121 | 0.5 | 1.1 | 16 | 1 | 1 | 0 | 0.5 | 2 | 0 | 0 | 0 |
| M1122 | 0.5 | 1.2 | 16 | 1 | 1 | 0 | 0.5 | 2 | 0 | 0 | 0 |
| M1123 | 0.5 | 1.2 | 16 | 1 | 1 | 0 | 0.5 | 3 | 0 | 0 | 0 |
| M1124 | 0.5 | 1.3 | 16 | 1 | 1 | 0 | 0.5 | 3 | 0 | 0 | 0 |
| M1125 | 0.5 | 1.4 | 16 | 1 | 1 | 0 | 0.5 | 3 | 0 | 0 | 0 |
| M1126 | 0.5 | 1.4 | 16 | 1 | 1 | 0 | 0.5 | 4 | 0 | 0 | 0 |
| M1127 | 0.5 | 1.5 | 16 | 1 | 1 | 0 | 0.5 | 3 | 0 | 0 | 0 |
| M1128 | 0.5 | 1.5 | 16 | 1 | 1 | 0 | 0.5 | 4 | 0 | 0 | 0 |
| M1129 | 0.5 | 1.6 | 16 | 1 | 1 | 0 | 0.5 | 4 | 0 | 0 | 0 |
| M1130 | 0.5 | 1.7 | 16 | 1 | 1 | 0 | 0.5 | 4 | 0 | 0 | 0 |
| M1131 | 0.5 | 1.7 | 16 | 1 | 1 | 0 | 0.5 | 5 | 0 | 0 | 0 |
| M1132 | 0.5 | 1.8 | 16 | 1 | 1 | 0 | 0.5 | 4 | 0 | 0 | 0 |
| M1133 | 0.5 | 1.8 | 16 | 1 | 1 | 0 | 0.5 | 5 | 0 | 0 | 0 |
| M1134 | 0.5 | 1.9 | 16 | 1 | 1 | 0 | 0.5 | 5 | 0 | 0 | 0 |
| M1135 | 0.5 | 1.9 | 16 | 1 | 1 | 0 | 0.5 | 6 | 0 | 0 | 0 |
| M1136 | 0.5 | 2 | 16 | 1 | 1 | 0 | 0.5 | 5 | 0 | 0 | 0 |
| M1137 | 0.5 | 2 | 16 | 1 | 1 | 0 | 0.5 | 6 | 0 | 0 | 0 |
| M1138 | 0.6 | 1 | 16 | 1 | 1 | 0 | 0.5 | 2 | 0 | 0 | 0 |
| M1139 | 0.6 | 1.1 | 16 | 1 | 1 | 0 | 0.5 | 2 | 0 | 0 | 0 |
| M1140 | 0.6 | 1.2 | 16 | 1 | 1 | 0 | 0.5 | 2 | 0 | 0 | 0 |
| M1141 | 0.6 | 1.2 | 16 | 1 | 1 | 0 | 0.5 | 3 | 0 | 0 | 0 |
| M1142 | 0.6 | 1.3 | 16 | 1 | 1 | 0 | 0.5 | 3 | 0 | 0 | 0 |
| M1143 | 0.6 | 1.4 | 16 | 1 | 1 | 0 | 0.5 | 3 | 0 | 0 | 0 |
| M1144 | 0.6 | 1.4 | 16 | 1 | 1 | 0 | 0.5 | 4 | 0 | 0 | 0 |
| M1145 | 0.6 | 1.5 | 16 | 1 | 1 | 0 | 0.5 | 3 | 0 | 0 | 0 |
| M1146 | 0.6 | 1.5 | 16 | 1 | 1 | 0 | 0.5 | 4 | 0 | 0 | 0 |
| M1147 | 0.6 | 1.6 | 16 | 1 | 1 | 0 | 0.5 | 4 | 0 | 0 | 0 |
| M1148 | 0.6 | 1.6 | 16 | 1 | 1 | 0 | 0.5 | 5 | 0 | 0 | 0 |
| M1149 | 0.6 | 1.7 | 16 | 1 | 1 | 0 | 0.5 | 4 | 0 | 0 | 0 |
| M1150 | 0.6 | 1.7 | 16 | 1 | 1 | 0 | 0.5 | 5 | 0 | 0 | 0 |
| M1151 | 0.6 | 1.8 | 16 | 1 | 1 | 0 | 0.5 | 4 | 0 | 0 | 0 |
| M1152 | 0.6 | 1.8 | 16 | 1 | 1 | 0 | 0.5 | 5 | 0 | 0 | 0 |
| M1153 | 0.6 | 1.8 | 16 | 1 | 1 | 0 | 0.5 | 6 | 0 | 0 | 0 |
| M1154 | 0.6 | 1.9 | 16 | 1 | 1 | 0 | 0.5 | 5 | 0 | 0 | 0 |
| M1155 | 0.6 | 1.9 | 16 | 1 | 1 | 0 | 0.5 | 6 | 0 | 0 | 0 |
| M1156 | 0.6 | 2 | 16 | 1 | 1 | 0 | 0.5 | 5 | 0 | 0 | 0 |
| M1157 | 0.6 | 2 | 16 | 1 | 1 | 0 | 0.5 | 6 | 0 | 0 | 0 |
| M1158 | 0.6 | 2 | 16 | 1 | 1 | 0 | 0.5 | 7 | 0 | 0 | 0 |
| M1159 | 0.7 | 0.9 | 16 | 1 | 1 | 0 | 0.5 | 2 | 0 | 0 | 0 |
| M1160 | 0.7 | 1 | 16 | 1 | 1 | 0 | 0.5 | 2 | 0 | 0 | 0 |
| M1161 | 0.7 | 1.1 | 16 | 1 | 1 | 0 | 0.5 | 2 | 0 | 0 | 0 |
| M1162 | 0.7 | 1.1 | 16 | 1 | 1 | 0 | 0.5 | 3 | 0 | 0 | 0 |
| M1163 | 0.7 | 1.2 | 16 | 1 | 1 | 0 | 0.5 | 3 | 0 | 0 | 0 |
| M1164 | 0.7 | 1.3 | 16 | 1 | 1 | 0 | 0.5 | 3 | 0 | 0 | 0 |
| M1165 | 0.7 | 1.3 | 16 | 1 | 1 | 0 | 0.5 | 4 | 0 | 0 | 0 |
| M1166 | 0.7 | 1.4 | 16 | 1 | 1 | 0 | 0.5 | 3 | 0 | 0 | 0 |
| M1167 | 0.7 | 1.4 | 16 | 1 | 1 | 0 | 0.5 | 4 | 0 | 0 | 0 |
| M1168 | 0.7 | 1.5 | 16 | 1 | 1 | 0 | 0.5 | 4 | 0 | 0 | 0 |
| M1169 | 0.7 | 1.5 | 16 | 1 | 1 | 0 | 0.5 | 5 | 0 | 0 | 0 |
| M1170 | 0.7 | 1.6 | 16 | 1 | 1 | 0 | 0.5 | 4 | 0 | 0 | 0 |
| M1171 | 0.7 | 1.6 | 16 | 1 | 1 | 0 | 0.5 | 5 | 0 | 0 | 0 |
| M1172 | 0.7 | 1.7 | 16 | 1 | 1 | 0 | 0.5 | 4 | 0 | 0 | 0 |
| M1173 | 0.7 | 1.7 | 16 | 1 | 1 | 0 | 0.5 | 5 | 0 | 0 | 0 |
| M1174 | 0.7 | 1.8 | 16 | 1 | 1 | 0 | 0.5 | 5 | 0 | 0 | 0 |
| M1175 | 0.7 | 1.8 | 16 | 1 | 1 | 0 | 0.5 | 6 | 0 | 0 | 0 |
| M1176 | 0.7 | 1.9 | 16 | 1 | 1 | 0 | 0.5 | 5 | 0 | 0 | 0 |
| M1177 | 0.7 | 1.9 | 16 | 1 | 1 | 0 | 0.5 | 6 | 0 | 0 | 0 |
| M1178 | 0.7 | 2 | 14 | 1 | 1 | 0 | 0.5 | 7 | 0 | 0 | 0 |
| M1179 | 0.7 | 2 | 16 | 1 | 1 | 0 | 0.5 | 5 | 0 | 0 | 0 |
| M1180 | 0.7 | 2 | 16 | 1 | 1 | 0 | 0.5 | 6 | 0 | 0 | 0 |

TABLE 3-continued

Alloy chemistries in weight percent, balance Fe, for selected alloys evaluated using thermodynamic models which meet thermodynamic criteria

| Alloy | B | C | Cr | Mn | Mo | Nb | Si | Ti | V | W | Zr |
|---|---|---|---|---|---|---|---|---|---|---|---|
| M1181 | 0.7 | 2 | 16 | 1 | 1 | 0 | 0.5 | 7 | 0 | 0 | 0 |
| M1182 | 0.8 | 0.9 | 16 | 1 | 1 | 0 | 0.5 | 2 | 0 | 0 | 0 |
| M1183 | 0.8 | 1 | 16 | 1 | 1 | 0 | 0.5 | 2 | 0 | 0 | 0 |
| M1184 | 0.8 | 1.1 | 16 | 1 | 1 | 0 | 0.5 | 2 | 0 | 0 | 0 |
| M1185 | 0.8 | 1.1 | 16 | 1 | 1 | 0 | 0.5 | 3 | 0 | 0 | 0 |
| M1186 | 0.8 | 1.2 | 16 | 1 | 1 | 0 | 0.5 | 3 | 0 | 0 | 0 |
| M1187 | 0.8 | 1.3 | 16 | 1 | 1 | 0 | 0.5 | 3 | 0 | 0 | 0 |
| M1188 | 0.8 | 1.3 | 16 | 1 | 1 | 0 | 0.5 | 4 | 0 | 0 | 0 |
| M1189 | 0.8 | 1.4 | 16 | 1 | 1 | 0 | 0.5 | 4 | 0 | 0 | 0 |
| M1190 | 0.8 | 1.5 | 16 | 1 | 1 | 0 | 0.5 | 4 | 0 | 0 | 0 |
| M1191 | 0.8 | 1.5 | 16 | 1 | 1 | 0 | 0.5 | 5 | 0 | 0 | 0 |
| M1192 | 0.8 | 1.6 | 16 | 1 | 1 | 0 | 0.5 | 4 | 0 | 0 | 0 |
| M1193 | 0.8 | 1.6 | 16 | 1 | 1 | 0 | 0.5 | 5 | 0 | 0 | 0 |
| M1194 | 0.8 | 1.7 | 16 | 1 | 1 | 0 | 0.5 | 5 | 0 | 0 | 0 |
| M1195 | 0.8 | 1.7 | 16 | 1 | 1 | 0 | 0.5 | 6 | 0 | 0 | 0 |
| M1196 | 0.8 | 1.8 | 16 | 1 | 1 | 0 | 0.5 | 5 | 0 | 0 | 0 |
| M1197 | 0.8 | 1.8 | 16 | 1 | 1 | 0 | 0.5 | 6 | 0 | 0 | 0 |
| M1198 | 0.8 | 1.9 | 16 | 1 | 1 | 0 | 0.5 | 5 | 0 | 0 | 0 |
| M1199 | 0.8 | 1.9 | 16 | 1 | 1 | 0 | 0.5 | 6 | 0 | 0 | 0 |
| M1200 | 0.8 | 1.9 | 16 | 1 | 1 | 0 | 0.5 | 7 | 0 | 0 | 0 |
| M1201 | 0.8 | 2 | 14 | 1 | 1 | 0 | 0.5 | 7 | 0 | 0 | 0 |
| M1202 | 0.8 | 2 | 16 | 1 | 1 | 0 | 0.5 | 6 | 0 | 0 | 0 |
| M1203 | 0.8 | 2 | 16 | 1 | 1 | 0 | 0.5 | 7 | 0 | 0 | 0 |
| M1204 | 0.9 | 0.8 | 16 | 1 | 1 | 0 | 0.5 | 2 | 0 | 0 | 0 |
| M1205 | 0.9 | 0.9 | 16 | 1 | 1 | 0 | 0.5 | 2 | 0 | 0 | 0 |
| M1206 | 0.9 | 1 | 16 | 1 | 1 | 0 | 0.5 | 3 | 0 | 0 | 0 |
| M1207 | 0.9 | 1.1 | 16 | 1 | 1 | 0 | 0.5 | 3 | 0 | 0 | 0 |
| M1208 | 0.9 | 1.2 | 16 | 1 | 1 | 0 | 0.5 | 3 | 0 | 0 | 0 |
| M1209 | 0.9 | 1.2 | 16 | 1 | 1 | 0 | 0.5 | 4 | 0 | 0 | 0 |
| M1210 | 0.9 | 1.3 | 16 | 1 | 1 | 0 | 0.5 | 4 | 0 | 0 | 0 |
| M1211 | 0.9 | 1.4 | 16 | 1 | 1 | 0 | 0.5 | 4 | 0 | 0 | 0 |
| M1212 | 0.9 | 1.4 | 16 | 1 | 1 | 0 | 0.5 | 5 | 0 | 0 | 0 |
| M1213 | 0.9 | 1.5 | 16 | 1 | 1 | 0 | 0.5 | 4 | 0 | 0 | 0 |
| M1214 | 0.9 | 1.5 | 16 | 1 | 1 | 0 | 0.5 | 5 | 0 | 0 | 0 |
| M1215 | 0.9 | 1.6 | 16 | 1 | 1 | 0 | 0.5 | 5 | 0 | 0 | 0 |
| M1216 | 0.9 | 1.7 | 16 | 1 | 1 | 0 | 0.5 | 5 | 0 | 0 | 0 |
| M1217 | 0.9 | 1.7 | 16 | 1 | 1 | 0 | 0.5 | 6 | 0 | 0 | 0 |
| M1218 | 0.9 | 1.8 | 16 | 1 | 1 | 0 | 0.5 | 5 | 0 | 0 | 0 |
| M1219 | 0.9 | 1.8 | 16 | 1 | 1 | 0 | 0.5 | 6 | 0 | 0 | 0 |
| M1220 | 0.9 | 1.9 | 14 | 1 | 1 | 0 | 0.5 | 7 | 0 | 0 | 0 |
| M1221 | 0.9 | 1.9 | 16 | 1 | 1 | 0 | 0.5 | 6 | 0 | 0 | 0 |
| M1222 | 0.9 | 1.9 | 16 | 1 | 1 | 0 | 0.5 | 7 | 0 | 0 | 0 |
| M1223 | 0.9 | 2 | 16 | 1 | 1 | 0 | 0.5 | 6 | 0 | 0 | 0 |
| M1224 | 0.9 | 2 | 16 | 1 | 1 | 0 | 0.5 | 7 | 0 | 0 | 0 |
| M1225 | 0.1 | 1 | 5 | 1 | 1 | 3 | 0.65 | 1.3 | 0.5 | 0 | 0 |
| M1226 | 0.1 | 1 | 5 | 1 | 1 | 3 | 0.65 | 1.3 | 0.5 | 2.5 | 0 |
| M1227 | 0.2 | 1 | 5 | 1 | 1 | 3 | 0.65 | 1.3 | 0.5 | 0 | 0 |
| M1228 | 0.2 | 1 | 5 | 1 | 1 | 3 | 0.65 | 1.3 | 0.5 | 0.5 | 0 |
| M1229 | 0.2 | 1 | 5 | 1 | 1 | 3 | 0.65 | 1.3 | 0.5 | 1 | 0 |
| M1230 | 0.2 | 1 | 5 | 1 | 1 | 3 | 0.65 | 1.3 | 0.5 | 1.5 | 0 |
| M1231 | 0.2 | 1 | 5 | 1 | 1 | 3 | 0.65 | 1.3 | 0.5 | 2 | 0 |
| M1232 | 0.2 | 1 | 5 | 1 | 1 | 3 | 0.65 | 1.3 | 0.5 | 2.5 | 0 |
| M1233 | 0.2 | 1 | 5 | 1 | 1 | 3 | 0.65 | 1.3 | 0.5 | 3 | 0 |
| M1234 | 0.2 | 1 | 5 | 1 | 1 | 3 | 0.65 | 1.3 | 0.5 | 3.5 | 0 |
| M1235 | 0.2 | 1 | 5 | 1 | 1 | 3 | 0.65 | 1.3 | 0.5 | 4 | 0 |
| M1236 | 0.2 | 1.1 | 5 | 1 | 1 | 3 | 0.65 | 1.3 | 0.5 | 0 | 0 |
| M1237 | 0.2 | 1.1 | 5 | 1 | 1 | 3 | 0.65 | 1.3 | 0.5 | 0.5 | 0 |
| M1238 | 0.2 | 1.1 | 5 | 1 | 1 | 3 | 0.65 | 1.3 | 0.5 | 1 | 0 |
| M1239 | 0.2 | 1.1 | 5 | 1 | 1 | 3 | 0.65 | 1.3 | 0.5 | 1.5 | 0 |
| M1240 | 0.2 | 1.1 | 5 | 1 | 1 | 3 | 0.65 | 1.3 | 0.5 | 2 | 0 |
| M1241 | 1.1 | 0.9 | 0.5 | 0 | 1 | 3.5 | 0.5 | 1 | 0.5 | 0 | 0 |
| M1242 | 1.1 | 0.9 | 3 | 0 | 1 | 4.5 | 0.5 | 1.5 | 0.5 | 0 | 0 |
| M1243 | 0.3 | 1 | 5 | 1 | 1 | 3 | 0.65 | 1.3 | 0.5 | 0 | 0 |
| M1244 | 0.3 | 1 | 5 | 1 | 1 | 3 | 0.65 | 1.3 | 0.5 | 0.5 | 0 |
| M1245 | 0.3 | 1 | 5 | 1 | 1 | 3 | 0.65 | 1.3 | 0.5 | 1 | 0 |
| M1246 | 0.3 | 1 | 5 | 1 | 1 | 3 | 0.65 | 1.3 | 0.5 | 1.5 | 0 |
| M1247 | 0.3 | 1 | 5 | 1 | 1 | 3 | 0.65 | 1.3 | 0.5 | 2 | 0 |
| M1248 | 0.3 | 1 | 5 | 1 | 1 | 3 | 0.65 | 1.3 | 0.5 | 2.5 | 0 |
| M1249 | 0.3 | 1 | 5 | 1 | 1 | 3 | 0.65 | 1.3 | 0.5 | 3 | 0 |
| M1250 | 0.3 | 1 | 5 | 1 | 1 | 3 | 0.65 | 1.3 | 0.5 | 3.5 | 0 |
| M1251 | 0.3 | 1 | 5 | 1 | 1 | 3 | 0.65 | 1.3 | 0.5 | 4 | 0 |
| M1252 | 0.3 | 1.1 | 5 | 1 | 1 | 3 | 0.65 | 1.3 | 0.5 | 0 | 0 |
| M1253 | 0.3 | 1.1 | 5 | 1 | 1 | 3 | 0.65 | 1.3 | 0.5 | 0.5 | 0 |
| M1254 | 0.3 | 1.1 | 5 | 1 | 1 | 3 | 0.65 | 1.3 | 0.5 | 1 | 0 |
| M1255 | 0.3 | 1.1 | 5 | 1 | 1 | 3 | 0.65 | 1.3 | 0.5 | 1.5 | 0 |

TABLE 3-continued

Alloy chemistries in weight percent, balance Fe, for selected alloys evaluated using thermodynamic models which meet thermodynamic criteria

| Alloy | B | C | Cr | Mn | Mo | Nb | Si | Ti | V | W | Zr |
|---|---|---|---|---|---|---|---|---|---|---|---|
| M1256 | 0.3 | 1.1 | 5 | 1 | 1 | 3 | 0.65 | 1.3 | 0.5 | 2 | 0 |
| M1257 | 0.3 | 1.1 | 5 | 1 | 1 | 3 | 0.65 | 1.3 | 0.5 | 2.5 | 0 |
| M1258 | 0.3 | 1.1 | 5 | 1 | 1 | 3 | 0.65 | 1.3 | 0.5 | 3 | 0 |
| M1259 | 0.3 | 1.1 | 5 | 1 | 1 | 3 | 0.65 | 1.3 | 0.5 | 3.5 | 0 |
| M1260 | 0.3 | 1.1 | 5 | 1 | 1 | 3 | 0.65 | 1.3 | 0.5 | 4 | 0 |
| M1261 | 0.3 | 1.2 | 5 | 1 | 1 | 3 | 0.65 | 1.3 | 0.5 | 0 | 0 |
| M1262 | 0.3 | 1.2 | 5 | 1 | 1 | 3 | 0.65 | 1.3 | 0.5 | 0.5 | 0 |
| M1263 | 0.3 | 1.2 | 5 | 1 | 1 | 3 | 0.65 | 1.3 | 0.5 | 1 | 0 |
| M1264 | 0.3 | 1.2 | 5 | 1 | 1 | 3 | 0.65 | 1.3 | 0.5 | 1.5 | 0 |
| M1265 | 0.3 | 1.2 | 5 | 1 | 1 | 3 | 0.65 | 1.3 | 0.5 | 2 | 0 |
| M1266 | 0.3 | 1.2 | 5 | 1 | 1 | 3 | 0.65 | 1.3 | 0.5 | 2.5 | 0 |
| M1267 | 0.3 | 1.2 | 5 | 1 | 1 | 3 | 0.65 | 1.3 | 0.5 | 3 | 0 |
| M1268 | 0.3 | 1.2 | 5 | 1 | 1 | 3 | 0.65 | 1.3 | 0.5 | 3.5 | 0 |
| M1269 | 0.3 | 1.2 | 5 | 1 | 1 | 3 | 0.65 | 1.3 | 0.5 | 4 | 0 |
| M1270 | 0.3 | 1.3 | 5 | 1 | 1 | 3 | 0.65 | 1.3 | 0.5 | 0 | 0 |
| M1271 | 0.3 | 1.3 | 5 | 1 | 1 | 3 | 0.65 | 1.3 | 0.5 | 0.5 | 0 |
| M1272 | 0.3 | 1.3 | 5 | 1 | 1 | 3 | 0.65 | 1.3 | 0.5 | 1 | 0 |
| M1273 | 0.3 | 1.3 | 5 | 1 | 1 | 3 | 0.65 | 1.3 | 0.5 | 1.5 | 0 |
| M1274 | 0.3 | 1.3 | 5 | 1 | 1 | 3 | 0.65 | 1.3 | 0.5 | 2 | 0 |
| M1275 | 0.3 | 1.3 | 5 | 1 | 1 | 3 | 0.65 | 1.3 | 0.5 | 2.5 | 0 |
| M1276 | 0.3 | 1.4 | 5 | 1 | 1 | 3 | 0.65 | 1.3 | 0.5 | 0 | 0 |
| M1277 | 0.4 | 1 | 5 | 1 | 1 | 3 | 0.65 | 1.3 | 0.5 | 0 | 0 |
| M1278 | 0.4 | 1 | 5 | 1 | 1 | 3 | 0.65 | 1.3 | 0.5 | 0.5 | 0 |
| M1279 | 0.4 | 1 | 5 | 1 | 1 | 3 | 0.65 | 1.3 | 0.5 | 1 | 0 |
| M1280 | 0.4 | 1 | 5 | 1 | 1 | 3 | 0.65 | 1.3 | 0.5 | 1.5 | 0 |
| M1281 | 0.4 | 1 | 5 | 1 | 1 | 3 | 0.65 | 1.3 | 0.5 | 2 | 0 |
| M1282 | 0.4 | 1 | 5 | 1 | 1 | 3 | 0.65 | 1.3 | 0.5 | 2.5 | 0 |
| M1283 | 0.4 | 1 | 5 | 1 | 1 | 3 | 0.65 | 1.3 | 0.5 | 3 | 0 |
| M1284 | 0.4 | 1 | 5 | 1 | 1 | 3 | 0.65 | 1.3 | 0.5 | 3.5 | 0 |
| M1285 | 0.4 | 1 | 5 | 1 | 1 | 3 | 0.65 | 1.3 | 0.5 | 4 | 0 |
| M1286 | 0.4 | 1.1 | 5 | 1 | 1 | 3 | 0.65 | 1.3 | 0.5 | 0 | 0 |
| M1287 | 0.4 | 1.1 | 5 | 1 | 1 | 3 | 0.65 | 1.3 | 0.5 | 0.5 | 0 |
| M1288 | 0.4 | 1.1 | 5 | 1 | 1 | 3 | 0.65 | 1.3 | 0.5 | 1 | 0 |
| M1289 | 0.4 | 1.1 | 5 | 1 | 1 | 3 | 0.65 | 1.3 | 0.5 | 1.5 | 0 |
| M1290 | 0.4 | 1.1 | 5 | 1 | 1 | 3 | 0.65 | 1.3 | 0.5 | 2 | 0 |
| M1291 | 0.4 | 1.1 | 5 | 1 | 1 | 3 | 0.65 | 1.3 | 0.5 | 2.5 | 0 |
| M1292 | 0.4 | 1.1 | 5 | 1 | 1 | 3 | 0.65 | 1.3 | 0.5 | 3 | 0 |
| M1293 | 0.4 | 1.1 | 5 | 1 | 1 | 3 | 0.65 | 1.3 | 0.5 | 3.5 | 0 |
| M1294 | 0.4 | 1.1 | 5 | 1 | 1 | 3 | 0.65 | 1.3 | 0.5 | 4 | 0 |
| M1295 | 0.4 | 1.2 | 5 | 1 | 1 | 3 | 0.65 | 1.3 | 0.5 | 0 | 0 |
| M1296 | 0.4 | 1.2 | 5 | 1 | 1 | 3 | 0.65 | 1.3 | 0.5 | 0.5 | 0 |
| M1297 | 0.4 | 1.2 | 5 | 1 | 1 | 3 | 0.65 | 1.3 | 0.5 | 1 | 0 |
| M1298 | 0.4 | 1.2 | 5 | 1 | 1 | 3 | 0.65 | 1.3 | 0.5 | 1.5 | 0 |
| M1299 | 0.4 | 1.2 | 5 | 1 | 1 | 3 | 0.65 | 1.3 | 0.5 | 2 | 0 |
| M1300 | 0.4 | 1.2 | 5 | 1 | 1 | 3 | 0.65 | 1.3 | 0.5 | 2.5 | 0 |
| M1301 | 0.4 | 1.2 | 5 | 1 | 1 | 3 | 0.65 | 1.3 | 0.5 | 3 | 0 |
| M1302 | 0.4 | 1.2 | 5 | 1 | 1 | 3 | 0.65 | 1.3 | 0.5 | 3.5 | 0 |
| M1303 | 0.4 | 1.2 | 5 | 1 | 1 | 3 | 0.65 | 1.3 | 0.5 | 4 | 0 |
| M1304 | 0.4 | 1.3 | 5 | 1 | 1 | 3 | 0.65 | 1.3 | 0.5 | 0 | 0 |
| M1305 | 0.4 | 1.3 | 5 | 1 | 1 | 3 | 0.65 | 1.3 | 0.5 | 0.5 | 0 |
| M1306 | 0.4 | 1.3 | 5 | 1 | 1 | 3 | 0.65 | 1.3 | 0.5 | 1 | 0 |
| M1307 | 0.4 | 1.3 | 5 | 1 | 1 | 3 | 0.65 | 1.3 | 0.5 | 1.5 | 0 |
| M1308 | 0.4 | 1.3 | 5 | 1 | 1 | 3 | 0.65 | 1.3 | 0.5 | 2 | 0 |
| M1309 | 0.4 | 1.3 | 5 | 1 | 1 | 3 | 0.65 | 1.3 | 0.5 | 2.5 | 0 |
| M1310 | 0.4 | 1.3 | 5 | 1 | 1 | 3 | 0.65 | 1.3 | 0.5 | 3 | 0 |
| M1311 | 0.4 | 1.3 | 5 | 1 | 1 | 3 | 0.65 | 1.3 | 0.5 | 3.5 | 0 |
| M1312 | 0.4 | 1.3 | 5 | 1 | 1 | 3 | 0.65 | 1.3 | 0.5 | 4 | 0 |
| M1313 | 0.4 | 1.4 | 5 | 1 | 1 | 3 | 0.65 | 1.3 | 0.5 | 0 | 0 |
| M1314 | 0.4 | 1.4 | 5 | 1 | 1 | 3 | 0.65 | 1.3 | 0.5 | 0.5 | 0 |
| M1315 | 0.4 | 1.4 | 5 | 1 | 1 | 3 | 0.65 | 1.3 | 0.5 | 1 | 0 |
| M1316 | 0.4 | 1.4 | 5 | 1 | 1 | 3 | 0.65 | 1.3 | 0.5 | 1.5 | 0 |
| M1317 | 0.4 | 1.4 | 5 | 1 | 1 | 3 | 0.65 | 1.3 | 0.5 | 2 | 0 |
| M1318 | 0.4 | 1.4 | 5 | 1 | 1 | 3 | 0.65 | 1.3 | 0.5 | 2.5 | 0 |
| M1319 | 0.4 | 1.4 | 5 | 1 | 1 | 3 | 0.65 | 1.3 | 0.5 | 3 | 0 |
| M1320 | 0.4 | 1.4 | 5 | 1 | 1 | 3 | 0.65 | 1.3 | 0.5 | 3.5 | 0 |
| M1321 | 0.4 | 1.4 | 5 | 1 | 1 | 3 | 0.65 | 1.3 | 0.5 | 4 | 0 |
| M1322 | 0.5 | 1 | 5 | 1 | 1 | 3 | 0.65 | 1.3 | 0.5 | 1 | 0 |
| M1323 | 0.5 | 1 | 5 | 1 | 1 | 3 | 0.65 | 1.3 | 0.5 | 1.5 | 0 |
| M1324 | 0.5 | 1 | 5 | 1 | 1 | 3 | 0.65 | 1.3 | 0.5 | 2 | 0 |
| M1325 | 0.5 | 1 | 5 | 1 | 1 | 3 | 0.65 | 1.3 | 0.5 | 2.5 | 0 |
| M1326 | 0.5 | 1 | 5 | 1 | 1 | 3 | 0.65 | 1.3 | 0.5 | 3.5 | 0 |
| M1327 | 0.5 | 1 | 5 | 1 | 1 | 3 | 0.65 | 1.3 | 0.5 | 4 | 0 |
| M1328 | 0.5 | 1.1 | 5 | 1 | 1 | 3 | 0.65 | 1.3 | 0.5 | 0 | 0 |
| M1329 | 0.5 | 1.1 | 5 | 1 | 1 | 3 | 0.65 | 1.3 | 0.5 | 0.5 | 0 |
| M1330 | 0.5 | 1.1 | 5 | 1 | 1 | 3 | 0.65 | 1.3 | 0.5 | 1 | 0 |

TABLE 3-continued

Alloy chemistries in weight percent, balance Fe, for selected alloys evaluated using thermodynamic models which meet thermodynamic criteria

| Alloy | B | C | Cr | Mn | Mo | Nb | Si | Ti | V | W | Zr |
|---|---|---|---|---|---|---|---|---|---|---|---|
| M1331 | 0.5 | 1.1 | 5 | 1 | 1 | 3 | 0.65 | 1.3 | 0.5 | 1.5 | 0 |
| M1332 | 0.5 | 1.1 | 5 | 1 | 1 | 3 | 0.65 | 1.3 | 0.5 | 2 | 0 |
| M1333 | 0.5 | 1.1 | 5 | 1 | 1 | 3 | 0.65 | 1.3 | 0.5 | 2.5 | 0 |
| M1334 | 0.5 | 1.1 | 5 | 1 | 1 | 3 | 0.65 | 1.3 | 0.5 | 3 | 0 |
| M1335 | 0.5 | 1.1 | 5 | 1 | 1 | 3 | 0.65 | 1.3 | 0.5 | 3.5 | 0 |
| M1336 | 0.5 | 1.1 | 5 | 1 | 1 | 3 | 0.65 | 1.3 | 0.5 | 4 | 0 |
| M1337 | 0.5 | 1.2 | 5 | 1 | 1 | 3 | 0.65 | 1.3 | 0.5 | 0 | 0 |
| M1338 | 0.5 | 1.2 | 5 | 1 | 1 | 3 | 0.65 | 1.3 | 0.5 | 0.5 | 0 |
| M1339 | 0.5 | 1.2 | 5 | 1 | 1 | 3 | 0.65 | 1.3 | 0.5 | 1 | 0 |
| M1340 | 0.5 | 1.2 | 5 | 1 | 1 | 3 | 0.65 | 1.3 | 0.5 | 1.5 | 0 |
| M1341 | 0.5 | 1.2 | 5 | 1 | 1 | 3 | 0.65 | 1.3 | 0.5 | 2 | 0 |
| M1342 | 0.5 | 1.2 | 5 | 1 | 1 | 3 | 0.65 | 1.3 | 0.5 | 2.5 | 0 |
| M1343 | 0.5 | 1.2 | 5 | 1 | 1 | 3 | 0.65 | 1.3 | 0.5 | 3 | 0 |
| M1344 | 0.5 | 1.2 | 5 | 1 | 1 | 3 | 0.65 | 1.3 | 0.5 | 3.5 | 0 |
| M1345 | 0.5 | 1.2 | 5 | 1 | 1 | 3 | 0.65 | 1.3 | 0.5 | 4 | 0 |
| M1346 | 0.5 | 1.3 | 5 | 1 | 1 | 3 | 0.65 | 1.3 | 0.5 | 0 | 0 |
| M1347 | 0.5 | 1.3 | 5 | 1 | 1 | 3 | 0.65 | 1.3 | 0.5 | 0.5 | 0 |
| M1348 | 0.5 | 1.3 | 5 | 1 | 1 | 3 | 0.65 | 1.3 | 0.5 | 1 | 0 |
| M1349 | 0.5 | 1.3 | 5 | 1 | 1 | 3 | 0.65 | 1.3 | 0.5 | 1.5 | 0 |
| M1350 | 0.5 | 1.3 | 5 | 1 | 1 | 3 | 0.65 | 1.3 | 0.5 | 2 | 0 |
| M1351 | 0.5 | 1.3 | 5 | 1 | 1 | 3 | 0.65 | 1.3 | 0.5 | 2.5 | 0 |
| M1352 | 0.5 | 1.3 | 5 | 1 | 1 | 3 | 0.65 | 1.3 | 0.5 | 3 | 0 |
| M1353 | 0.5 | 1.3 | 5 | 1 | 1 | 3 | 0.65 | 1.3 | 0.5 | 3.5 | 0 |
| M1354 | 0.5 | 1.3 | 5 | 1 | 1 | 3 | 0.65 | 1.3 | 0.5 | 4 | 0 |
| M1355 | 0.5 | 1.4 | 5 | 1 | 1 | 3 | 0.65 | 1.3 | 0.5 | 0 | 0 |
| M1356 | 0.5 | 1.4 | 5 | 1 | 1 | 3 | 0.65 | 1.3 | 0.5 | 0.5 | 0 |
| M1357 | 0.5 | 1.4 | 5 | 1 | 1 | 3 | 0.65 | 1.3 | 0.5 | 1 | 0 |
| M1358 | 0.5 | 1.4 | 5 | 1 | 1 | 3 | 0.65 | 1.3 | 0.5 | 1.5 | 0 |
| M1359 | 0.5 | 1.4 | 5 | 1 | 1 | 3 | 0.65 | 1.3 | 0.5 | 2 | 0 |
| M1360 | 0.5 | 1.4 | 5 | 1 | 1 | 3 | 0.65 | 1.3 | 0.5 | 2.5 | 0 |
| M1361 | 0.5 | 1.4 | 5 | 1 | 1 | 3 | 0.65 | 1.3 | 0.5 | 3 | 0 |
| M1362 | 0.5 | 1.4 | 5 | 1 | 1 | 3 | 0.65 | 1.3 | 0.5 | 3.5 | 0 |
| M1363 | 0.5 | 1.4 | 5 | 1 | 1 | 3 | 0.65 | 1.3 | 0.5 | 4 | 0 |
| M1364 | 0.4 | 1.7 | 12 | 1 | 1 | 0 | 0.5 | 0 | 10 | 0 | 0 |
| M1365 | 0.4 | 1.8 | 12 | 1 | 1 | 0 | 0.5 | 0 | 10 | 0 | 0 |
| M1366 | 0.4 | 1.9 | 12 | 1 | 1 | 0 | 0.5 | 0 | 10 | 0 | 0 |
| M1367 | 0.5 | 0.8 | 16 | 1 | 1 | 0 | 0.5 | 0 | 4 | 0 | 0 |
| M1368 | 0.5 | 0.9 | 12 | 1 | 1 | 0 | 0.5 | 0 | 2 | 0 | 0 |
| M1369 | 0.5 | 0.9 | 12 | 1 | 1 | 0 | 0.5 | 0 | 3 | 0 | 0 |
| M1370 | 0.5 | 0.9 | 14 | 1 | 1 | 0 | 0.5 | 0 | 3 | 0 | 0 |
| M1371 | 0.5 | 1 | 14 | 1 | 1 | 0 | 0.5 | 0 | 3 | 0 | 0 |
| M1372 | 0.5 | 1.5 | 12 | 1 | 1 | 0 | 0.5 | 0 | 5 | 0 | 0 |
| M1373 | 0.5 | 1.5 | 14 | 1 | 1 | 0 | 0.5 | 0 | 5 | 0 | 0 |
| M1374 | 1.1 | 0.9 | 3.5 | 0 | 1 | 2.5 | 0.5 | 1 | 0.5 | 0 | 0 |
| M1375 | 1.1 | 0.9 | 3.5 | 0 | 1 | 4 | 0.5 | 1.5 | 0.5 | 0 | 0 |
| M1376 | 1.1 | 0.9 | 4 | 0 | 1 | 2.5 | 0.5 | 0.5 | 0.5 | 0 | 0 |
| M1377 | 1.1 | 0.9 | 4 | 0 | 1 | 2.5 | 0.5 | 1 | 0.5 | 0 | 0 |
| M1378 | 1.1 | 0.9 | 4 | 0 | 1 | 3 | 0.5 | 1 | 0.5 | 0 | 0 |
| M1379 | 1.1 | 0.9 | 4 | 0 | 1 | 3.5 | 0.5 | 1 | 0.5 | 0 | 0 |
| M1380 | 1.1 | 0.9 | 4 | 0 | 1 | 4 | 0.5 | 1 | 0.5 | 0 | 0 |
| M1381 | 1.1 | 0.9 | 4.5 | 0 | 1 | 2.5 | 0.5 | 1 | 0.5 | 0 | 0 |
| M1382 | 1.1 | 0.9 | 4.5 | 0 | 1 | 3 | 0.5 | 1 | 0.5 | 0 | 0 |
| M1383 | 1.1 | 0.9 | 4.5 | 0 | 1 | 3.5 | 0.5 | 1 | 0.5 | 0 | 0 |
| M1384 | 1.1 | 0.9 | 4.5 | 0 | 1 | 4 | 0.5 | 1 | 0.5 | 0 | 0 |
| M1385 | 1.1 | 0.65 | 0.5 | 0 | 1 | 2.5 | 0.5 | 0.5 | 0.5 | 0 | 0 |
| M1386 | 1.1 | 0.65 | 3 | 0 | 1 | 2.5 | 0.5 | 0 | 0.5 | 0 | 0 |
| M1387 | 1.1 | 0.65 | 3 | 0 | 1 | 2.5 | 0.5 | 0.5 | 0.5 | 0 | 0 |
| M1388 | 0.6 | 0.7 | 14 | 1 | 1 | 0 | 0.5 | 0 | 3 | 0 | 0 |
| M1389 | 0.6 | 0.7 | 14 | 1 | 1 | 0 | 0.5 | 0 | 4 | 0 | 0 |
| M1390 | 0.6 | 0.7 | 14 | 1 | 1 | 0 | 0.5 | 0 | 5 | 0 | 0 |
| M1391 | 0.6 | 0.7 | 14 | 1 | 1 | 0 | 0.5 | 0 | 6 | 0 | 0 |
| M1392 | 0.6 | 0.7 | 16 | 1 | 1 | 0 | 0.5 | 0 | 4 | 0 | 0 |
| M1393 | 0.6 | 0.7 | 16 | 1 | 1 | 0 | 0.5 | 0 | 5 | 0 | 0 |
| M1394 | 0.6 | 0.7 | 16 | 1 | 1 | 0 | 0.5 | 0 | 6 | 0 | 0 |
| M1395 | 0.6 | 0.7 | 16 | 1 | 1 | 0 | 0.5 | 0 | 7 | 0 | 0 |
| M1396 | 0.6 | 0.8 | 12 | 1 | 1 | 0 | 0.5 | 0 | 2 | 0 | 0 |
| M1397 | 0.6 | 0.8 | 12 | 1 | 1 | 0 | 0.5 | 0 | 3 | 0 | 0 |
| M1398 | 0.6 | 0.8 | 12 | 1 | 1 | 0 | 0.5 | 0 | 4 | 0 | 0 |
| M1399 | 0.6 | 0.8 | 14 | 1 | 1 | 0 | 0.5 | 0 | 3 | 0 | 0 |
| M1400 | 0.6 | 0.8 | 14 | 1 | 1 | 0 | 0.5 | 0 | 4 | 0 | 0 |
| M1401 | 0.6 | 0.8 | 14 | 1 | 1 | 0 | 0.5 | 0 | 5 | 0 | 0 |
| M1402 | 0.6 | 0.8 | 16 | 1 | 1 | 0 | 0.5 | 0 | 4 | 0 | 0 |
| M1403 | 0.6 | 0.8 | 16 | 1 | 1 | 0 | 0.5 | 0 | 5 | 0 | 0 |
| M1404 | 0.6 | 0.8 | 16 | 1 | 1 | 0 | 0.5 | 0 | 6 | 0 | 0 |
| M1405 | 0.6 | 0.9 | 12 | 1 | 1 | 0 | 0.5 | 0 | 2 | 0 | 0 |

TABLE 3-continued

Alloy chemistries in weight percent, balance Fe, for selected alloys evaluated using thermodynamic models which meet thermodynamic criteria

| Alloy | B | C | Cr | Mn | Mo | Nb | Si | Ti | V | W | Zr |
|---|---|---|---|---|---|---|---|---|---|---|---|
| M1406 | 0.6 | 0.9 | 12 | 1 | 1 | 0 | 0.5 | 0 | 3 | 0 | 0 |
| M1407 | 0.6 | 0.9 | 12 | 1 | 1 | 0 | 0.5 | 0 | 4 | 0 | 0 |
| M1408 | 0.6 | 0.9 | 14 | 1 | 1 | 0 | 0.5 | 0 | 3 | 0 | 0 |
| M1409 | 0.6 | 0.9 | 14 | 1 | 1 | 0 | 0.5 | 0 | 4 | 0 | 0 |
| M1410 | 0.6 | 0.9 | 16 | 1 | 1 | 0 | 0.5 | 0 | 5 | 0 | 0 |
| M1411 | 0.6 | 1 | 12 | 1 | 1 | 0 | 0.5 | 0 | 3 | 0 | 0 |
| M1412 | 0.6 | 1.1 | 12 | 1 | 1 | 0 | 0.5 | 0 | 3 | 0 | 0 |
| M1413 | 0.6 | 1.4 | 12 | 1 | 1 | 0 | 0.5 | 0 | 5 | 0 | 0 |
| M1414 | 0.6 | 1.4 | 12 | 1 | 1 | 0 | 0.5 | 0 | 6 | 0 | 0 |
| M1415 | 0.6 | 1.4 | 14 | 1 | 1 | 0 | 0.5 | 0 | 5 | 0 | 0 |
| M1416 | 0.6 | 1.4 | 14 | 1 | 1 | 0 | 0.5 | 0 | 6 | 0 | 0 |
| M1417 | 0.6 | 1.4 | 14 | 1 | 1 | 0 | 0.5 | 0 | 7 | 0 | 0 |
| M1418 | 0.6 | 1.4 | 14 | 1 | 1 | 0 | 0.5 | 0 | 8 | 0 | 0 |
| M1419 | 0.6 | 1.4 | 16 | 1 | 1 | 0 | 0.5 | 0 | 7 | 0 | 0 |
| M1420 | 0.6 | 1.4 | 16 | 1 | 1 | 0 | 0.5 | 0 | 8 | 0 | 0 |
| M1421 | 0.6 | 1.4 | 16 | 1 | 1 | 0 | 0.5 | 0 | 9 | 0 | 0 |
| M1422 | 0.6 | 1.5 | 12 | 1 | 1 | 0 | 0.5 | 0 | 5 | 0 | 0 |
| M1423 | 0.6 | 1.5 | 12 | 1 | 1 | 0 | 0.5 | 0 | 6 | 0 | 0 |
| M1424 | 0.6 | 1.5 | 14 | 1 | 1 | 0 | 0.5 | 0 | 6 | 0 | 0 |
| M1425 | 0.6 | 1.5 | 14 | 1 | 1 | 0 | 0.5 | 0 | 7 | 0 | 0 |
| M1426 | 0.6 | 1.5 | 16 | 1 | 1 | 0 | 0.5 | 0 | 8 | 0 | 0 |
| M1427 | 0.6 | 1.6 | 12 | 1 | 1 | 0 | 0.5 | 0 | 5 | 0 | 0 |
| M1428 | 0.6 | 1.6 | 12 | 1 | 1 | 0 | 0.5 | 0 | 6 | 0 | 0 |
| M1429 | 0.6 | 1.6 | 14 | 1 | 1 | 0 | 0.5 | 0 | 6 | 0 | 0 |
| M1430 | 0.6 | 1.6 | 16 | 1 | 1 | 0 | 0.5 | 0 | 8 | 0 | 0 |
| M1431 | 0.7 | 0.7 | 12 | 1 | 1 | 0 | 0.5 | 0 | 2 | 0 | 0 |
| M1432 | 0.7 | 0.7 | 12 | 1 | 1 | 0 | 0.5 | 0 | 3 | 0 | 0 |
| M1433 | 0.7 | 0.7 | 12 | 1 | 1 | 0 | 0.5 | 0 | 4 | 0 | 0 |
| M1434 | 0.7 | 0.7 | 12 | 1 | 1 | 0 | 0.5 | 0 | 5 | 0 | 0 |
| M1435 | 0.7 | 0.7 | 12 | 1 | 1 | 0 | 0.5 | 0 | 6 | 0 | 0 |
| M1436 | 0.7 | 0.7 | 12 | 1 | 1 | 0 | 0.5 | 0 | 7 | 0 | 0 |
| M1437 | 0.7 | 0.7 | 14 | 1 | 1 | 0 | 0.5 | 0 | 2 | 0 | 0 |
| M1438 | 0.7 | 0.7 | 14 | 1 | 1 | 0 | 0.5 | 0 | 3 | 0 | 0 |
| M1439 | 0.7 | 0.7 | 14 | 1 | 1 | 0 | 0.5 | 0 | 4 | 0 | 0 |
| M1440 | 0.7 | 0.7 | 14 | 1 | 1 | 0 | 0.5 | 0 | 5 | 0 | 0 |
| M1441 | 0.7 | 0.7 | 14 | 1 | 1 | 0 | 0.5 | 0 | 6 | 0 | 0 |
| M1442 | 0.7 | 0.7 | 14 | 1 | 1 | 0 | 0.5 | 0 | 7 | 0 | 0 |
| M1443 | 0.7 | 0.7 | 16 | 1 | 1 | 0 | 0.5 | 0 | 4 | 0 | 0 |
| M1444 | 0.7 | 0.7 | 16 | 1 | 1 | 0 | 0.5 | 0 | 5 | 0 | 0 |
| M1445 | 0.7 | 0.7 | 16 | 1 | 1 | 0 | 0.5 | 0 | 6 | 0 | 0 |
| M1446 | 0.7 | 0.7 | 16 | 1 | 1 | 0 | 0.5 | 0 | 7 | 0 | 0 |
| M1447 | 0.7 | 0.7 | 16 | 1 | 1 | 0 | 0.5 | 0 | 8 | 0 | 0 |
| M1448 | 0.7 | 0.8 | 12 | 1 | 1 | 0 | 0.5 | 0 | 2 | 0 | 0 |
| M1449 | 0.7 | 0.8 | 12 | 1 | 1 | 0 | 0.5 | 0 | 3 | 0 | 0 |
| M1450 | 0.7 | 0.8 | 12 | 1 | 1 | 0 | 0.5 | 0 | 4 | 0 | 0 |
| M1451 | 0.7 | 0.8 | 12 | 1 | 1 | 0 | 0.5 | 0 | 5 | 0 | 0 |
| M1452 | 0.7 | 0.8 | 12 | 1 | 1 | 0 | 0.5 | 0 | 6 | 0 | 0 |
| M1453 | 0.7 | 0.8 | 14 | 1 | 1 | 0 | 0.5 | 0 | 3 | 0 | 0 |
| M1454 | 0.7 | 0.8 | 14 | 1 | 1 | 0 | 0.5 | 0 | 4 | 0 | 0 |
| M1455 | 0.7 | 0.8 | 14 | 1 | 1 | 0 | 0.5 | 0 | 5 | 0 | 0 |
| M1456 | 0.7 | 0.8 | 14 | 1 | 1 | 0 | 0.5 | 0 | 6 | 0 | 0 |
| M1457 | 0.7 | 0.8 | 14 | 1 | 1 | 0 | 0.5 | 0 | 7 | 0 | 0 |
| M1458 | 0.7 | 0.8 | 16 | 1 | 1 | 0 | 0.5 | 0 | 5 | 0 | 0 |
| M1459 | 0.7 | 0.8 | 16 | 1 | 1 | 0 | 0.5 | 0 | 6 | 0 | 0 |
| M1460 | 0.7 | 0.8 | 16 | 1 | 1 | 0 | 0.5 | 0 | 7 | 0 | 0 |
| M1461 | 0.7 | 0.9 | 12 | 1 | 1 | 0 | 0.5 | 0 | 3 | 0 | 0 |
| M1462 | 0.7 | 0.9 | 12 | 1 | 1 | 0 | 0.5 | 0 | 4 | 0 | 0 |
| M1463 | 0.7 | 0.9 | 12 | 1 | 1 | 0 | 0.5 | 0 | 5 | 0 | 0 |
| M1464 | 0.7 | 0.9 | 14 | 1 | 1 | 0 | 0.5 | 0 | 3 | 0 | 0 |
| M1465 | 0.7 | 0.9 | 14 | 1 | 1 | 0 | 0.5 | 0 | 4 | 0 | 0 |
| M1466 | 0.7 | 0.9 | 14 | 1 | 1 | 0 | 0.5 | 0 | 5 | 0 | 0 |
| M1467 | 0.7 | 0.9 | 14 | 1 | 1 | 0 | 0.5 | 0 | 6 | 0 | 0 |
| M1468 | 0.7 | 0.9 | 16 | 1 | 1 | 0 | 0.5 | 0 | 5 | 0 | 0 |
| M1469 | 0.7 | 0.9 | 16 | 1 | 1 | 0 | 0.5 | 0 | 6 | 0 | 0 |
| M1470 | 0.7 | 0.9 | 16 | 1 | 1 | 0 | 0.5 | 0 | 7 | 0 | 0 |
| M1471 | 0.7 | 1 | 12 | 1 | 1 | 0 | 0.5 | 0 | 3 | 0 | 0 |
| M1472 | 0.7 | 1 | 12 | 1 | 1 | 0 | 0.5 | 0 | 4 | 0 | 0 |
| M1473 | 0.7 | 1 | 14 | 1 | 1 | 0 | 0.5 | 0 | 4 | 0 | 0 |
| M1474 | 0.7 | 1 | 14 | 1 | 1 | 0 | 0.5 | 0 | 5 | 0 | 0 |
| M1475 | 0.7 | 1 | 16 | 1 | 1 | 0 | 0.5 | 0 | 6 | 0 | 0 |
| M1476 | 0.7 | 1.1 | 12 | 1 | 1 | 0 | 0.5 | 0 | 4 | 0 | 0 |
| M1477 | 0.7 | 1.1 | 14 | 1 | 1 | 0 | 0.5 | 0 | 4 | 0 | 0 |
| M1478 | 0.7 | 1.2 | 14 | 1 | 1 | 0 | 0.5 | 0 | 9 | 0 | 0 |
| M1479 | 0.7 | 1.2 | 14 | 1 | 1 | 0 | 0.5 | 0 | 10 | 0 | 0 |
| M1480 | 0.7 | 1.2 | 16 | 1 | 1 | 0 | 0.5 | 0 | 7 | 0 | 0 |

TABLE 3-continued

Alloy chemistries in weight percent, balance Fe, for selected alloys evaluated using thermodynamic models which meet thermodynamic criteria

| Alloy | B | C | Cr | Mn | Mo | Nb | Si | Ti | V | W | Zr |
|---|---|---|---|---|---|---|---|---|---|---|---|
| M1481 | 0.7 | 1.2 | 16 | 1 | 1 | 0 | 0.5 | 0 | 8 | 0 | 0 |
| M1482 | 0.7 | 1.2 | 16 | 1 | 1 | 0 | 0.5 | 0 | 9 | 0 | 0 |
| M1483 | 0.7 | 1.2 | 16 | 1 | 1 | 0 | 0.5 | 0 | 10 | 0 | 0 |
| M1484 | 0.7 | 1.3 | 12 | 1 | 1 | 0 | 0.5 | 0 | 4 | 0 | 0 |
| M1485 | 0.7 | 1.3 | 12 | 1 | 1 | 0 | 0.5 | 0 | 5 | 0 | 0 |
| M1486 | 0.7 | 1.3 | 12 | 1 | 1 | 0 | 0.5 | 0 | 6 | 0 | 0 |
| M1487 | 0.7 | 1.3 | 12 | 1 | 1 | 0 | 0.5 | 0 | 7 | 0 | 0 |
| M1488 | 0.7 | 1.3 | 12 | 1 | 1 | 0 | 0.5 | 0 | 8 | 0 | 0 |
| M1489 | 0.7 | 1.3 | 12 | 1 | 1 | 0 | 0.5 | 0 | 9 | 0 | 0 |
| M1490 | 0.7 | 1.3 | 14 | 1 | 1 | 0 | 0.5 | 0 | 5 | 0 | 0 |
| M1491 | 0.7 | 1.3 | 14 | 1 | 1 | 0 | 0.5 | 0 | 6 | 0 | 0 |
| M1492 | 0.7 | 1.3 | 14 | 1 | 1 | 0 | 0.5 | 0 | 7 | 0 | 0 |
| M1493 | 0.7 | 1.3 | 14 | 1 | 1 | 0 | 0.5 | 0 | 8 | 0 | 0 |
| M1494 | 0.7 | 1.3 | 14 | 1 | 1 | 0 | 0.5 | 0 | 9 | 0 | 0 |
| M1495 | 0.7 | 1.3 | 14 | 1 | 1 | 0 | 0.5 | 0 | 10 | 0 | 0 |
| M1496 | 0.7 | 1.3 | 16 | 1 | 1 | 0 | 0.5 | 0 | 7 | 0 | 0 |
| M1497 | 0.7 | 1.3 | 16 | 1 | 1 | 0 | 0.5 | 0 | 8 | 0 | 0 |
| M1498 | 0.7 | 1.3 | 16 | 1 | 1 | 0 | 0.5 | 0 | 9 | 0 | 0 |
| M1499 | 0.7 | 1.3 | 16 | 1 | 1 | 0 | 0.5 | 0 | 10 | 0 | 0 |
| M1500 | 0.7 | 1.4 | 12 | 1 | 1 | 0 | 0.5 | 0 | 5 | 0 | 0 |
| M1501 | 0.7 | 1.4 | 12 | 1 | 1 | 0 | 0.5 | 0 | 6 | 0 | 0 |
| M1502 | 0.7 | 1.4 | 12 | 1 | 1 | 0 | 0.5 | 0 | 7 | 0 | 0 |
| M1503 | 0.7 | 1.4 | 12 | 1 | 1 | 0 | 0.5 | 0 | 8 | 0 | 0 |
| M1504 | 0.7 | 1.4 | 14 | 1 | 1 | 0 | 0.5 | 0 | 6 | 0 | 0 |
| M1505 | 0.7 | 1.4 | 14 | 1 | 1 | 0 | 0.5 | 0 | 7 | 0 | 0 |
| M1506 | 0.7 | 1.4 | 14 | 1 | 1 | 0 | 0.5 | 0 | 8 | 0 | 0 |
| M1507 | 0.7 | 1.4 | 14 | 1 | 1 | 0 | 0.5 | 0 | 9 | 0 | 0 |
| M1508 | 0.7 | 1.4 | 14 | 1 | 1 | 0 | 0.5 | 0 | 10 | 0 | 0 |
| M1509 | 0.7 | 1.4 | 16 | 1 | 1 | 0 | 0.5 | 0 | 7 | 0 | 0 |
| M1510 | 0.7 | 1.4 | 16 | 1 | 1 | 0 | 0.5 | 0 | 8 | 0 | 0 |
| M1511 | 0.7 | 1.4 | 16 | 1 | 1 | 0 | 0.5 | 0 | 9 | 0 | 0 |
| M1512 | 0.7 | 1.4 | 16 | 1 | 1 | 0 | 0.5 | 0 | 10 | 0 | 0 |
| M1513 | 0.7 | 1.5 | 12 | 1 | 1 | 0 | 0.5 | 0 | 5 | 0 | 0 |
| M1514 | 0.7 | 1.5 | 12 | 1 | 1 | 0 | 0.5 | 0 | 6 | 0 | 0 |
| M1515 | 0.7 | 1.5 | 12 | 1 | 1 | 0 | 0.5 | 0 | 7 | 0 | 0 |
| M1516 | 0.7 | 1.5 | 12 | 1 | 1 | 0 | 0.5 | 0 | 8 | 0 | 0 |
| M1517 | 0.7 | 1.5 | 14 | 1 | 1 | 0 | 0.5 | 0 | 6 | 0 | 0 |
| M1518 | 0.7 | 1.5 | 14 | 1 | 1 | 0 | 0.5 | 0 | 7 | 0 | 0 |
| M1519 | 0.7 | 1.5 | 14 | 1 | 1 | 0 | 0.5 | 0 | 8 | 0 | 0 |
| M1520 | 0.7 | 1.5 | 14 | 1 | 1 | 0 | 0.5 | 0 | 9 | 0 | 0 |
| M1521 | 0.7 | 1.5 | 16 | 1 | 1 | 0 | 0.5 | 0 | 8 | 0 | 0 |
| M1522 | 0.7 | 1.5 | 16 | 1 | 1 | 0 | 0.5 | 0 | 9 | 0 | 0 |
| M1523 | 0.7 | 1.5 | 16 | 1 | 1 | 0 | 0.5 | 0 | 10 | 0 | 0 |
| M1524 | 0.7 | 1.6 | 12 | 1 | 1 | 0 | 0.5 | 0 | 6 | 0 | 0 |
| M1525 | 0.7 | 1.6 | 12 | 1 | 1 | 0 | 0.5 | 0 | 7 | 0 | 0 |
| M1526 | 0.7 | 1.6 | 14 | 1 | 1 | 0 | 0.5 | 0 | 7 | 0 | 0 |
| M1527 | 0.7 | 1.6 | 14 | 1 | 1 | 0 | 0.5 | 0 | 8 | 0 | 0 |
| M1528 | 0.7 | 1.6 | 16 | 1 | 1 | 0 | 0.5 | 0 | 8 | 0 | 0 |
| M1529 | 0.7 | 1.6 | 16 | 1 | 1 | 0 | 0.5 | 0 | 9 | 0 | 0 |
| M1530 | 0.7 | 1.6 | 16 | 1 | 1 | 0 | 0.5 | 0 | 10 | 0 | 0 |
| M1531 | 0.7 | 1.7 | 12 | 1 | 1 | 0 | 0.5 | 0 | 6 | 0 | 0 |
| M1532 | 0.7 | 1.7 | 12 | 1 | 1 | 0 | 0.5 | 0 | 7 | 0 | 0 |
| M1533 | 0.7 | 1.7 | 14 | 1 | 1 | 0 | 0.5 | 0 | 7 | 0 | 0 |
| M1534 | 0.7 | 1.7 | 14 | 1 | 1 | 0 | 0.5 | 0 | 8 | 0 | 0 |
| M1535 | 0.7 | 1.7 | 16 | 1 | 1 | 0 | 0.5 | 0 | 9 | 0 | 0 |
| M1536 | 0.7 | 1.8 | 14 | 1 | 1 | 0 | 0.5 | 0 | 7 | 0 | 0 |
| M1537 | 0.7 | 1.8 | 16 | 1 | 1 | 0 | 0.5 | 0 | 9 | 0 | 0 |
| M1538 | 0.7 | 2 | 12 | 1 | 1 | 0 | 0.5 | 0 | 7 | 0 | 0 |
| M1539 | 0.7 | 2 | 12 | 1 | 1 | 0 | 0.5 | 0 | 9 | 0 | 0 |
| M1540 | 0.7 | 2 | 12 | 1 | 1 | 0 | 0.5 | 0 | 10 | 0 | 0 |
| M1541 | 0.7 | 2 | 14 | 1 | 1 | 0 | 0.5 | 0 | 10 | 0 | 0 |
| M1542 | 0.8 | 0.7 | 12 | 1 | 1 | 0 | 0.5 | 0 | 2 | 0 | 0 |
| M1543 | 0.8 | 0.7 | 12 | 1 | 1 | 0 | 0.5 | 0 | 3 | 0 | 0 |
| M1544 | 0.8 | 0.7 | 12 | 1 | 1 | 0 | 0.5 | 0 | 4 | 0 | 0 |
| M1545 | 0.8 | 0.7 | 12 | 1 | 1 | 0 | 0.5 | 0 | 5 | 0 | 0 |
| M1546 | 0.8 | 0.7 | 12 | 1 | 1 | 0 | 0.5 | 0 | 6 | 0 | 0 |
| M1547 | 0.8 | 0.7 | 12 | 1 | 1 | 0 | 0.5 | 0 | 7 | 0 | 0 |
| M1548 | 0.8 | 0.7 | 12 | 1 | 1 | 0 | 0.5 | 0 | 8 | 0 | 0 |
| M1549 | 0.8 | 0.7 | 14 | 1 | 1 | 0 | 0.5 | 0 | 3 | 0 | 0 |
| M1550 | 0.8 | 0.7 | 14 | 1 | 1 | 0 | 0.5 | 0 | 4 | 0 | 0 |
| M1551 | 0.8 | 0.7 | 14 | 1 | 1 | 0 | 0.5 | 0 | 5 | 0 | 0 |
| M1552 | 0.8 | 0.7 | 14 | 1 | 1 | 0 | 0.5 | 0 | 6 | 0 | 0 |
| M1553 | 0.8 | 0.7 | 14 | 1 | 1 | 0 | 0.5 | 0 | 7 | 0 | 0 |
| M1554 | 0.8 | 0.7 | 14 | 1 | 1 | 0 | 0.5 | 0 | 8 | 0 | 0 |
| M1555 | 0.8 | 0.7 | 16 | 1 | 1 | 0 | 0.5 | 0 | 5 | 0 | 0 |

TABLE 3-continued

Alloy chemistries in weight percent, balance Fe, for selected alloys evaluated using thermodynamic models which meet thermodynamic criteria

| Alloy | B | C | Cr | Mn | Mo | Nb | Si | Ti | V | W | Zr |
|---|---|---|---|---|---|---|---|---|---|---|---|
| M1556 | 0.8 | 0.7 | 16 | 1 | 1 | 0 | 0.5 | 0 | 6 | 0 | 0 |
| M1557 | 0.8 | 0.7 | 16 | 1 | 1 | 0 | 0.5 | 0 | 7 | 0 | 0 |
| M1558 | 0.8 | 0.7 | 16 | 1 | 1 | 0 | 0.5 | 0 | 8 | 0 | 0 |
| M1559 | 0.8 | 0.7 | 16 | 1 | 1 | 0 | 0.5 | 0 | 9 | 0 | 0 |
| M1560 | 0.8 | 0.8 | 12 | 1 | 1 | 0 | 0.5 | 0 | 3 | 0 | 0 |
| M1561 | 0.8 | 0.8 | 12 | 1 | 1 | 0 | 0.5 | 0 | 4 | 0 | 0 |
| M1562 | 0.8 | 0.8 | 12 | 1 | 1 | 0 | 0.5 | 0 | 5 | 0 | 0 |
| M1563 | 0.8 | 0.8 | 12 | 1 | 1 | 0 | 0.5 | 0 | 6 | 0 | 0 |
| M1564 | 0.8 | 0.8 | 12 | 1 | 1 | 0 | 0.5 | 0 | 7 | 0 | 0 |
| M1565 | 0.8 | 0.8 | 14 | 1 | 1 | 0 | 0.5 | 0 | 3 | 0 | 0 |
| M1566 | 0.8 | 0.8 | 14 | 1 | 1 | 0 | 0.5 | 0 | 4 | 0 | 0 |
| M1567 | 0.8 | 0.8 | 14 | 1 | 1 | 0 | 0.5 | 0 | 5 | 0 | 0 |
| M1568 | 0.8 | 0.8 | 14 | 1 | 1 | 0 | 0.5 | 0 | 6 | 0 | 0 |
| M1569 | 0.8 | 0.8 | 14 | 1 | 1 | 0 | 0.5 | 0 | 7 | 0 | 0 |
| M1570 | 0.8 | 0.8 | 14 | 1 | 1 | 0 | 0.5 | 0 | 8 | 0 | 0 |
| M1571 | 0.8 | 0.8 | 16 | 1 | 1 | 0 | 0.5 | 0 | 5 | 0 | 0 |
| M1572 | 0.8 | 0.8 | 16 | 1 | 1 | 0 | 0.5 | 0 | 6 | 0 | 0 |
| M1573 | 0.8 | 0.8 | 16 | 1 | 1 | 0 | 0.5 | 0 | 7 | 0 | 0 |
| M1574 | 0.8 | 0.8 | 16 | 1 | 1 | 0 | 0.5 | 0 | 8 | 0 | 0 |
| M1575 | 0.8 | 0.8 | 16 | 1 | 1 | 0 | 0.5 | 0 | 9 | 0 | 0 |
| M1576 | 0.8 | 0.9 | 12 | 1 | 1 | 0 | 0.5 | 0 | 3 | 0 | 0 |
| M1577 | 0.8 | 0.9 | 12 | 1 | 1 | 0 | 0.5 | 0 | 4 | 0 | 0 |
| M1578 | 0.8 | 0.9 | 12 | 1 | 1 | 0 | 0.5 | 0 | 5 | 0 | 0 |
| M1579 | 0.8 | 0.9 | 12 | 1 | 1 | 0 | 0.5 | 0 | 6 | 0 | 0 |
| M1580 | 0.8 | 0.9 | 14 | 1 | 1 | 0 | 0.5 | 0 | 4 | 0 | 0 |
| M1581 | 0.8 | 0.9 | 14 | 1 | 1 | 0 | 0.5 | 0 | 5 | 0 | 0 |
| M1582 | 0.8 | 0.9 | 14 | 1 | 1 | 0 | 0.5 | 0 | 6 | 0 | 0 |
| M1583 | 0.8 | 0.9 | 14 | 1 | 1 | 0 | 0.5 | 0 | 7 | 0 | 0 |
| M1584 | 0.8 | 0.9 | 16 | 1 | 1 | 0 | 0.5 | 0 | 6 | 0 | 0 |
| M1585 | 0.8 | 0.9 | 16 | 1 | 1 | 0 | 0.5 | 0 | 7 | 0 | 0 |
| M1586 | 0.8 | 0.9 | 16 | 1 | 1 | 0 | 0.5 | 0 | 8 | 0 | 0 |
| M1587 | 0.8 | 1 | 12 | 1 | 1 | 0 | 0.5 | 0 | 3 | 0 | 0 |
| M1588 | 0.8 | 1 | 12 | 1 | 1 | 0 | 0.5 | 0 | 4 | 0 | 0 |
| M1589 | 0.8 | 1 | 12 | 1 | 1 | 0 | 0.5 | 0 | 5 | 0 | 0 |
| M1590 | 0.8 | 1 | 14 | 1 | 1 | 0 | 0.5 | 0 | 4 | 0 | 0 |
| M1591 | 0.8 | 1 | 14 | 1 | 1 | 0 | 0.5 | 0 | 5 | 0 | 0 |
| M1592 | 0.8 | 1 | 14 | 1 | 1 | 0 | 0.5 | 0 | 6 | 0 | 0 |
| M1593 | 0.8 | 1 | 16 | 1 | 1 | 0 | 0.5 | 0 | 6 | 0 | 0 |
| M1594 | 0.8 | 1 | 16 | 1 | 1 | 0 | 0.5 | 0 | 7 | 0 | 0 |
| M1595 | 0.8 | 1.1 | 12 | 1 | 1 | 0 | 0.5 | 0 | 4 | 0 | 0 |
| M1596 | 0.8 | 1.1 | 12 | 1 | 1 | 0 | 0.5 | 0 | 5 | 0 | 0 |
| M1597 | 0.8 | 1.1 | 12 | 1 | 1 | 0 | 0.5 | 0 | 8 | 0 | 0 |
| M1598 | 0.8 | 1.1 | 12 | 1 | 1 | 0 | 0.5 | 0 | 9 | 0 | 0 |
| M1599 | 0.8 | 1.1 | 12 | 1 | 1 | 0 | 0.5 | 0 | 10 | 0 | 0 |
| M1600 | 0.8 | 1.1 | 14 | 1 | 1 | 0 | 0.5 | 0 | 7 | 0 | 0 |
| M1601 | 0.8 | 1.1 | 14 | 1 | 1 | 0 | 0.5 | 0 | 8 | 0 | 0 |
| M1602 | 0.8 | 1.1 | 14 | 1 | 1 | 0 | 0.5 | 0 | 9 | 0 | 0 |
| M1603 | 0.8 | 1.1 | 14 | 1 | 1 | 0 | 0.5 | 0 | 10 | 0 | 0 |
| M1604 | 0.8 | 1.1 | 16 | 1 | 1 | 0 | 0.5 | 0 | 8 | 0 | 0 |
| M1605 | 0.8 | 1.1 | 16 | 1 | 1 | 0 | 0.5 | 0 | 9 | 0 | 0 |
| M1606 | 0.8 | 1.1 | 16 | 1 | 1 | 0 | 0.5 | 0 | 10 | 0 | 0 |
| M1607 | 0.8 | 1.2 | 12 | 1 | 1 | 0 | 0.5 | 0 | 5 | 0 | 0 |
| M1608 | 0.8 | 1.2 | 12 | 1 | 1 | 0 | 0.5 | 0 | 6 | 0 | 0 |
| M1609 | 0.8 | 1.2 | 12 | 1 | 1 | 0 | 0.5 | 0 | 7 | 0 | 0 |
| M1610 | 0.8 | 1.2 | 12 | 1 | 1 | 0 | 0.5 | 0 | 8 | 0 | 0 |
| M1611 | 0.8 | 1.2 | 12 | 1 | 1 | 0 | 0.5 | 0 | 9 | 0 | 0 |
| M1612 | 0.8 | 1.2 | 12 | 1 | 1 | 0 | 0.5 | 0 | 10 | 0 | 0 |
| M1613 | 0.8 | 1.2 | 14 | 1 | 1 | 0 | 0.5 | 0 | 6 | 0 | 0 |
| M1614 | 0.8 | 1.2 | 14 | 1 | 1 | 0 | 0.5 | 0 | 7 | 0 | 0 |
| M1615 | 0.8 | 1.2 | 14 | 1 | 1 | 0 | 0.5 | 0 | 8 | 0 | 0 |
| M1616 | 0.8 | 1.2 | 14 | 1 | 1 | 0 | 0.5 | 0 | 9 | 0 | 0 |
| M1617 | 0.8 | 1.2 | 14 | 1 | 1 | 0 | 0.5 | 0 | 10 | 0 | 0 |
| M1618 | 0.8 | 1.2 | 16 | 1 | 1 | 0 | 0.5 | 0 | 7 | 0 | 0 |
| M1619 | 0.8 | 1.2 | 16 | 1 | 1 | 0 | 0.5 | 0 | 8 | 0 | 0 |
| M1620 | 0.8 | 1.2 | 16 | 1 | 1 | 0 | 0.5 | 0 | 9 | 0 | 0 |
| M1621 | 0.8 | 1.2 | 16 | 1 | 1 | 0 | 0.5 | 0 | 10 | 0 | 0 |
| M1622 | 0.8 | 1.3 | 12 | 1 | 1 | 0 | 0.5 | 0 | 5 | 0 | 0 |
| M1623 | 0.8 | 1.3 | 12 | 1 | 1 | 0 | 0.5 | 0 | 6 | 0 | 0 |
| M1624 | 0.8 | 1.3 | 12 | 1 | 1 | 0 | 0.5 | 0 | 7 | 0 | 0 |
| M1625 | 0.8 | 1.3 | 12 | 1 | 1 | 0 | 0.5 | 0 | 8 | 0 | 0 |
| M1626 | 0.8 | 1.3 | 12 | 1 | 1 | 0 | 0.5 | 0 | 9 | 0 | 0 |
| M1627 | 0.8 | 1.3 | 12 | 1 | 1 | 0 | 0.5 | 0 | 10 | 0 | 0 |
| M1628 | 0.8 | 1.3 | 14 | 1 | 1 | 0 | 0.5 | 0 | 5 | 0 | 0 |
| M1629 | 0.8 | 1.3 | 14 | 1 | 1 | 0 | 0.5 | 0 | 6 | 0 | 0 |
| M1630 | 0.8 | 1.3 | 14 | 1 | 1 | 0 | 0.5 | 0 | 7 | 0 | 0 |

TABLE 3-continued

Alloy chemistries in weight percent, balance Fe, for selected alloys evaluated using thermodynamic models which meet thermodynamic criteria

| Alloy | B | C | Cr | Mn | Mo | Nb | Si | Ti | V | W | Zr |
|---|---|---|---|---|---|---|---|---|---|---|---|
| M1631 | 0.8 | 1.3 | 14 | 1 | 1 | 0 | 0.5 | 0 | 8 | 0 | 0 |
| M1632 | 0.8 | 1.3 | 14 | 1 | 1 | 0 | 0.5 | 0 | 9 | 0 | 0 |
| M1633 | 0.8 | 1.3 | 14 | 1 | 1 | 0 | 0.5 | 0 | 10 | 0 | 0 |
| M1634 | 0.8 | 1.3 | 16 | 1 | 1 | 0 | 0.5 | 0 | 7 | 0 | 0 |
| M1635 | 1.1 | 0.65 | 3.5 | 0 | 1 | 2.5 | 0.5 | 0.5 | 0.5 | 0 | 0 |
| M1636 | 1.1 | 0.65 | 4 | 0 | 1 | 2.5 | 0.5 | 0.5 | 0.5 | 0 | 0 |
| M1637 | 1.1 | 0.65 | 4 | 0 | 1 | 2.5 | 0.5 | 1 | 0.5 | 0 | 0 |
| M1638 | 1.1 | 0.65 | 4.5 | 0 | 1 | 2.5 | 0.5 | 0.5 | 0.5 | 0 | 0 |
| M1639 | 1.1 | 0.65 | 4.5 | 0 | 1 | 2.5 | 0.5 | 1 | 0.5 | 0 | 0 |
| M1640 | 1.1 | 0.65 | 5 | 0 | 1 | 2.5 | 0.5 | 1 | 0.5 | 0 | 0 |
| M1641 | 0.8 | 1.3 | 16 | 1 | 1 | 0 | 0.5 | 0 | 8 | 0 | 0 |
| M1642 | 0.8 | 1.3 | 16 | 1 | 1 | 0 | 0.5 | 0 | 9 | 0 | 0 |
| M1643 | 0.8 | 1.3 | 16 | 1 | 1 | 0 | 0.5 | 0 | 10 | 0 | 0 |
| M1644 | 0.8 | 1.4 | 12 | 1 | 1 | 0 | 0.5 | 0 | 5 | 0 | 0 |
| M1645 | 0.8 | 1.4 | 12 | 1 | 1 | 0 | 0.5 | 0 | 6 | 0 | 0 |
| M1646 | 0.8 | 1.4 | 12 | 1 | 1 | 0 | 0.5 | 0 | 7 | 0 | 0 |
| M1647 | 0.8 | 1.4 | 12 | 1 | 1 | 0 | 0.5 | 0 | 8 | 0 | 0 |
| M1648 | 0.8 | 1.4 | 12 | 1 | 1 | 0 | 0.5 | 0 | 9 | 0 | 0 |
| M1649 | 0.8 | 1.4 | 12 | 1 | 1 | 0 | 0.5 | 0 | 10 | 0 | 0 |
| M1650 | 0.8 | 1.4 | 14 | 1 | 1 | 0 | 0.5 | 0 | 6 | 0 | 0 |
| M1651 | 0.8 | 1.4 | 14 | 1 | 1 | 0 | 0.5 | 0 | 7 | 0 | 0 |
| M1652 | 0.8 | 1.4 | 14 | 1 | 1 | 0 | 0.5 | 0 | 8 | 0 | 0 |
| M1653 | 0.8 | 1.4 | 14 | 1 | 1 | 0 | 0.5 | 0 | 9 | 0 | 0 |
| M1654 | 0.8 | 1.4 | 14 | 1 | 1 | 0 | 0.5 | 0 | 10 | 0 | 0 |
| M1655 | 0.8 | 1.4 | 16 | 1 | 1 | 0 | 0.5 | 0 | 8 | 0 | 0 |
| M1656 | 0.8 | 1.4 | 16 | 1 | 1 | 0 | 0.5 | 0 | 9 | 0 | 0 |
| M1657 | 0.8 | 1.4 | 16 | 1 | 1 | 0 | 0.5 | 0 | 10 | 0 | 0 |
| M1658 | 0.8 | 1.5 | 12 | 1 | 1 | 0 | 0.5 | 0 | 6 | 0 | 0 |
| M1659 | 0.8 | 1.5 | 12 | 1 | 1 | 0 | 0.5 | 0 | 7 | 0 | 0 |
| M1660 | 0.8 | 1.5 | 12 | 1 | 1 | 0 | 0.5 | 0 | 8 | 0 | 0 |
| M1661 | 0.8 | 1.5 | 12 | 1 | 1 | 0 | 0.5 | 0 | 9 | 0 | 0 |
| M1662 | 0.8 | 1.5 | 14 | 1 | 1 | 0 | 0.5 | 0 | 6 | 0 | 0 |
| M1663 | 0.8 | 1.5 | 14 | 1 | 1 | 0 | 0.5 | 0 | 7 | 0 | 0 |
| M1664 | 0.8 | 1.5 | 14 | 1 | 1 | 0 | 0.5 | 0 | 8 | 0 | 0 |
| M1665 | 0.8 | 1.5 | 14 | 1 | 1 | 0 | 0.5 | 0 | 9 | 0 | 0 |
| M1666 | 0.8 | 1.5 | 14 | 1 | 1 | 0 | 0.5 | 0 | 10 | 0 | 0 |
| M1667 | 0.8 | 1.5 | 16 | 1 | 1 | 0 | 0.5 | 0 | 8 | 0 | 0 |
| M1668 | 0.8 | 1.5 | 16 | 1 | 1 | 0 | 0.5 | 0 | 9 | 0 | 0 |
| M1669 | 0.8 | 1.5 | 16 | 1 | 1 | 0 | 0.5 | 0 | 10 | 0 | 0 |
| M1670 | 0.8 | 1.6 | 12 | 1 | 1 | 0 | 0.5 | 0 | 6 | 0 | 0 |
| M1671 | 0.8 | 1.6 | 12 | 1 | 1 | 0 | 0.5 | 0 | 7 | 0 | 0 |
| M1672 | 0.8 | 1.6 | 12 | 1 | 1 | 0 | 0.5 | 0 | 8 | 0 | 0 |
| M1673 | 0.8 | 1.6 | 12 | 1 | 1 | 0 | 0.5 | 0 | 9 | 0 | 0 |
| M1674 | 0.8 | 1.6 | 14 | 1 | 1 | 0 | 0.5 | 0 | 7 | 0 | 0 |
| M1675 | 0.8 | 1.6 | 14 | 1 | 1 | 0 | 0.5 | 0 | 8 | 0 | 0 |
| M1676 | 0.8 | 1.6 | 14 | 1 | 1 | 0 | 0.5 | 0 | 9 | 0 | 0 |
| M1677 | 0.8 | 1.6 | 14 | 1 | 1 | 0 | 0.5 | 0 | 10 | 0 | 0 |
| M1678 | 0.8 | 1.6 | 16 | 1 | 1 | 0 | 0.5 | 0 | 9 | 0 | 0 |
| M1679 | 0.8 | 1.6 | 16 | 1 | 1 | 0 | 0.5 | 0 | 10 | 0 | 0 |
| M1680 | 0.8 | 1.7 | 12 | 1 | 1 | 0 | 0.5 | 0 | 6 | 0 | 0 |
| M1681 | 0.8 | 1.7 | 12 | 1 | 1 | 0 | 0.5 | 0 | 7 | 0 | 0 |
| M1682 | 0.8 | 1.7 | 12 | 1 | 1 | 0 | 0.5 | 0 | 8 | 0 | 0 |
| M1683 | 0.8 | 1.7 | 14 | 1 | 1 | 0 | 0.5 | 0 | 7 | 0 | 0 |
| M1684 | 0.8 | 1.7 | 14 | 1 | 1 | 0 | 0.5 | 0 | 8 | 0 | 0 |
| M1685 | 0.8 | 1.7 | 14 | 1 | 1 | 0 | 0.5 | 0 | 9 | 0 | 0 |
| M1686 | 0.8 | 1.7 | 14 | 1 | 1 | 0 | 0.5 | 0 | 10 | 0 | 0 |
| M1687 | 0.8 | 1.7 | 16 | 1 | 1 | 0 | 0.5 | 0 | 9 | 0 | 0 |
| M1688 | 0.8 | 1.7 | 16 | 1 | 1 | 0 | 0.5 | 0 | 10 | 0 | 0 |
| M1689 | 0.8 | 1.8 | 12 | 1 | 1 | 0 | 0.5 | 0 | 7 | 0 | 0 |
| M1690 | 0.8 | 1.8 | 12 | 1 | 1 | 0 | 0.5 | 0 | 8 | 0 | 0 |
| M1691 | 0.8 | 1.8 | 12 | 1 | 1 | 0 | 0.5 | 0 | 9 | 0 | 0 |
| M1692 | 0.8 | 1.8 | 12 | 1 | 1 | 0 | 0.5 | 0 | 10 | 0 | 0 |
| M1693 | 0.8 | 1.8 | 14 | 1 | 1 | 0 | 0.5 | 0 | 8 | 0 | 0 |
| M1694 | 0.8 | 1.8 | 14 | 1 | 1 | 0 | 0.5 | 0 | 9 | 0 | 0 |
| M1695 | 0.8 | 1.8 | 14 | 1 | 1 | 0 | 0.5 | 0 | 10 | 0 | 0 |
| M1696 | 0.8 | 1.8 | 16 | 1 | 1 | 0 | 0.5 | 0 | 10 | 0 | 0 |
| M1697 | 0.8 | 1.9 | 12 | 1 | 1 | 0 | 0.5 | 0 | 7 | 0 | 0 |
| M1698 | 0.8 | 1.9 | 12 | 1 | 1 | 0 | 0.5 | 0 | 8 | 0 | 0 |
| M1699 | 0.8 | 1.9 | 12 | 1 | 1 | 0 | 0.5 | 0 | 9 | 0 | 0 |
| M1700 | 0.8 | 1.9 | 12 | 1 | 1 | 0 | 0.5 | 0 | 10 | 0 | 0 |
| M1701 | 0.8 | 1.9 | 14 | 1 | 1 | 0 | 0.5 | 0 | 8 | 0 | 0 |
| M1702 | 0.8 | 1.9 | 14 | 1 | 1 | 0 | 0.5 | 0 | 9 | 0 | 0 |
| M1703 | 0.8 | 1.9 | 14 | 1 | 1 | 0 | 0.5 | 0 | 10 | 0 | 0 |
| M1704 | 0.8 | 1.9 | 16 | 1 | 1 | 0 | 0.5 | 0 | 10 | 0 | 0 |
| M1705 | 0.8 | 2 | 12 | 1 | 1 | 0 | 0.5 | 0 | 8 | 0 | 0 |

TABLE 3-continued

Alloy chemistries in weight percent, balance Fe, for selected alloys evaluated using thermodynamic models which meet thermodynamic criteria

| Alloy | B | C | Cr | Mn | Mo | Nb | Si | Ti | V | W | Zr |
|---|---|---|---|---|---|---|---|---|---|---|---|
| M1706 | 0.8 | 2 | 14 | 1 | 1 | 0 | 0.5 | 0 | 9 | 0 | 0 |
| M1707 | 0.9 | 0.7 | 12 | 1 | 1 | 0 | 0.5 | 0 | 3 | 0 | 0 |
| M1708 | 0.9 | 0.7 | 12 | 1 | 1 | 0 | 0.5 | 0 | 4 | 0 | 0 |
| M1709 | 0.9 | 0.7 | 12 | 1 | 1 | 0 | 0.5 | 0 | 5 | 0 | 0 |
| M1710 | 0.9 | 0.7 | 12 | 1 | 1 | 0 | 0.5 | 0 | 6 | 0 | 0 |
| M1711 | 0.9 | 0.7 | 12 | 1 | 1 | 0 | 0.5 | 0 | 7 | 0 | 0 |
| M1712 | 0.9 | 0.7 | 12 | 1 | 1 | 0 | 0.5 | 0 | 8 | 0 | 0 |
| M1713 | 0.9 | 0.7 | 14 | 1 | 1 | 0 | 0.5 | 0 | 3 | 0 | 0 |
| M1714 | 0.9 | 0.7 | 14 | 1 | 1 | 0 | 0.5 | 0 | 4 | 0 | 0 |
| M1715 | 0.9 | 0.7 | 14 | 1 | 1 | 0 | 0.5 | 0 | 5 | 0 | 0 |
| M1716 | 0.9 | 0.7 | 14 | 1 | 1 | 0 | 0.5 | 0 | 6 | 0 | 0 |
| M1717 | 0.9 | 0.7 | 14 | 1 | 1 | 0 | 0.5 | 0 | 7 | 0 | 0 |
| M1718 | 0.9 | 0.7 | 14 | 1 | 1 | 0 | 0.5 | 0 | 8 | 0 | 0 |
| M1719 | 0.9 | 0.7 | 14 | 1 | 1 | 0 | 0.5 | 0 | 9 | 0 | 0 |
| M1720 | 0.9 | 0.7 | 16 | 1 | 1 | 0 | 0.5 | 0 | 5 | 0 | 0 |
| M1721 | 0.9 | 0.7 | 16 | 1 | 1 | 0 | 0.5 | 0 | 6 | 0 | 0 |
| M1722 | 0.9 | 0.7 | 16 | 1 | 1 | 0 | 0.5 | 0 | 7 | 0 | 0 |
| M1723 | 0.9 | 0.7 | 16 | 1 | 1 | 0 | 0.5 | 0 | 8 | 0 | 0 |
| M1724 | 0.9 | 0.7 | 16 | 1 | 1 | 0 | 0.5 | 0 | 9 | 0 | 0 |
| M1725 | 0.9 | 0.7 | 16 | 1 | 1 | 0 | 0.5 | 0 | 10 | 0 | 0 |
| M1726 | 0.9 | 0.8 | 12 | 1 | 1 | 0 | 0.5 | 0 | 3 | 0 | 0 |
| M1727 | 0.9 | 0.8 | 12 | 1 | 1 | 0 | 0.5 | 0 | 4 | 0 | 0 |
| M1728 | 0.9 | 0.8 | 12 | 1 | 1 | 0 | 0.5 | 0 | 5 | 0 | 0 |
| M1729 | 0.9 | 0.8 | 12 | 1 | 1 | 0 | 0.5 | 0 | 6 | 0 | 0 |
| M1730 | 0.9 | 0.8 | 12 | 1 | 1 | 0 | 0.5 | 0 | 7 | 0 | 0 |
| M1731 | 0.9 | 0.8 | 12 | 1 | 1 | 0 | 0.5 | 0 | 8 | 0 | 0 |
| M1732 | 0.9 | 0.8 | 14 | 1 | 1 | 0 | 0.5 | 0 | 4 | 0 | 0 |
| M1733 | 0.9 | 0.8 | 14 | 1 | 1 | 0 | 0.5 | 0 | 5 | 0 | 0 |
| M1734 | 0.9 | 0.8 | 14 | 1 | 1 | 0 | 0.5 | 0 | 6 | 0 | 0 |
| M1735 | 0.9 | 0.8 | 14 | 1 | 1 | 0 | 0.5 | 0 | 7 | 0 | 0 |
| M1736 | 0.9 | 0.8 | 14 | 1 | 1 | 0 | 0.5 | 0 | 8 | 0 | 0 |
| M1737 | 0.9 | 0.8 | 14 | 1 | 1 | 0 | 0.5 | 0 | 9 | 0 | 0 |
| M1738 | 0.9 | 0.8 | 16 | 1 | 1 | 0 | 0.5 | 0 | 5 | 0 | 0 |
| M1739 | 0.9 | 0.8 | 16 | 1 | 1 | 0 | 0.5 | 0 | 6 | 0 | 0 |
| M1740 | 0.9 | 0.8 | 16 | 1 | 1 | 0 | 0.5 | 0 | 7 | 0 | 0 |
| M1741 | 0.9 | 0.8 | 16 | 1 | 1 | 0 | 0.5 | 0 | 8 | 0 | 0 |
| M1742 | 0.9 | 0.8 | 16 | 1 | 1 | 0 | 0.5 | 0 | 9 | 0 | 0 |
| M1743 | 0.9 | 0.8 | 16 | 1 | 1 | 0 | 0.5 | 0 | 10 | 0 | 0 |
| M1744 | 0.9 | 0.9 | 12 | 1 | 1 | 0 | 0.5 | 0 | 3 | 0 | 0 |
| M1745 | 0.9 | 0.9 | 12 | 1 | 1 | 0 | 0.5 | 0 | 4 | 0 | 0 |
| M1746 | 0.9 | 0.9 | 12 | 1 | 1 | 0 | 0.5 | 0 | 5 | 0 | 0 |
| M1747 | 0.9 | 0.9 | 12 | 1 | 1 | 0 | 0.5 | 0 | 6 | 0 | 0 |
| M1748 | 0.9 | 0.9 | 12 | 1 | 1 | 0 | 0.5 | 0 | 7 | 0 | 0 |
| M1749 | 0.9 | 0.9 | 14 | 1 | 1 | 0 | 0.5 | 0 | 4 | 0 | 0 |
| M1750 | 0.9 | 0.9 | 14 | 1 | 1 | 0 | 0.5 | 0 | 5 | 0 | 0 |
| M1751 | 0.9 | 0.9 | 14 | 1 | 1 | 0 | 0.5 | 0 | 6 | 0 | 0 |
| M1752 | 0.9 | 0.9 | 14 | 1 | 1 | 0 | 0.5 | 0 | 7 | 0 | 0 |
| M1753 | 0.9 | 0.9 | 14 | 1 | 1 | 0 | 0.5 | 0 | 8 | 0 | 0 |
| M1754 | 0.9 | 0.9 | 16 | 1 | 1 | 0 | 0.5 | 0 | 6 | 0 | 0 |
| M1755 | 0.9 | 0.9 | 16 | 1 | 1 | 0 | 0.5 | 0 | 7 | 0 | 0 |
| M1756 | 0.9 | 0.9 | 16 | 1 | 1 | 0 | 0.5 | 0 | 8 | 0 | 0 |
| M1757 | 0.9 | 0.9 | 16 | 1 | 1 | 0 | 0.5 | 0 | 10 | 0 | 0 |
| M1758 | 0.9 | 1 | 12 | 1 | 1 | 0 | 0.5 | 0 | 8 | 0 | 0 |
| M1759 | 0.9 | 1 | 12 | 1 | 1 | 0 | 0.5 | 0 | 9 | 0 | 0 |
| M1760 | 0.9 | 1 | 12 | 1 | 1 | 0 | 0.5 | 0 | 10 | 0 | 0 |
| M1761 | 0.9 | 1 | 14 | 1 | 1 | 0 | 0.5 | 0 | 9 | 0 | 0 |
| M1762 | 0.9 | 1 | 14 | 1 | 1 | 0 | 0.5 | 0 | 10 | 0 | 0 |
| M1763 | 0.9 | 1 | 16 | 1 | 1 | 0 | 0.5 | 0 | 10 | 0 | 0 |
| M1764 | 0.9 | 1.1 | 12 | 1 | 1 | 0 | 0.5 | 0 | 7 | 0 | 0 |
| M1765 | 0.9 | 1.1 | 12 | 1 | 1 | 0 | 0.5 | 0 | 8 | 0 | 0 |
| M1766 | 0.9 | 1.1 | 12 | 1 | 1 | 0 | 0.5 | 0 | 9 | 0 | 0 |
| M1767 | 0.9 | 1.1 | 12 | 1 | 1 | 0 | 0.5 | 0 | 10 | 0 | 0 |
| M1768 | 0.9 | 1.1 | 14 | 1 | 1 | 0 | 0.5 | 0 | 8 | 0 | 0 |
| M1769 | 0.9 | 1.1 | 14 | 1 | 1 | 0 | 0.5 | 0 | 9 | 0 | 0 |
| M1770 | 0.9 | 1.1 | 14 | 1 | 1 | 0 | 0.5 | 0 | 10 | 0 | 0 |
| M1771 | 0.9 | 1.1 | 16 | 1 | 1 | 0 | 0.5 | 0 | 9 | 0 | 0 |
| M1772 | 0.9 | 1.1 | 16 | 1 | 1 | 0 | 0.5 | 0 | 10 | 0 | 0 |
| M1773 | 0.9 | 1.2 | 12 | 1 | 1 | 0 | 0.5 | 0 | 6 | 0 | 0 |
| M1774 | 0.9 | 1.2 | 12 | 1 | 1 | 0 | 0.5 | 0 | 7 | 0 | 0 |
| M1775 | 0.9 | 1.2 | 12 | 1 | 1 | 0 | 0.5 | 0 | 8 | 0 | 0 |
| M1776 | 0.9 | 1.2 | 12 | 1 | 1 | 0 | 0.5 | 0 | 9 | 0 | 0 |
| M1777 | 0.9 | 1.2 | 12 | 1 | 1 | 0 | 0.5 | 0 | 10 | 0 | 0 |
| M1778 | 0.9 | 1.2 | 14 | 1 | 1 | 0 | 0.5 | 0 | 7 | 0 | 0 |
| M1779 | 0.9 | 1.2 | 14 | 1 | 1 | 0 | 0.5 | 0 | 8 | 0 | 0 |
| M1780 | 0.9 | 1.2 | 14 | 1 | 1 | 0 | 0.5 | 0 | 9 | 0 | 0 |

TABLE 3-continued

Alloy chemistries in weight percent, balance Fe, for selected alloys evaluated using thermodynamic models which meet thermodynamic criteria

| Alloy | B | C | Cr | Mn | Mo | Nb | Si | Ti | V | W | Zr |
|---|---|---|---|---|---|---|---|---|---|---|---|
| M1781 | 0.9 | 1.2 | 14 | 1 | 1 | 0 | 0.5 | 0 | 10 | 0 | 0 |
| M1782 | 0.9 | 1.2 | 16 | 1 | 1 | 0 | 0.5 | 0 | 8 | 0 | 0 |
| M1783 | 0.9 | 1.2 | 16 | 1 | 1 | 0 | 0.5 | 0 | 9 | 0 | 0 |
| M1784 | 0.9 | 1.2 | 16 | 1 | 1 | 0 | 0.5 | 0 | 10 | 0 | 0 |
| M1785 | 0.9 | 1.3 | 12 | 1 | 1 | 0 | 0.5 | 0 | 6 | 0 | 0 |
| M1786 | 0.9 | 1.3 | 12 | 1 | 1 | 0 | 0.5 | 0 | 7 | 0 | 0 |
| M1787 | 0.9 | 1.3 | 12 | 1 | 1 | 0 | 0.5 | 0 | 8 | 0 | 0 |
| M1788 | 0.9 | 1.3 | 12 | 1 | 1 | 0 | 0.5 | 0 | 9 | 0 | 0 |
| M1789 | 0.9 | 1.3 | 12 | 1 | 1 | 0 | 0.5 | 0 | 10 | 0 | 0 |
| M1790 | 0.9 | 1.3 | 14 | 1 | 1 | 0 | 0.5 | 0 | 7 | 0 | 0 |
| M1791 | 0.9 | 1.3 | 14 | 1 | 1 | 0 | 0.5 | 0 | 8 | 0 | 0 |
| M1792 | 0.9 | 1.3 | 14 | 1 | 1 | 0 | 0.5 | 0 | 9 | 0 | 0 |
| M1793 | 0.9 | 1.3 | 14 | 1 | 1 | 0 | 0.5 | 0 | 10 | 0 | 0 |
| M1794 | 0.9 | 1.3 | 16 | 1 | 1 | 0 | 0.5 | 0 | 8 | 0 | 0 |
| M1795 | 0.9 | 1.3 | 16 | 1 | 1 | 0 | 0.5 | 0 | 9 | 0 | 0 |
| M1796 | 0.9 | 1.3 | 16 | 1 | 1 | 0 | 0.5 | 0 | 10 | 0 | 0 |
| M1797 | 0.9 | 1.4 | 12 | 1 | 1 | 0 | 0.5 | 0 | 5 | 0 | 0 |
| M1798 | 0.9 | 1.4 | 12 | 1 | 1 | 0 | 0.5 | 0 | 6 | 0 | 0 |
| M1799 | 0.9 | 1.4 | 12 | 1 | 1 | 0 | 0.5 | 0 | 7 | 0 | 0 |
| M1800 | 0.9 | 1.4 | 12 | 1 | 1 | 0 | 0.5 | 0 | 8 | 0 | 0 |
| M1801 | 0.9 | 1.4 | 12 | 1 | 1 | 0 | 0.5 | 0 | 9 | 0 | 0 |
| M1802 | 0.9 | 1.4 | 12 | 1 | 1 | 0 | 0.5 | 0 | 10 | 0 | 0 |
| M1803 | 0.9 | 1.4 | 14 | 1 | 1 | 0 | 0.5 | 0 | 6 | 0 | 0 |
| M1804 | 0.9 | 1.4 | 14 | 1 | 1 | 0 | 0.5 | 0 | 7 | 0 | 0 |
| M1805 | 0.9 | 1.4 | 14 | 1 | 1 | 0 | 0.5 | 0 | 8 | 0 | 0 |
| M1806 | 0.9 | 1.4 | 14 | 1 | 1 | 0 | 0.5 | 0 | 9 | 0 | 0 |
| M1807 | 0.9 | 1.4 | 14 | 1 | 1 | 0 | 0.5 | 0 | 10 | 0 | 0 |
| M1808 | 0.9 | 1.4 | 16 | 1 | 1 | 0 | 0.5 | 0 | 8 | 0 | 0 |
| M1809 | 0.9 | 1.4 | 16 | 1 | 1 | 0 | 0.5 | 0 | 9 | 0 | 0 |
| M1810 | 0.9 | 1.4 | 16 | 1 | 1 | 0 | 0.5 | 0 | 10 | 0 | 0 |
| M1811 | 0.9 | 1.5 | 12 | 1 | 1 | 0 | 0.5 | 0 | 6 | 0 | 0 |
| M1812 | 0.9 | 1.5 | 12 | 1 | 1 | 0 | 0.5 | 0 | 7 | 0 | 0 |
| M1813 | 0.9 | 1.5 | 12 | 1 | 1 | 0 | 0.5 | 0 | 8 | 0 | 0 |
| M1814 | 0.9 | 1.5 | 12 | 1 | 1 | 0 | 0.5 | 0 | 9 | 0 | 0 |
| M1815 | 0.9 | 1.5 | 12 | 1 | 1 | 0 | 0.5 | 0 | 10 | 0 | 0 |
| M1816 | 0.9 | 1.5 | 14 | 1 | 1 | 0 | 0.5 | 0 | 7 | 0 | 0 |
| M1817 | 0.9 | 1.5 | 14 | 1 | 1 | 0 | 0.5 | 0 | 8 | 0 | 0 |
| M1818 | 0.9 | 1.5 | 14 | 1 | 1 | 0 | 0.5 | 0 | 9 | 0 | 0 |
| M1819 | 0.9 | 1.5 | 14 | 1 | 1 | 0 | 0.5 | 0 | 10 | 0 | 0 |
| M1820 | 0.9 | 1.5 | 16 | 1 | 1 | 0 | 0.5 | 0 | 9 | 0 | 0 |
| M1821 | 0.9 | 1.5 | 16 | 1 | 1 | 0 | 0.5 | 0 | 10 | 0 | 0 |
| M1822 | 0.9 | 1.6 | 12 | 1 | 1 | 0 | 0.5 | 0 | 6 | 0 | 0 |
| M1823 | 0.9 | 1.6 | 12 | 1 | 1 | 0 | 0.5 | 0 | 7 | 0 | 0 |
| M1824 | 0.9 | 1.6 | 12 | 1 | 1 | 0 | 0.5 | 0 | 8 | 0 | 0 |
| M1825 | 0.9 | 1.6 | 12 | 1 | 1 | 0 | 0.5 | 0 | 9 | 0 | 0 |
| M1826 | 0.9 | 1.6 | 12 | 1 | 1 | 0 | 0.5 | 0 | 10 | 0 | 0 |
| M1827 | 0.9 | 1.6 | 14 | 1 | 1 | 0 | 0.5 | 0 | 7 | 0 | 0 |
| M1828 | 0.9 | 1.6 | 14 | 1 | 1 | 0 | 0.5 | 0 | 8 | 0 | 0 |
| M1829 | 0.9 | 1.6 | 14 | 1 | 1 | 0 | 0.5 | 0 | 9 | 0 | 0 |
| M1830 | 0.9 | 1.6 | 14 | 1 | 1 | 0 | 0.5 | 0 | 10 | 0 | 0 |
| M1831 | 0.9 | 1.6 | 16 | 1 | 1 | 0 | 0.5 | 0 | 9 | 0 | 0 |
| M1832 | 0.9 | 1.6 | 16 | 1 | 1 | 0 | 0.5 | 0 | 10 | 0 | 0 |
| M1833 | 0.9 | 1.7 | 12 | 1 | 1 | 0 | 0.5 | 0 | 7 | 0 | 0 |
| M1834 | 0.9 | 1.7 | 12 | 1 | 1 | 0 | 0.5 | 0 | 8 | 0 | 0 |
| M1835 | 0.9 | 1.7 | 12 | 1 | 1 | 0 | 0.5 | 0 | 9 | 0 | 0 |
| M1836 | 0.9 | 1.7 | 12 | 1 | 1 | 0 | 0.5 | 0 | 10 | 0 | 0 |
| M1837 | 0.9 | 1.7 | 14 | 1 | 1 | 0 | 0.5 | 0 | 8 | 0 | 0 |
| M1838 | 0.9 | 1.7 | 14 | 1 | 1 | 0 | 0.5 | 0 | 9 | 0 | 0 |
| M1839 | 0.9 | 1.7 | 14 | 1 | 1 | 0 | 0.5 | 0 | 10 | 0 | 0 |
| M1840 | 0.9 | 1.7 | 16 | 1 | 1 | 0 | 0.5 | 0 | 9 | 0 | 0 |
| M1841 | 0.9 | 1.7 | 16 | 1 | 1 | 0 | 0.5 | 0 | 10 | 0 | 0 |
| M1842 | 0.9 | 1.8 | 12 | 1 | 1 | 0 | 0.5 | 0 | 7 | 0 | 0 |
| M1843 | 0.9 | 1.8 | 12 | 1 | 1 | 0 | 0.5 | 0 | 8 | 0 | 0 |
| M1844 | 0.9 | 1.8 | 12 | 1 | 1 | 0 | 0.5 | 0 | 9 | 0 | 0 |
| M1845 | 0.9 | 1.8 | 12 | 1 | 1 | 0 | 0.5 | 0 | 10 | 0 | 0 |
| M1846 | 0.9 | 1.8 | 14 | 1 | 1 | 0 | 0.5 | 0 | 8 | 0 | 0 |
| M1847 | 0.9 | 1.8 | 14 | 1 | 1 | 0 | 0.5 | 0 | 9 | 0 | 0 |
| M1848 | 0.9 | 1.8 | 14 | 1 | 1 | 0 | 0.5 | 0 | 10 | 0 | 0 |
| M1849 | 0.9 | 1.8 | 16 | 1 | 1 | 0 | 0.5 | 0 | 10 | 0 | 0 |
| M1850 | 0.9 | 1.9 | 12 | 1 | 1 | 0 | 0.5 | 0 | 8 | 0 | 0 |
| M1851 | 0.9 | 1.9 | 12 | 1 | 1 | 0 | 0.5 | 0 | 9 | 0 | 0 |
| M1852 | 0.9 | 1.9 | 12 | 1 | 1 | 0 | 0.5 | 0 | 10 | 0 | 0 |
| M1853 | 0.9 | 1.9 | 14 | 1 | 1 | 0 | 0.5 | 0 | 9 | 0 | 0 |
| M1854 | 0.9 | 1.9 | 14 | 1 | 1 | 0 | 0.5 | 0 | 10 | 0 | 0 |
| M1855 | 0.9 | 1.9 | 16 | 1 | 1 | 0 | 0.5 | 0 | 10 | 0 | 0 |

TABLE 3-continued

Alloy chemistries in weight percent, balance Fe, for selected alloys evaluated using thermodynamic models which meet thermodynamic criteria

| Alloy | B | C | Cr | Mn | Mo | Nb | Si | Ti | V | W | Zr |
|---|---|---|---|---|---|---|---|---|---|---|---|
| M1856 | 0.9 | 2 | 12 | 1 | 1 | 0 | 0.5 | 0 | 10 | 0 | 0 |
| M1857 | 0.9 | 2 | 14 | 1 | 1 | 0 | 0.5 | 0 | 10 | 0 | 0 |

Microstructural Criteria

Figure 4:
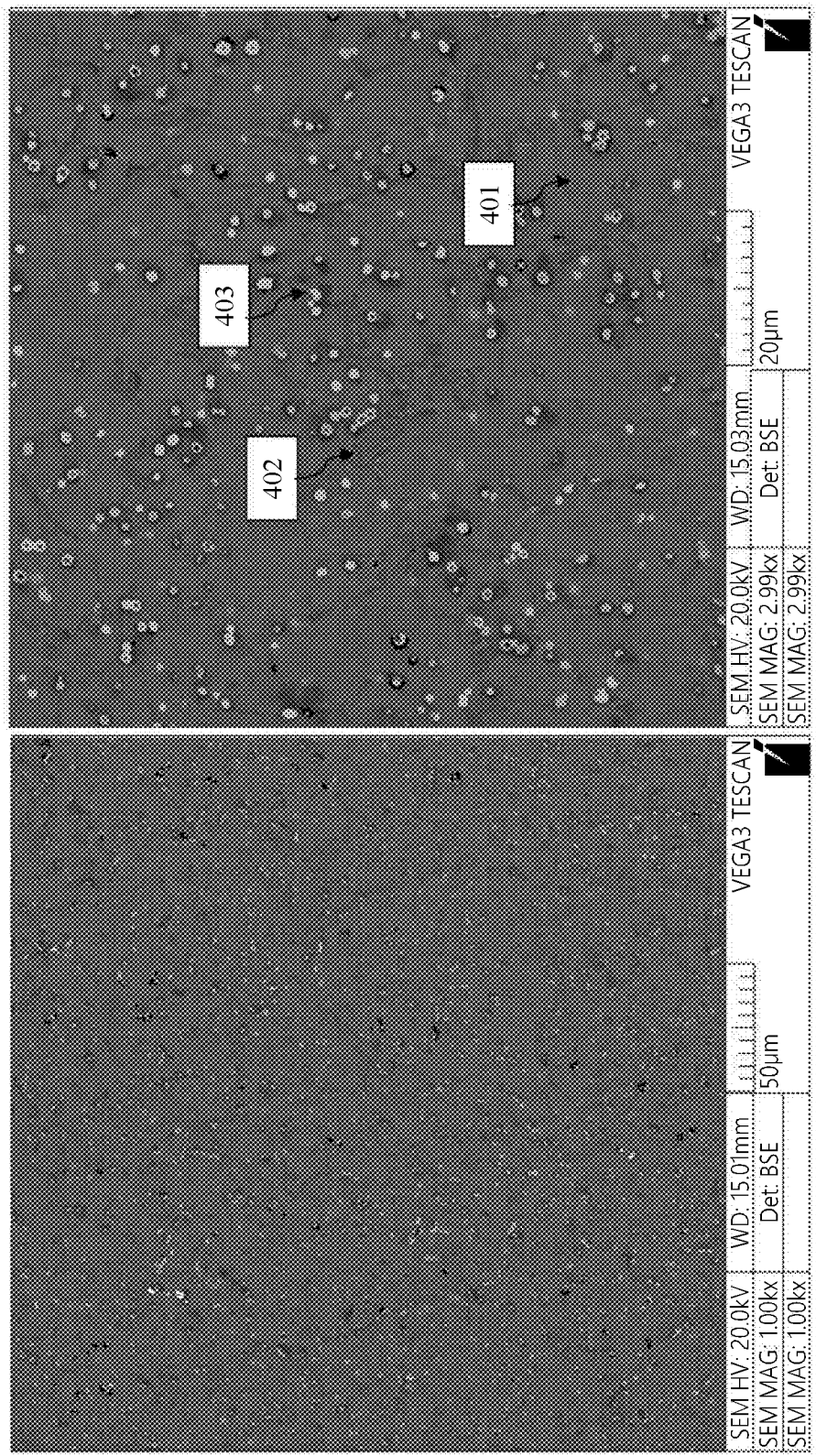
FIG. 4 illustrates an SEM micrograph of an embodiment of a disclosed alloy (Alloy P20X86) at 1,000× (left) and 3,000× (right) magnification.

In some embodiments, the alloy can be described by the microstructural features it possesses. The microstructural features can be 1) martensite is present in the matrix, and 2) the grain boundary carbide and or boride volume fraction is below 15% (or below about 15%) but greater than 0% (or greater than about 0%), and 3) both carbides and borides are present. The thermodynamic criteria can be designed in such a way as to encourage this type of microstructure. An example of the disclosed microstructure is shown in FIG. 4. The microstructure has a martensitic matrix [401] embedded with chromium-rich eutectic borides [402] and niobium rich primary carbides [403].

In some embodiments, the matrix can be at least 10% (or at least about 10%) by volume martensite. In some embodiments, the matrix can be at least 50% (or at least about 50%) by volume martensite. In some embodiments, the matrix can be at least 90% (or at least about 90%) by volume martensite.

In some embodiments, the sum of grain boundary carbides and/or borides can be below 15 volume % (or below about 15 volume %). In some embodiments, the sum of grain boundary carbides and/or borides can be below 10 volume % (or below about 10 volume %). In some embodiments, the sum of grain boundary carbides and/or borides can be below 5 volume % (or below about 5 volume %).

In some embodiments, both carbides and borides can be present.

Performance Criteria

In some embodiments, the alloy can be fully described by the performance characteristics. Four performance characteristics can be used to define the alloy 1) minimum hardness, 2) minimum wear resistance as characterized using ASTM G65 Procedure A, 3) the lack of hot tearing when welded using typical hardfacing procedures, 4) the lack of stress cracking when welded using typical hardfacing procedures, and 5) exhibiting characteristics 1-4 when re-build onto existing welds containing carbon and/or boron. Criteria 1 and 2 are common amongst hardfacing alloys, however alloys exhibiting all four performance criteria are very rare. Furthermore, alloys which exhibit all five performance criteria are not currently known to the state of the art.

Criteria 1 and 2 relate to the intended function of the hardfacing layer, to provide a level of protection against wear to a component. Generally, increased hardness and increased wear resistance can be advantageous. In some embodiments, the minimum hardness of the weld can be 50HRC (or about 50HRC). In some embodiments, the minimum hardness of the weld can be 55HRC (Or about 55 HRC). In some embodiments, the minimum hardness of the weld can be 57HRC (or about 57HRC).

In some embodiments, the wear resistance can be characterized by ASTM G65A dry sand abrasion testing, hereby incorporated by reference in its entirety, where a lower mass loss signifies increased durability. In some embodiments, the maximum mass loss under ASTM G65A testing can be 0.5 g (or about 0.5 g) lost. In some embodiments, the maximum mass loss under ASTM G65A testing can be 0.3 g (or about 0.3 g) lost. In some embodiments, the maximum mass loss under ASTM G65A testing can be 0.2 g (or about 0.2 g) lost.

Criteria 3 and 4 relate to different mechanisms in cracking which are known to occur in hardfacing. The presence of any cracks (whether created through stress crack mechanisms or hot tear mechanism) can create a weld which falls outside of the performance criteria of this disclosure, and is generally undesirable in the field of hardfacing. There are several methods which are known by those skilled in the art to detect cracks in hardfacing welds, such as the dye penetrant test and the magnetic particle inspection. The presence of any cracks revealed through these or equivalent techniques represents a weld which falls outside of the performance criteria of this disclosure Criteria 5 relates to an alloys ability to be welded over existing and potentially dissimilar hardbands. This criterion has utility for the oilfield industry due to the variety of hardbanding alloys currently used and used in the past coupled with the lack of tracking of hardbands onto the drill pipe. In any welding process, there is a certain amount of dilution of the weld material with the base material. As an original single layer weld overlay, the weld material is diluted with the tool joint chemistry, which is typically a 41XX series steel alloy. However, during a re-build, even when the previous hardband is worn flush with the tool joint, the $2^{nd}$ layer hardband can be diluted with the worn $1^{st}$ layer hardband chemistry. When using the MIG welding process, which is common to hardbanding and other forms of hardfacing, the dilution is about 30%. Thus, the $2^{nd}$ layer hardband can be composed of 70% the weld wire chemistry and 30% the chemistry of the original hardband. It is common for hardbanding alloys to have weld wire chemistries containing C+B in the range of 1-2%. Thus, it is common to dilute a new overlay with 0.3-0.6 wt. % C+B. In one embodiment, the alloys of this patent can accommodate 0.3% (or about 0.3%) C+B dilution into the re-building weld bead without hot tearing or stress cracking. In some embodiments, the alloys of this patent can accommodate 0.45% (or about 0.45%) C+B dilution into the re-building weld bead without hot tearing or stress cracking. In some embodiments, the alloys of this patent can accommodate 0.6% (or about 0.6%) C+B dilution into the re-building weld bead without hot tearing or stress cracking.

Table 4 shows select experimental data for the alloy manufactured into ingot form for microstructural and hardness analysis and/or manufactured into welding wire for trials. Complete data is not available for all compositions as some alloys in which thermodynamic or microstructural data indicated poor performance where not selected for welding trials. This table helps demonstrate the uniqueness of these alloys as only 3 out of 86 (3.6%) of the alloys evaluated met the specified performance criteria. Table 1 lists the chemistry of all the alloys evaluated and shown in Table 4.

TABLE 4

Performance Results from Experimental Alloys Selected for Welding Trials

| ALLOY | GB Borides, Carbides | Stress Cracking | Hot Tearing | Hardness |
|---|---|---|---|---|
| 1 | >20%* | YES* | NO | 60 |
| 2 | >20%* | YES* | NO | 60 |
| 44 | | | | 41* |
| 45 | | | | 30* |
| 46 | | | | 41* |
| 47 | | | | 31* |
| 48 | 0% | | | 40* |
| 49 | 0% | | | 47* |
| 50 | 0% | | | 46* |
| 51 | 15-20% | | | 41* |
| 52 | | | | 54 |
| 53 | 0%* | | | 57 |
| 54 | 0%* | NO | YES* | 64 |
| 58 | 0%* | NO | YES* | 61 |
| 59 | | NO | YES* | 50 |
| 60 | | NO | YES* | 49 |
| 61 | | | | 14* |
| 62 | | NO | YES* | 62 |
| 63 | | NO | YES* | 49 |
| 64 | 0%* | NO | YES* | 55 |
| 65 | 0%* | NO | YES* | 50 |
| 66 | 0%* | | | 52 |
| 67 | 0%* | | | 58 |
| 68 | 0%* | | | 56 |
| 69 | 0%* | NO | YES* | 59 |
| 70 | 15-20%* | YES* | NO | 60 |
| 72 | | NO | YES* | N/A |
| 74 | | YES* | NO | N/A |
| 76 | 0%* | NO | YES* | 63 |
| 79 | 1-5% | NO | YES* | 60 |
| 80 | | YES* | NO | N/A |
| 81 | 1-5% | YES* | NO | 56 |
| 82 | | YES* | NO | N/A |
| 84 | | NO | NO | 56 |
| 85 | | NO | NO | 60 |
| 86 | 1-5% | NO | NO | 60 |

*denotes criteria which do not meet either a microstructural embodiment or performance embodiment of this disclosure

EXAMPLES

The following examples are intended to be illustrative and non-limiting:

Example 1

This example illustrates weld testing designing to simulate hardband application and re-application over existing worn layers containing carbon and boron. It was conducted using Alloy #84. A standard 4137 steel 6⅝" tool joint was used as the base material. Three slightly overlapping bands were initially applied onto the tool joint to create a continuous overlay 3" wide and 3.5/32" thick along the outer circumference of the joint. The following weld parameters were used to deposit the $1^{st}$ and $2^{nd}$ layers:

Amps: 265
Volts: 29
Rotation: 2 min 56 sec
Oscillation: 1"
StickOut: 1⅛"
Overlap: ⅛"
PreHeat: 420° F.
Shielding Gas: Argon
Wire Feed: 250

After the deposition of the $1^{st}$ layer, a $2^{nd}$ hardfacing layer was deposited directly on top of the $1^{st}$, resulting in a weld bead of 6.5/32" of total thickness. No hot tears or stress cracks were observed using dye penetrant inspection.

Examples 2-3

These examples illustrate weld testing designing to simulate hardband application and re-application over existing worn layers containing carbon and boron. Similar weld testing was conducted using similar weld parameters for both #85 and #86 alloy. No hot tears or stress cracks were observed using dye penetrant inspection after 2 consecutive layers were welded for either alloy.

Example 4

The following example illustrates weld testing designed to simulate repairing commonly occurring weld imperfections, and represents conditions where stress cracking is highly likely in typical hardfacing materials. Alloy #86 was deposited as a single layer overlay using similar parameters shown in Example 1. However, the welding was stopped and re-started intentionally to produce small gaps in the overlay. 5 total gaps were left in the original overlay. The joint was allowed to cool to 500° F. and two of the gaps were filled in by depositing a small weld overlay over the gap. After welding the $1^{st}$ two patches the joint was then allowed to cool to 480° F., and two of the gaps were filled in with a patch repair. After welding the third patch, the joint was allowed to cool to 450° F. before applying a fourth patch. After welding the fourth patch, the joint was allowed to cool to 450° F. before applying a final patch. No stress cracks or hot tears were created in the weld as a result of filling the 5 gaps with weld patch repairs.

TABLE 5

Glow discharge spectrometer readings for weld wires which met either microstructural criteria, performance criteria, or both

| Alloy | B | C | Cr | Mn | Mo | Nb | Si | Ti | V |
|---|---|---|---|---|---|---|---|---|---|
| 79 | 0.519 | 0.918 | 15.6 | 1.1 | 1.02 | 4.05 | 0.586 | 0.393 | 0.446 |
| 80 | 0.689 | 0.939 | 14.4 | 1.06 | 0.853 | 3 | 0.533 | 0.39 | 0.441 |
| 81 | 0.585 | 0.888 | 14.7 | 1.07 | 0.932 | 3.12 | 0.527 | 0.395 | 0.453 |
| 82 | 0.596 | 1.07 | 14.2 | 1.07 | 0.922 | 2.99 | 0.524 | 0.39 | 0.398 |
| 84 | 0.684 | 0.681 | 16.1 | 1.09 | 1.02 | 3.22 | 0.568 | 0.846 | 0.463 |
| 85 | 0.655 | 0.753 | 15.5 | 1.07 | 0.964 | 3.02 | 0.574 | 0.576 | 0.455 |
| 86 | 0.605 | 0.782 | 14.4 | 1.05 | 0.885 | 3.05 | 0.554 | 0.522 | 0.429 |

Applications and Processes for Use:

Embodiments of alloys disclosed herein can be used in a variety of applications and industries. Some non-limiting examples of applications of use include:

Surface mining applications including but not limited to the following components and coatings for the following components: wear resistant sleeves and/or wear resistant hardfacing for slurry pipelines, mud pump components including pump housing or impeller or hardfacing for mud pump components, ore feed chute components including chute blocks or hardfacing of chute blocks, separation screens including but not limited to rotary breaker screens, banana screens, and shaker screens, liners for autogenous grinding mills and semi-autogenous grinding mills, ground engaging tools and hardfacing for ground engaging tools, wear plate for buckets and dumptruck liners, heel blocks and hardfacing for heel blocks on mining shovels, grader blades and hardfacing for grader blades, stacker reclaimers, siazer crushers, general wear packages for mining components and other communition components.

Upstream oil and gas applications including but not limited to the following components and coatings for the following components: Downhole casing and downhole casing, drill pipe and coatings for drill pipe including hardbanding, mud management components, mud motors, fracking pump sleeves, fracking impellers, fracking blender pumps, stop collars, drill bits and drill bit components, directional drilling equipment and coatings for directional drilling equipment including stabilizers and centralizers, blow out preventers and coatings for blow out preventers and blow out preventer components including the shear rams, oil country tubular goods and coatings for oil country tubular goods.

Downstream oil and gas applications including but not limited to the following components and coatings for the following components: Process vessels and coating for process vessels including steam generation equipment, amine vessels, distillation towers, cyclones, catalytic crackers, general refinery piping, corrosion under insulation protection, sulfur recovery units, convection hoods, sour stripper lines, scrubbers, hydrocarbon drums, and other refinery equipment and vessels.

Pulp and paper applications including but not limited to the following components and coatings for the following components: Rolls used in paper machines including yankee dryers and other dryers, calendar rolls, machine rolls, press rolls, digesters, pulp mixers, pulpers, pumps, boilers, shredders, tissue machines, roll and bale handling machines, doctor blades, evaporators, pulp mills, head boxes, wire parts, press parts, M.G. cylinders, pope reels, winders, vacuum pumps, deflakers, and other pulp and paper equipment.

Power generation applications including but not limited to the following components and coatings for the following components: boiler tubes, precipitators, fireboxes, turbines, generators, cooling towers, condensers, chutes and troughs, augers, bag houses, ducts, ID fans, coal piping, and other power generation components.

Agriculture applications including but not limited to the following components and coatings for the following components: chutes, base cutter blades, troughs, primary fan blades, secondary fan blades, augers and other agricultural applications.

Construction applications including but not limited to the following components and coatings for the following components: cement chutes, cement piping, bag houses, mixing equipment and other construction applications.

Machine element applications including but not limited to the following components and coatings for the following components: Shaft journals, paper rolls, gear boxes, drive rollers, impellers, general reclamation and dimensional restoration applications and other machine element applications.

Steel applications including but not limited to the following components and coatings for the following components: cold rolling mills, hot rolling mills, wire rod mills, galvanizing lines, continue pickling lines, continuous casting rolls and other steel mill rolls, and other steel applications.

Embodiments of alloys disclosed herein can be produced and or deposited in a variety of techniques effectively. Some non-limiting examples of processes include:

Thermal spray process including but not limited to those using a wire feedstock such as twin wire arc, spray, high velocity arc spray, combustion spray and those using a powder feedstock such as high velocity oxygen fuel, high velocity air spray, plasma spray, detonation gun spray, and cold spray. Wire feedstock can be in the form of a metal core wire, solid wire, or flux core wire. Powder feedstock can be either a single homogenous alloy or a combination of multiple alloy powder which result in the desired chemistry when melted together.

Welding processes including but not limited to those using a wire feedstock including but not limited to metal inert gas (MIG) welding, tungsten inert gas (TIG) welding, arc welding, submerged arc welding, open arc welding, bulk welding, laser cladding, and those using a powder feedstock including but not limited to laser cladding and plasma transferred arc welding. Wire feedstock can be in the form of a metal core wire, solid wire, or flux core wire. Powder feedstock can be either a single homogenous alloy or a combination of multiple alloy powder which result in the desired chemistry when melted together.

Casting processes including but not limited to processes typical to producing cast iron including but not limited to sand casting, permanent mold casting, chill casting, investment casting, lost foam casting, die casting, centrifugal casting, glass casting, slip casting and process typical to producing wrought steel products including continuous casting processes.

Post processing techniques including but not limited to but not limited to rolling, forging, surface treatments such as carburizing, nitriding, carbonitriding, heat treatments including but not limited to austenitizing, normalizing, annealing, stress relieving, tempering, aging, quenching, cryogenic treatments, flame hardening, induction hardening, differential hardening, case hardening, decarburization, machining, grinding, cold working, work hardening, and welding.

One of the more applicable uses of this technology is in applications where coatings are deposited on-site, in the field, or in locations where proper ventilation, dust collection, and other safety measures cannot be easily met. Some well-known non-limiting examples of these applications include power generation applications such as the coating of boiler tubes, upstream refinery applications such as the coating of refinery vessels, and pulp and paper applications such as the coating and grinding of yankee dryers.

From the foregoing description, it will be appreciated that an inventive product and approaches for crack resistant hardbanding alloys are disclosed. While several components, techniques and aspects have been described with a certain degree of particularity, it is manifest that many changes can be made in the specific designs, constructions and methodology herein above described without departing from the spirit and scope of this disclosure.

Certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as any subcombination or variation of any subcombination.

Moreover, while methods may be depicted in the drawings or described in the specification in a particular order, such methods need not be performed in the particular order shown or in sequential order, and that all methods need not be performed, to achieve desirable results. Other methods that are not depicted or described can be incorporated in the example methods and processes. For example, one or more additional methods can be performed before, after, simultaneously, or between any of the described methods. Further, the methods may be rearranged or reordered in other implementations. Also, the separation of various system components in the implementations described above should not be understood as requiring such separation in all implementations, and it should be understood that the described components and systems can generally be integrated together in a single product or packaged into multiple products. Additionally, other implementations are within the scope of this disclosure.

Conditional language, such as "can," "could," "might," or "may," unless specifically stated otherwise, or otherwise understood within the context as used, is generally intended to convey that certain embodiments include or do not include, certain features, elements, and/or steps. Thus, such conditional language is not generally intended to imply that features, elements, and/or steps are in any way required for one or more embodiments.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than or equal to 10% of, within less than or equal to 5% of, within less than or equal to 1% of, within less than or equal to 0.1% of, and within less than or equal to 0.01% of the stated amount. If the stated amount is 0 (e.g., none, having no), the above recited ranges can be specific ranges, and not within a particular % of the value. For example, within less than or equal to 10 wt./vol. % of, within less than or equal to 5 wt./vol. % of, within less than or equal to 1 wt./vol. % of, within less than or equal to 0.1 wt./vol. % of, and within less than or equal to 0.01 wt./vol. % of the stated amount.

Some embodiments have been described in connection with the accompanying drawings. The figures are drawn to scale, but such scale should not be limiting, since dimensions and proportions other than what are shown are contemplated and are within the scope of the disclosed inventions. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

While a number of embodiments and variations thereof have been described in detail, other modifications and methods of using the same will be apparent to those of skill in the art. Accordingly, it should be understood that various applications, modifications, materials, and substitutions can be made of equivalents without departing from the unique and inventive disclosure herein or the scope of the claims.

What is claimed is:

1. A hardfacing deposit, wherein the hardfacing deposit comprises:
   Fe and about 0.68 wt. % to about 1.25 wt. % C; and
   a matrix comprising at least 50% martensite by volume, a macro-hardness of 57 HRC or greater, and a high resistance to stress cracking and hot tearing when welded as a single layer or over a worn existing hardfacing layer;
   wherein a minimum carbon level in the matrix is 0.6 wt. %;
   wherein the hardfacing deposit contains greater than 0 volume % grain boundary carbides and/or borides and less than about 15% grain boundary carbides and/or borides; and
   wherein the hardfacing deposit has high abrasion resistance as characterized by an ASTM G65A mass loss of less than 0.5 grams.

2. The hardfacing deposit of claim 1, wherein the hardfacing deposit contains both carbide and boride precipitates when welded over a worn existing hardfacing layer.

3. The hardfacing deposit of claim 1, wherein the hardfacing deposit comprises Fe and, in wt. %:
   B: about 0.6 to about 0.9;
   Cr: about 14.25 to about 26; and
   Nb+Ti+V: about 3.5 to about 4.5.

4. The hardfacing deposit of claim 3, wherein the hardfacing deposit further comprises, in wt. %:
   Mn: about 1.1;
   Mo: about 1; and
   Si: about 0.5.

5. The hardfacing deposit of claim 1, wherein the hardfacing deposit comprises Fe and, in wt. %:
   B: 1;
   C: 0.8;
   Cr: 16; and
   Nb: 3.5.

6. The hardfacing deposit of claim 5, wherein the hardfacing deposit does not contain Mn, Mo, Si, Ti, V, W, or Zr.

7. The hardfacing deposit of claim 1, wherein the matrix comprises at least 90% martensite by volume.

8. The hardfacing deposit of claim 1, wherein a majority of a composition of the hardfacing deposit is Fe.

9. The hardfacing deposit of claim 1, wherein the hardfacing deposit contains less than about 10% grain boundary carbides and/or borides.

10. The hardfacing deposit of claim 1, wherein the hardfacing deposit contains less than about 5% grain boundary carbides and/or borides.

11. The hardfacing deposit of claim 1, wherein the hardfacing deposit is formed from a wire.

12. The hardfacing deposit of claim 11, wherein the wire comprises Fe and, in wt. %:
   C: about 0.75 to about 1.25;
   B: about 0.6 to about 0.9;
   Cr: about 14.25 to about 26; and
   Nb+Ti+V: about 3.5 to about 4.5.

* * * * *